(12) United States Patent
Shuros et al.

(10) Patent No.: US 10,350,423 B2
(45) Date of Patent: Jul. 16, 2019

(54) DELIVERY SYSTEM WITH FORCE SENSOR FOR LEADLESS CARDIAC DEVICE

(71) Applicant: CARDIAC PACEMAKERS, INC., St. Paul, MN (US)

(72) Inventors: Allan Charles Shuros, St. Paul, MN (US); Shibaji Shome, Arden Hills, MN (US); Brian Soltis, St. Paul, MN (US); Brian L. Schmidt, White Bear Lake, MN (US); Kevin John Stalsberg, White Bear Lake, MN (US)

(73) Assignee: CARDIAC PACEMAKERS, INC., St. Paul, MN (US)

( * ) Notice: Subject to any disclaimer, the term of this patent is extended or adjusted under 35 U.S.C. 154(b) by 44 days.

(21) Appl. No.: 15/423,078

(22) Filed: Feb. 2, 2017

(65) Prior Publication Data

US 2017/0224997 A1      Aug. 10, 2017

Related U.S. Application Data

(60) Provisional application No. 62/291,330, filed on Feb. 4, 2016.

(51) Int. Cl.
*A61N 1/375* (2006.01)
*A61N 1/362* (2006.01)
*A61N 1/05* (2006.01)

(52) U.S. Cl.
CPC .......... *A61N 1/3756* (2013.01); *A61N 1/0573* (2013.01); *A61N 1/362* (2013.01); *A61N 2001/058* (2013.01)

(58) Field of Classification Search
CPC .... A61N 1/3756; A61N 1/0573; A61N 1/362; A61N 2001/058

(Continued)

(56) References Cited

U.S. PATENT DOCUMENTS 2,959,056 A    11/1960   Max et al.
3,835,864 A     9/1974   Rasor et al.
(Continued)

FOREIGN PATENT DOCUMENTS

AU    2008279789 B2    10/2011
AU    2008329620 B2     5/2014
(Continued)

OTHER PUBLICATIONS

US 8,180,431 B2, 05/2012, Govari et al. (withdrawn)
(Continued)

*Primary Examiner* — Carl H Layno
*Assistant Examiner* — Erin M Piateski
(74) *Attorney, Agent, or Firm* — Seager, Tufte & Wickhem LLP.

(57) ABSTRACT

A device configured to deliver and deploy an implantable medical device (IMD) includes a handle assembly and a shaft extending distally therefrom. A device containment housing configured to accommodate the IMD is coupled to the distal region of the shaft. At least one of the shaft and device containment housing includes a compressible region that is configured to compress by an amount that is related to an applied force. The device may include a first position indicator and a second position indicator. An applied force causes the compressible region to compress by an amount that is related to the applied force, causing a change in distance between the first position indicator and the second position indicator and thus providing an indication of the applied force.

10 Claims, 31 Drawing Sheets

(58) Field of Classification Search
USPC ........................................................ 607/122
See application file for complete search history.

(56) References Cited

U.S. PATENT DOCUMENTS

| | | |
|---|---|---|
| 3,943,936 A | 3/1976 | Rasor et al. |
| 4,142,530 A | 3/1979 | Wittkampf |
| 4,151,513 A | 4/1979 | Menken et al. |
| 4,157,720 A | 6/1979 | Greatbatch |
| RE30,366 E | 8/1980 | Rasor et al. |
| 4,243,045 A | 1/1981 | Maas |
| 4,250,884 A | 2/1981 | Hartlaub et al. |
| 4,256,115 A | 3/1981 | Bilitch |
| 4,263,919 A | 4/1981 | Levin |
| 4,274,423 A | 6/1981 | Mizuno et al. |
| 4,310,000 A | 1/1982 | Lindemans |
| 4,312,354 A | 1/1982 | Walters |
| 4,323,081 A | 4/1982 | Wiebusch |
| 4,357,946 A | 11/1982 | Dutcher et al. |
| 4,365,639 A | 12/1982 | Goldreyer |
| 4,440,173 A | 4/1984 | Hudziak et al. |
| 4,469,091 A | 9/1984 | Slanetz, Jr. |
| 4,476,868 A | 10/1984 | Thompson |
| 4,522,208 A | 6/1985 | Buffet |
| 4,537,200 A | 8/1985 | Widrow |
| 4,556,063 A | 12/1985 | Thompson et al. |
| 4,562,841 A | 1/1986 | Brockway et al. |
| 4,593,702 A | 6/1986 | Kepski et al. |
| 4,593,955 A | 6/1986 | Leiber |
| 4,630,611 A | 12/1986 | King |
| 4,635,639 A | 1/1987 | Hakala et al. |
| 4,674,508 A | 6/1987 | DeCote |
| 4,712,554 A | 12/1987 | Garson |
| 4,729,376 A | 3/1988 | DeCote |
| 4,754,753 A | 7/1988 | King |
| 4,759,366 A | 7/1988 | Callaghan |
| 4,776,338 A | 10/1988 | Lekholm et al. |
| 4,787,389 A | 11/1988 | Tarjan |
| 4,793,353 A | 12/1988 | Borkan |
| 4,819,662 A | 4/1989 | Heil et al. |
| 4,858,610 A | 8/1989 | Callaghan et al. |
| 4,886,064 A | 12/1989 | Strandberg |
| 4,887,609 A | 12/1989 | Cole |
| 4,928,688 A | 5/1990 | Mower |
| 4,967,746 A | 11/1990 | Vandegriff |
| 4,987,897 A | 1/1991 | Funke |
| 4,989,602 A | 2/1991 | Sholder et al. |
| 5,012,806 A | 5/1991 | Bellis |
| 5,036,849 A | 8/1991 | Hauck et al. |
| 5,040,534 A | 8/1991 | Mann et al. |
| 5,058,581 A | 10/1991 | Silvian |
| 5,078,134 A | 1/1992 | Heilman et al. |
| 5,109,845 A | 5/1992 | Yuuchi et al. |
| 5,113,859 A | 5/1992 | Funke |
| 5,113,869 A | 5/1992 | Nappholz et al. |
| 5,117,824 A | 6/1992 | Keimel et al. |
| 5,127,401 A | 7/1992 | Grevious et al. |
| 5,133,353 A | 7/1992 | Hauser |
| 5,144,950 A | 9/1992 | Stoop et al. |
| 5,170,784 A | 12/1992 | Ramon et al. |
| 5,179,945 A | 1/1993 | Hofwegen et al. |
| 5,193,539 A | 3/1993 | Schulman et al. |
| 5,193,540 A | 3/1993 | Schulman et al. |
| 5,241,961 A | 9/1993 | Henry |
| 5,243,977 A | 9/1993 | Trabucco et al. |
| 5,255,679 A | 10/1993 | Imran |
| 5,259,387 A | 11/1993 | DePinto |
| 5,269,326 A | 12/1993 | Verner |
| 5,284,136 A | 2/1994 | Hauck et al. |
| 5,300,107 A | 4/1994 | Stokes et al. |
| 5,301,677 A | 4/1994 | Hsung |
| 5,305,760 A | 4/1994 | McKown et al. |
| 5,312,439 A | 5/1994 | Loeb |
| 5,313,953 A | 5/1994 | Yomtov et al. |
| 5,314,459 A | 5/1994 | Swanson et al. |
| 5,318,597 A | 6/1994 | Hauck et al. |
| 5,324,316 A | 6/1994 | Schulman et al. |
| 5,331,966 A | 7/1994 | Bennett et al. |
| 5,334,222 A | 8/1994 | Salo et al. |
| 5,341,807 A | 8/1994 | Nardella |
| 5,342,408 A | 8/1994 | deCoriolis et al. |
| 5,370,667 A | 12/1994 | Alt |
| 5,372,606 A | 12/1994 | Lang et al. |
| 5,376,106 A | 12/1994 | Stahmann et al. |
| 5,383,915 A | 1/1995 | Adams |
| 5,388,578 A | 2/1995 | Yomtov et al. |
| 5,396,887 A | 3/1995 | Imran |
| 5,404,877 A | 4/1995 | Nolan et al. |
| 5,405,367 A | 4/1995 | Schulman et al. |
| 5,411,031 A | 5/1995 | Yomtov |
| 5,411,525 A | 5/1995 | Swanson et al. |
| 5,411,535 A | 5/1995 | Fujii et al. |
| 5,423,808 A | 6/1995 | Edwards et al. |
| 5,447,529 A | 9/1995 | Marchlinski et al. |
| 5,456,691 A | 10/1995 | Snell |
| 5,458,622 A | 10/1995 | Alt |
| 5,466,246 A | 11/1995 | Silvian |
| 5,468,254 A | 11/1995 | Hahn et al. |
| 5,472,453 A | 12/1995 | Alt |
| 5,514,171 A * | 5/1996 | Hoegnelid ............... A61B 5/03 600/488 |
| 5,522,866 A | 6/1996 | Fernald |
| 5,540,727 A | 7/1996 | Tockman et al. |
| 5,545,186 A | 8/1996 | Olson et al. |
| 5,545,202 A | 8/1996 | Dahl et al. |
| 5,562,721 A | 10/1996 | Marchlinski et al. |
| 5,571,146 A | 11/1996 | Jones et al. |
| 5,591,214 A | 1/1997 | Lu |
| 5,620,466 A | 4/1997 | Haefner et al. |
| 5,634,938 A | 6/1997 | Swanson et al. |
| 5,649,968 A | 7/1997 | Alt et al. |
| 5,662,688 A | 9/1997 | Haefner et al. |
| 5,673,704 A | 10/1997 | Marchlinski et al. |
| 5,674,259 A | 10/1997 | Gray |
| 5,683,426 A | 11/1997 | Greenhut et al. |
| 5,683,432 A | 11/1997 | Goedeke et al. |
| 5,697,925 A | 12/1997 | Taylor |
| 5,706,823 A | 1/1998 | Wodlinger |
| 5,709,215 A | 1/1998 | Perttu et al. |
| 5,718,701 A | 2/1998 | Shai et al. |
| 5,720,770 A | 2/1998 | Nappholz et al. |
| 5,728,154 A | 3/1998 | Crossett et al. |
| 5,733,281 A | 3/1998 | Nardella |
| 5,741,314 A | 4/1998 | Daly et al. |
| 5,741,315 A | 4/1998 | Lee et al. |
| 5,752,976 A | 5/1998 | Duffin et al. |
| 5,752,977 A | 5/1998 | Grevious et al. |
| 5,755,736 A | 5/1998 | Gillberg et al. |
| 5,759,199 A | 6/1998 | Snell et al. |
| 5,774,501 A | 6/1998 | Halpern et al. |
| 5,791,350 A | 8/1998 | Morton |
| 5,792,195 A | 8/1998 | Carlson et al. |
| 5,792,202 A | 8/1998 | Rueter |
| 5,792,203 A | 8/1998 | Schroeppel |
| 5,792,205 A | 8/1998 | Alt et al. |
| 5,792,208 A | 8/1998 | Gray |
| 5,807,265 A | 9/1998 | Itoigawa et al. |
| 5,814,089 A | 9/1998 | Stokes et al. |
| 5,827,216 A | 10/1998 | Igo et al. |
| 5,836,985 A | 11/1998 | Rostami et al. |
| 5,836,987 A | 11/1998 | Baumann et al. |
| 5,836,990 A | 11/1998 | Li |
| 5,842,977 A | 12/1998 | Lesho et al. |
| 5,843,075 A | 12/1998 | Taylor |
| 5,855,592 A | 1/1999 | McGee et al. |
| 5,855,593 A | 1/1999 | Olson et al. |
| 5,868,737 A | 2/1999 | Taylor et al. |
| 5,873,894 A | 2/1999 | Vandegriff et al. |
| 5,891,184 A | 4/1999 | Lee et al. |
| 5,897,586 A | 4/1999 | Molina |
| 5,899,876 A | 5/1999 | Flower |
| 5,899,928 A | 5/1999 | Sholder et al. |
| 5,919,214 A | 7/1999 | Ciciarelli et al. |
| 5,935,078 A | 8/1999 | Feierbach |

(56) References Cited

U.S. PATENT DOCUMENTS

| | | |
|---|---|---|
| 5,941,906 A | 8/1999 | Barreras, Jr. et al. |
| 5,944,022 A | 8/1999 | Nardella et al. |
| 5,944,744 A | 8/1999 | Paul et al. |
| 5,954,757 A | 9/1999 | Gray |
| 5,971,980 A | 10/1999 | Sherman |
| 5,978,713 A | 11/1999 | Prutchi et al. |
| 5,991,660 A | 11/1999 | Goyal |
| 5,991,661 A | 11/1999 | Park et al. |
| 5,999,848 A | 12/1999 | Gord et al. |
| 5,999,857 A | 12/1999 | Weijand et al. |
| 6,013,074 A | 1/2000 | Taylor |
| 6,016,445 A | 1/2000 | Baura |
| 6,019,729 A | 2/2000 | Itoigawa et al. |
| 6,026,320 A | 2/2000 | Carlson et al. |
| 6,029,085 A | 2/2000 | Olson et al. |
| 6,039,731 A | 3/2000 | Taylor et al. |
| 6,041,250 A | 3/2000 | DePinto |
| 6,044,298 A | 3/2000 | Salo et al. |
| 6,044,300 A | 3/2000 | Gray |
| 6,050,267 A | 4/2000 | Nardella et al. |
| 6,055,454 A | 4/2000 | Heemels |
| 6,063,078 A | 5/2000 | Wittkampf |
| 6,073,050 A | 6/2000 | Griffith |
| 6,076,016 A | 6/2000 | Feierbach |
| 6,077,236 A | 6/2000 | Cunningham |
| 6,080,187 A | 6/2000 | Alt et al. |
| 6,083,248 A | 7/2000 | Thompson |
| 6,106,551 A | 8/2000 | Crossett et al. |
| 6,113,592 A | 9/2000 | Taylor |
| 6,113,593 A | 9/2000 | Tu et al. |
| 6,115,636 A | 9/2000 | Ryan |
| 6,128,526 A | 10/2000 | Stadler et al. |
| 6,141,581 A | 10/2000 | Colson et al. |
| 6,141,588 A | 10/2000 | Cox et al. |
| 6,141,592 A | 10/2000 | Pauly |
| 6,144,879 A | 11/2000 | Gray |
| 6,162,195 A | 12/2000 | Igo et al. |
| 6,164,284 A | 12/2000 | Schulman et al. |
| 6,167,310 A | 12/2000 | Grevious |
| 6,201,993 B1 | 3/2001 | Kruse et al. |
| 6,208,894 B1 | 3/2001 | Schulman et al. |
| 6,211,799 B1 | 4/2001 | Post et al. |
| 6,217,573 B1 | 4/2001 | Webster |
| 6,217,574 B1 | 4/2001 | Webster |
| 6,221,011 B1 | 4/2001 | Bardy |
| 6,221,023 B1 | 4/2001 | Matsuba et al. |
| 6,240,316 B1 | 5/2001 | Richmond et al. |
| 6,240,317 B1 | 5/2001 | Villaseca et al. |
| 6,241,724 B1 | 6/2001 | Fleischman et al. |
| 6,256,534 B1 | 7/2001 | Dahl |
| 6,259,947 B1 | 7/2001 | Olson et al. |
| 6,264,653 B1 | 7/2001 | Falwell |
| 6,266,558 B1 | 7/2001 | Gozani et al. |
| 6,266,567 B1 | 7/2001 | Ishikawa et al. |
| 6,270,457 B1 | 8/2001 | Bardy |
| 6,272,371 B1 | 8/2001 | Shlomo |
| 6,272,377 B1 | 8/2001 | Sweeney et al. |
| 6,273,856 B1 | 8/2001 | Sun et al. |
| 6,277,072 B1 | 8/2001 | Bardy |
| 6,280,380 B1 | 8/2001 | Bardy |
| 6,285,907 B1 | 9/2001 | Kramer et al. |
| 6,292,698 B1 | 9/2001 | Duffin et al. |
| 6,295,473 B1 | 9/2001 | Rosar |
| 6,297,943 B1 | 10/2001 | Carson |
| 6,298,271 B1 | 10/2001 | Weijand |
| 6,304,776 B1 | 10/2001 | Muntermann |
| 6,307,751 B1 | 10/2001 | Bodony et al. |
| 6,312,378 B1 | 11/2001 | Bardy |
| 6,315,721 B2 | 11/2001 | Schulman et al. |
| 6,322,558 B1 | 11/2001 | Taylor et al. |
| 6,336,903 B1 | 1/2002 | Bardy |
| 6,345,202 B2 | 2/2002 | Richmond et al. |
| 6,351,667 B1 | 2/2002 | Godie |
| 6,351,669 B1 | 2/2002 | Hartley et al. |
| 6,353,759 B1 | 3/2002 | Hartley et al. |
| 6,358,203 B2 | 3/2002 | Bardy |
| 6,361,780 B1 | 3/2002 | Ley et al. |
| 6,368,284 B1 | 4/2002 | Bardy |
| 6,371,922 B1 | 4/2002 | Baumann et al. |
| 6,391,024 B1 | 5/2002 | Sun et al. |
| 6,398,728 B1 | 6/2002 | Bardy |
| 6,400,982 B2 | 6/2002 | Sweeney et al. |
| 6,400,990 B1 | 6/2002 | Silvian |
| 6,408,208 B1 | 6/2002 | Sun |
| 6,409,674 B1 | 6/2002 | Brockway et al. |
| 6,411,848 B2 | 6/2002 | Kramer et al. |
| 6,423,057 B1 | 7/2002 | He et al. |
| 6,424,865 B1 | 7/2002 | Ding |
| 6,434,429 B1 | 8/2002 | Kraus et al. |
| 6,436,059 B1 | 8/2002 | Zanelli |
| 6,438,410 B2 | 8/2002 | Hsu et al. |
| 6,438,417 B1 | 8/2002 | Rockwell et al. |
| 6,438,421 B1 | 8/2002 | Stahmann et al. |
| 6,440,066 B1 | 8/2002 | Bardy |
| 6,441,747 B1 | 8/2002 | Khair et al. |
| 6,442,426 B1 | 8/2002 | Kroll |
| 6,442,432 B2 | 8/2002 | Lee |
| 6,443,891 B1 | 9/2002 | Grevious |
| 6,445,953 B1 | 9/2002 | Bulkes et al. |
| 6,453,200 B1 | 9/2002 | Koslar |
| 6,459,929 B1 | 10/2002 | Hopper et al. |
| 6,470,215 B1 | 10/2002 | Kraus et al. |
| 6,471,645 B1 | 10/2002 | Warkentin et al. |
| 6,480,745 B2 | 11/2002 | Nelson et al. |
| 6,487,443 B2 | 11/2002 | Olson et al. |
| 6,490,487 B1 | 12/2002 | Kraus et al. |
| 6,498,951 B1 | 12/2002 | Larson et al. |
| 6,507,755 B1 | 1/2003 | Gozani et al. |
| 6,507,759 B1 | 1/2003 | Prutchi et al. |
| 6,512,940 B1 | 1/2003 | Brabec et al. |
| 6,522,915 B1 | 2/2003 | Ceballos et al. |
| 6,526,311 B2 | 2/2003 | Begemann |
| 6,539,253 B2 | 3/2003 | Thompson et al. |
| 6,542,775 B2 | 4/2003 | Ding et al. |
| 6,546,270 B1 | 4/2003 | Goldin et al. |
| 6,551,302 B1 | 4/2003 | Rosinko et al. |
| 6,553,258 B2 | 4/2003 | Stahmann et al. |
| 6,561,975 B1 | 5/2003 | Pool et al. |
| 6,564,807 B1 | 5/2003 | Schulman et al. |
| 6,569,160 B1 | 5/2003 | Goldin et al. |
| 6,574,506 B2 | 6/2003 | Kramer et al. |
| 6,584,351 B1 | 6/2003 | Ekwall |
| 6,584,352 B2 | 6/2003 | Combs et al. |
| 6,597,948 B1 | 7/2003 | Rockwell et al. |
| 6,597,951 B2 | 7/2003 | Kramer et al. |
| 6,622,046 B2 | 9/2003 | Fraley et al. |
| 6,628,985 B2 | 9/2003 | Sweeney et al. |
| 6,645,145 B1 | 11/2003 | Dreschel et al. |
| 6,647,292 B1 | 11/2003 | Bardy et al. |
| 6,650,920 B2 | 11/2003 | Schaldach et al. |
| 6,666,844 B1 | 12/2003 | Igo et al. |
| 6,666,862 B2 | 12/2003 | Jain et al. |
| 6,669,686 B1 | 12/2003 | Singh |
| 6,689,117 B2 | 2/2004 | Sweeney et al. |
| 6,690,959 B2 | 2/2004 | Thompson |
| 6,694,189 B2 | 2/2004 | Begemann |
| 6,695,808 B2 | 2/2004 | Tom |
| 6,704,602 B2 | 3/2004 | Berg et al. |
| 6,712,778 B1 | 3/2004 | Jeffcoat et al. |
| 6,714,806 B2 | 3/2004 | Iaizzo et al. |
| 6,718,212 B2 | 4/2004 | Parry et al. |
| 6,721,597 B1 | 4/2004 | Bardy et al. |
| 6,730,079 B2 | 5/2004 | Lovewell |
| 6,738,670 B1 | 5/2004 | Almendinger et al. |
| 6,746,797 B2 | 6/2004 | Benson et al. |
| 6,749,566 B2 | 6/2004 | Russ |
| 6,758,810 B2 | 7/2004 | Lebel et al. |
| 6,763,269 B2 | 7/2004 | Cox |
| 6,778,860 B2 | 8/2004 | Ostroff et al. |
| 6,788,971 B1 | 9/2004 | Sloman et al. |
| 6,788,974 B2 | 9/2004 | Bardy et al. |
| 6,800,986 B2 | 10/2004 | Yamauchi |
| 6,804,558 B2 | 10/2004 | Haller et al. |
| 6,807,442 B1 | 10/2004 | Myklebust et al. |

(56) References Cited

U.S. PATENT DOCUMENTS

| | | |
|---|---|---|
| 6,824,521 B2 | 11/2004 | Rich et al. |
| 6,837,886 B2 | 1/2005 | Collins et al. |
| 6,847,844 B2 | 1/2005 | Sun et al. |
| 6,871,095 B2 | 3/2005 | Stahmann et al. |
| 6,878,112 B2 | 4/2005 | Linberg et al. |
| 6,885,889 B2 | 4/2005 | Chinchoy |
| 6,892,094 B2 | 5/2005 | Ousdigian et al. |
| 6,897,788 B2 | 5/2005 | Khair et al. |
| 6,904,315 B2 | 6/2005 | Panken et al. |
| 6,915,149 B2 | 7/2005 | Ben-Haim |
| 6,922,592 B2 | 7/2005 | Thompson et al. |
| 6,926,670 B2 | 8/2005 | Rich et al. |
| 6,931,282 B2 | 8/2005 | Esler |
| 6,934,585 B1 | 8/2005 | Schloss et al. |
| 6,955,675 B2 | 10/2005 | Jain |
| 6,957,107 B2 | 10/2005 | Rogers et al. |
| 6,964,661 B2 | 11/2005 | Rioux et al. |
| 6,978,176 B2 | 12/2005 | Lattouf |
| 6,985,773 B2 | 1/2006 | Arx et al. |
| 6,990,375 B2 | 1/2006 | Kloss et al. |
| 7,001,366 B2 | 2/2006 | Ballard |
| 7,001,383 B2 | 2/2006 | Keidar |
| 7,003,350 B2 | 2/2006 | Denker et al. |
| 7,006,864 B2 | 2/2006 | Echt et al. |
| 7,013,178 B2 | 3/2006 | Reinke et al. |
| 7,027,871 B2 | 4/2006 | Burnes et al. |
| 7,050,849 B2 | 5/2006 | Echt et al. |
| 7,060,031 B2 | 6/2006 | Webb et al. |
| 7,063,693 B2 | 6/2006 | Guenst |
| 7,072,703 B2 | 7/2006 | Zhang et al. |
| 7,082,336 B2 | 7/2006 | Ransbury et al. |
| 7,085,606 B2 | 8/2006 | Flach et al. |
| 7,092,758 B2 | 8/2006 | Sun et al. |
| 7,110,824 B2 | 9/2006 | Amundson et al. |
| 7,120,504 B2 | 10/2006 | Osypka |
| 7,130,681 B2 | 10/2006 | Gebhardt et al. |
| 7,139,613 B2 | 11/2006 | Reinke et al. |
| 7,142,912 B2 | 11/2006 | Wagner et al. |
| 7,146,225 B2 | 12/2006 | Guenst et al. |
| 7,146,226 B2 | 12/2006 | Lau et al. |
| 7,149,581 B2 | 12/2006 | Goedeke |
| 7,149,588 B2 | 12/2006 | Lau et al. |
| 7,158,839 B2 | 1/2007 | Lau |
| 7,162,307 B2 | 1/2007 | Patrias |
| 7,164,952 B2 | 1/2007 | Lau et al. |
| 7,177,700 B1 | 2/2007 | Cox |
| 7,181,505 B2 | 2/2007 | Haller et al. |
| 7,184,830 B2 | 2/2007 | Echt et al. |
| 7,186,214 B2 | 3/2007 | Ness |
| 7,191,015 B2 | 3/2007 | Lamson et al. |
| 7,192,427 B2 | 3/2007 | Chapelon et al. |
| 7,200,437 B1 | 4/2007 | Nabutovsky et al. |
| 7,200,439 B2 | 4/2007 | Zdeblick et al. |
| 7,206,423 B1 | 4/2007 | Feng et al. |
| 7,209,785 B2 | 4/2007 | Kim et al. |
| 7,209,790 B2 | 4/2007 | Thompson et al. |
| 7,211,062 B2 | 5/2007 | Kwon |
| 7,211,063 B2 | 5/2007 | Tom |
| 7,211,884 B1 | 5/2007 | Davis et al. |
| 7,212,871 B1 | 5/2007 | Morgan |
| 7,226,440 B2 | 6/2007 | Gelfand et al. |
| 7,228,183 B2 | 6/2007 | Sun et al. |
| 7,236,821 B2 | 6/2007 | Cates et al. |
| 7,236,829 B1 | 6/2007 | Farazi et al. |
| 7,254,448 B2 | 8/2007 | Almendinger et al. |
| 7,260,436 B2 | 8/2007 | Kilgore et al. |
| 7,270,669 B1 | 9/2007 | Sra |
| 7,272,448 B1 | 9/2007 | Morgan et al. |
| 7,277,755 B1 | 10/2007 | Falkenberg et al. |
| 7,280,872 B1 | 10/2007 | Mosesov et al. |
| 7,288,096 B2 | 10/2007 | Chin |
| 7,289,847 B1 | 10/2007 | Gill et al. |
| 7,289,852 B2 | 10/2007 | Helfinstine et al. |
| 7,289,853 B1 | 10/2007 | Campbell et al. |
| 7,289,855 B2 | 10/2007 | Nghiem et al. |
| 7,302,294 B2 | 11/2007 | Kamath et al. |
| 7,305,266 B1 | 12/2007 | Kroll |
| 7,306,593 B2 | 12/2007 | Keidar et al. |
| 7,310,556 B2 | 12/2007 | Bulkes |
| 7,319,905 B1 | 1/2008 | Morgan et al. |
| 7,333,853 B2 | 2/2008 | Mazar et al. |
| 7,336,994 B2 | 2/2008 | Hettrick et al. |
| 7,347,819 B2 | 3/2008 | Lebel et al. |
| 7,366,572 B2 | 4/2008 | Heruth et al. |
| 7,373,207 B2 | 5/2008 | Lattouf |
| 7,384,403 B2 | 6/2008 | Sherman |
| 7,386,342 B1 | 6/2008 | Falkenberg et al. |
| 7,392,090 B2 | 6/2008 | Sweeney et al. |
| 7,406,105 B2 | 7/2008 | DelMain et al. |
| 7,406,349 B2 | 7/2008 | Seeberger et al. |
| 7,410,497 B2 | 8/2008 | Hastings et al. |
| 7,425,200 B2 | 9/2008 | Brockway et al. |
| 7,433,739 B1 | 10/2008 | Salys et al. |
| 7,496,409 B2 | 2/2009 | Greenhut et al. |
| 7,496,410 B2 | 2/2009 | Heil |
| 7,502,652 B2 | 3/2009 | Gaunt et al. |
| 7,512,448 B2 | 3/2009 | Malick et al. |
| 7,515,969 B2 | 4/2009 | Tockman et al. |
| 7,520,858 B2 | 4/2009 | Ofek et al. |
| 7,526,342 B2 | 4/2009 | Chin et al. |
| 7,529,589 B2 | 5/2009 | Williams et al. |
| 7,532,933 B2 | 5/2009 | Hastings et al. |
| 7,536,218 B2 | 5/2009 | Govari et al. |
| 7,536,222 B2 | 5/2009 | Bardy et al. |
| 7,536,224 B2 | 5/2009 | Ritscher et al. |
| 7,539,541 B2 | 5/2009 | Quiles et al. |
| 7,544,197 B2 | 6/2009 | Kelsch et al. |
| 7,558,631 B2 | 7/2009 | Cowan et al. |
| 7,565,195 B1 | 7/2009 | Kroll et al. |
| 7,584,002 B2 | 9/2009 | Burnes et al. |
| 7,590,455 B2 | 9/2009 | Heruth et al. |
| 7,591,816 B2 | 9/2009 | Wang et al. |
| 7,606,621 B2 | 10/2009 | Bnsken et al. |
| 7,610,088 B2 | 10/2009 | Chinchoy |
| 7,610,092 B2 | 10/2009 | Cowan et al. |
| 7,610,099 B2 | 10/2009 | Almendinger et al. |
| 7,610,104 B2 | 10/2009 | Kaplan et al. |
| 7,616,991 B2 | 11/2009 | Mann et al. |
| 7,617,001 B2 | 11/2009 | Penner et al. |
| 7,617,007 B2 | 11/2009 | Williams et al. |
| 7,630,767 B1 | 12/2009 | Poore et al. |
| 7,634,313 B1 | 12/2009 | Kroll et al. |
| 7,637,867 B2 | 12/2009 | Zdeblick |
| 7,640,060 B2 | 12/2009 | Zdeblick |
| 7,647,109 B2 | 1/2010 | Hastings et al. |
| 7,650,186 B2 | 1/2010 | Hastings et al. |
| 7,657,311 B2 | 2/2010 | Bardy et al. |
| 7,662,151 B2 | 2/2010 | Crompton, Jr. et al. |
| 7,668,596 B2 | 2/2010 | Arx et al. |
| 7,682,316 B2 | 3/2010 | Anderson et al. |
| 7,691,047 B2 | 4/2010 | Ferrari |
| 7,702,392 B2 | 4/2010 | Echt et al. |
| 7,713,194 B2 | 5/2010 | Zdeblick |
| 7,713,195 B2 | 5/2010 | Zdeblick |
| 7,722,601 B2 | 5/2010 | Wham et al. |
| 7,729,783 B2 | 6/2010 | Michels et al. |
| 7,734,333 B2 | 6/2010 | Ghanem et al. |
| 7,734,343 B2 | 6/2010 | Ransbury et al. |
| 7,738,958 B2 | 6/2010 | Zdeblick et al. |
| 7,738,964 B2 | 6/2010 | Arx et al. |
| 7,742,812 B2 | 6/2010 | Ghanem et al. |
| 7,742,816 B2 | 6/2010 | Masoud et al. |
| 7,742,822 B2 | 6/2010 | Masoud et al. |
| 7,743,151 B2 | 6/2010 | Vallapureddy et al. |
| 7,747,335 B2 | 6/2010 | Williams |
| 7,751,881 B2 | 7/2010 | Cowan et al. |
| 7,758,521 B2 | 7/2010 | Morris et al. |
| 7,761,150 B2 | 7/2010 | Ghanem et al. |
| 7,761,164 B2 | 7/2010 | Verhoef et al. |
| 7,765,001 B2 | 7/2010 | Echt et al. |
| 7,769,452 B2 | 8/2010 | Ghanem et al. |
| 7,783,362 B2 | 8/2010 | Whitehurst et al. |
| 7,792,588 B2 | 9/2010 | Harding |
| 7,797,059 B1 | 9/2010 | Bornzin et al. |

(56) References Cited

U.S. PATENT DOCUMENTS

| | | |
|---|---|---|
| 7,801,596 B2 | 9/2010 | Fischell et al. |
| 7,809,438 B2 | 10/2010 | Echt et al. |
| 7,819,870 B2 | 10/2010 | Thao |
| 7,823,467 B2 | 11/2010 | Taya et al. |
| 7,840,281 B2 | 11/2010 | Kveen et al. |
| 7,842,031 B2 | 11/2010 | Abboud et al. |
| 7,844,331 B2 | 11/2010 | Li et al. |
| 7,844,348 B2 | 11/2010 | Swoyer et al. |
| 7,846,088 B2 | 12/2010 | Ness |
| 7,848,787 B2 | 12/2010 | Osadchy |
| 7,848,815 B2 | 12/2010 | Brisken et al. |
| 7,848,822 B2 | 12/2010 | Zhang et al. |
| 7,848,823 B2 | 12/2010 | Drasler et al. |
| 7,860,455 B2 | 12/2010 | Fukumoto et al. |
| 7,871,433 B2 | 1/2011 | Lattouf |
| 7,877,136 B1 | 1/2011 | Moffitt et al. |
| 7,877,142 B2 | 1/2011 | Moaddeb et al. |
| 7,881,786 B2 | 2/2011 | Jackson |
| 7,881,798 B2 | 2/2011 | Miesel et al. |
| 7,881,810 B1 | 2/2011 | Chitre et al. |
| 7,883,508 B2 | 2/2011 | Thao et al. |
| 7,890,173 B2 | 2/2011 | Brisken et al. |
| 7,890,181 B2 | 2/2011 | Denzene et al. |
| 7,890,192 B1 | 2/2011 | Kelsch et al. |
| 7,894,885 B2 | 2/2011 | Bartal et al. |
| 7,894,894 B2 | 2/2011 | Stadler et al. |
| 7,894,907 B2 | 2/2011 | Cowan et al. |
| 7,894,910 B2 | 2/2011 | Cowan et al. |
| 7,894,915 B1 | 2/2011 | Chitre et al. |
| 7,899,537 B1 | 3/2011 | Kroll et al. |
| 7,899,541 B2 | 3/2011 | Cowan et al. |
| 7,899,542 B2 | 3/2011 | Cowan et al. |
| 7,899,554 B2 | 3/2011 | Williams et al. |
| 7,901,360 B1 | 3/2011 | Yang et al. |
| 7,904,170 B2 | 3/2011 | Harding |
| 7,907,993 B2 | 3/2011 | Ghanem et al. |
| 7,914,525 B2 | 3/2011 | Abboud et al. |
| 7,920,928 B1 | 4/2011 | Yang et al. |
| 7,925,343 B1 | 4/2011 | Min et al. |
| 7,930,022 B2 | 4/2011 | Zhang et al. |
| 7,930,040 B1 | 4/2011 | Kelsch et al. |
| 7,937,135 B2 | 5/2011 | Ghanem et al. |
| 7,937,148 B2 | 5/2011 | Jacobson |
| 7,937,161 B2 | 5/2011 | Hastings et al. |
| 7,941,214 B2 | 5/2011 | Kleckner et al. |
| 7,945,333 B2 | 5/2011 | Jacobson |
| 7,946,997 B2 | 5/2011 | Hübinette |
| 7,948,148 B2 | 5/2011 | Porat et al. |
| 7,949,404 B2 | 5/2011 | Hill |
| 7,949,405 B2 | 5/2011 | Feher |
| 7,953,486 B2 | 5/2011 | Daum et al. |
| 7,953,493 B2 | 5/2011 | Fowler et al. |
| 7,955,326 B2 | 6/2011 | Paul et al. |
| 7,962,202 B2 | 6/2011 | Bhunia |
| 7,974,702 B1 | 7/2011 | Fain et al. |
| 7,976,541 B2 | 7/2011 | McGee et al. |
| 7,979,136 B2 | 7/2011 | Young et al. |
| 7,983,753 B2 | 7/2011 | Severin |
| 7,984,659 B2 | 7/2011 | Fujimoto et al. |
| 7,991,467 B2 | 8/2011 | Markowitz et al. |
| 7,991,471 B2 | 8/2011 | Ghanem et al. |
| 7,996,087 B2 | 8/2011 | Cowan et al. |
| 8,000,791 B2 | 8/2011 | Sunagawa et al. |
| 8,000,807 B2 | 8/2011 | Morris et al. |
| 8,001,975 B2 | 8/2011 | DiSilvestro et al. |
| 8,002,700 B2 | 8/2011 | Ferek-Petric et al. |
| 8,010,209 B2 | 8/2011 | Jacobson |
| 8,012,150 B2 | 9/2011 | Wham et al. |
| 8,019,419 B1 | 9/2011 | Panescu et al. |
| 8,019,434 B2 | 9/2011 | Quiles et al. |
| 8,021,361 B2 | 9/2011 | Paul et al. |
| 8,027,727 B2 | 9/2011 | Freeberg |
| 8,027,729 B2 | 9/2011 | Sunagawa et al. |
| 8,032,219 B2 | 10/2011 | Neumann et al. |
| 8,034,049 B2 | 10/2011 | Odom et al. |
| 8,036,743 B2 | 10/2011 | Savage et al. |
| 8,038,693 B2 | 10/2011 | Allen |
| 8,046,079 B2 | 10/2011 | Bange et al. |
| 8,046,080 B2 | 10/2011 | Arx et al. |
| 8,048,063 B2 | 11/2011 | Aeby et al. |
| 8,048,069 B2 | 11/2011 | Skwarek et al. |
| 8,050,297 B2 | 11/2011 | DelMain et al. |
| 8,050,759 B2 | 11/2011 | Stegemann et al. |
| 8,050,774 B2 | 11/2011 | Kveen et al. |
| 8,052,621 B2 | 11/2011 | Wallace et al. |
| 8,055,345 B2 | 11/2011 | Li et al. |
| 8,055,350 B2 | 11/2011 | Roberts |
| 8,060,212 B1 | 11/2011 | Rios et al. |
| 8,065,018 B2 | 11/2011 | Haubrich et al. |
| 8,073,542 B2 | 12/2011 | Doerr |
| 8,075,498 B2 | 12/2011 | Leo et al. |
| 8,078,278 B2 | 12/2011 | Penner |
| 8,078,283 B2 | 12/2011 | Cowan et al. |
| 8,080,008 B2 | 12/2011 | Wham et al. |
| 8,083,691 B2 | 12/2011 | Goldenberg et al. |
| 8,092,397 B2 | 1/2012 | Wallace et al. |
| 8,095,123 B2 | 1/2012 | Gray |
| 8,102,789 B2 | 1/2012 | Rosar et al. |
| 8,103,338 B2 | 1/2012 | Harlev et al. |
| 8,103,359 B2 | 1/2012 | Reddy |
| 8,103,361 B2 | 1/2012 | Moser |
| 8,112,148 B2 | 2/2012 | Giftakis et al. |
| 8,114,021 B2 | 2/2012 | Robertson et al. |
| 8,118,809 B2 | 2/2012 | Paul et al. |
| 8,121,680 B2 | 2/2012 | Falkenberg et al. |
| 8,123,684 B2 | 2/2012 | Zdeblick |
| 8,126,545 B2 | 2/2012 | Flach et al. |
| 8,131,334 B2 | 3/2012 | Lu et al. |
| 8,140,161 B2 | 3/2012 | Willerton et al. |
| 8,150,521 B2 | 4/2012 | Crowley et al. |
| 8,152,802 B2 | 4/2012 | Podhajsky et al. |
| 8,157,789 B2 | 4/2012 | Leo et al. |
| 8,157,848 B2 | 4/2012 | Zhang et al. |
| 8,160,672 B2 | 4/2012 | Kim et al. |
| 8,160,690 B2 | 4/2012 | Wilfley et al. |
| 8,160,702 B2 | 4/2012 | Mann et al. |
| 8,160,704 B2 | 4/2012 | Freeberg |
| 8,162,932 B2 | 4/2012 | Podhajsky et al. |
| 8,162,935 B2 | 4/2012 | Paul et al. |
| 8,165,694 B2 | 4/2012 | Carbanaru et al. |
| 8,167,875 B2 | 5/2012 | Podhajsky et al. |
| 8,175,715 B1 | 5/2012 | Cox |
| 8,180,451 B2 | 5/2012 | Hickman et al. |
| 8,182,433 B2 | 5/2012 | Leo et al. |
| 8,185,213 B2 | 5/2012 | Kveen et al. |
| 8,187,161 B2 | 5/2012 | Li et al. |
| 8,187,267 B2 | 5/2012 | Pappone et al. |
| 8,195,293 B2 | 6/2012 | Limousin et al. |
| 8,204,595 B2 | 6/2012 | Pianca et al. |
| 8,204,605 B2 | 6/2012 | Hastings et al. |
| 8,206,385 B2 | 6/2012 | Stangenes et al. |
| 8,209,014 B2 | 6/2012 | Doerr |
| 8,211,100 B2 | 7/2012 | Podhajsky et al. |
| 8,211,102 B2 | 7/2012 | Paul et al. |
| 8,214,043 B2 | 7/2012 | Matos |
| 8,224,244 B2 | 7/2012 | Kim et al. |
| 8,226,580 B2 | 7/2012 | Govari et al. |
| 8,226,648 B2 | 7/2012 | Paul et al. |
| 8,229,556 B2 | 7/2012 | Li |
| 8,233,985 B2 | 7/2012 | Bulkes et al. |
| 8,262,578 B1 | 9/2012 | Bharmi et al. |
| 8,262,652 B2 | 9/2012 | Podhajsky |
| 8,265,745 B2 | 9/2012 | Hauck et al. |
| 8,265,748 B2 | 9/2012 | Liu et al. |
| 8,265,757 B2 | 9/2012 | Mass et al. |
| 8,267,926 B2 | 9/2012 | Paul et al. |
| 8,267,929 B2 | 9/2012 | Wham et al. |
| 8,277,441 B2 | 10/2012 | Porat et al. |
| 8,280,521 B2 | 10/2012 | Haubrich et al. |
| 8,285,387 B2 | 10/2012 | Utsi et al. |
| 8,286,510 B2 | 10/2012 | Meiss et al. |
| 8,290,578 B2 | 10/2012 | Schneider |
| 8,290,598 B2 | 10/2012 | Boon et al. |
| 8,290,600 B2 | 10/2012 | Hastings et al. |

(56) References Cited

U.S. PATENT DOCUMENTS

| | | |
|---|---|---|
| 8,292,882 B2 | 10/2012 | Danek et al. |
| 8,295,939 B2 | 10/2012 | Jacobson |
| 8,298,223 B2 | 10/2012 | Wham et al. |
| 8,298,224 B2 | 10/2012 | Danek et al. |
| 8,298,227 B2 | 10/2012 | Leo et al. |
| 8,301,254 B2 | 10/2012 | Mosesov et al. |
| 8,312,779 B2 | 11/2012 | Meiss et al. |
| 8,315,701 B2 | 11/2012 | Cowan et al. |
| 8,315,708 B2 | 11/2012 | Berthelsdorf et al. |
| 8,316,725 B2 | 11/2012 | Wade |
| 8,317,783 B2 | 11/2012 | Cao et al. |
| 8,321,021 B2 | 11/2012 | Kisker et al. |
| 8,321,036 B2 | 11/2012 | Brockway et al. |
| 8,327,715 B2 | 12/2012 | Bradley et al. |
| 8,332,036 B2 | 12/2012 | Hastings et al. |
| 8,333,103 B2 | 12/2012 | Bonyak et al. |
| 8,333,759 B2 | 12/2012 | Podhajsky |
| 8,335,563 B2 | 12/2012 | Stessman |
| 8,335,568 B2 | 12/2012 | Heruth et al. |
| 8,340,750 B2 | 12/2012 | Prakash et al. |
| 8,340,780 B2 | 12/2012 | Hastings et al. |
| 8,347,738 B2 | 1/2013 | Tung et al. |
| 8,352,025 B2 | 1/2013 | Jacobson |
| 8,352,028 B2 | 1/2013 | Wenger |
| 8,352,038 B2 | 1/2013 | Mao et al. |
| 8,357,152 B2 | 1/2013 | Govari et al. |
| 8,359,082 B2 | 1/2013 | Selkee |
| 8,359,098 B2 | 1/2013 | Lund et al. |
| 8,364,261 B2 | 1/2013 | Stubbs et al. |
| 8,364,276 B2 | 1/2013 | Willis |
| 8,369,921 B2 | 2/2013 | Tegg et al. |
| 8,369,922 B2 | 2/2013 | Paul et al. |
| 8,369,959 B2 | 2/2013 | Meskens |
| 8,369,962 B2 | 2/2013 | Abrahamson |
| 8,372,019 B2 | 2/2013 | Goldenberg et al. |
| 8,374,670 B2 | 2/2013 | Selkee |
| 8,374,819 B2 | 2/2013 | Govari et al. |
| 8,380,276 B2 | 2/2013 | Schultz |
| 8,380,320 B2 | 2/2013 | Spital |
| 8,382,689 B2 | 2/2013 | Sliwa et al. |
| 8,386,051 B2 | 2/2013 | Rys |
| 8,388,556 B2 | 3/2013 | Wallace et al. |
| 8,391,981 B2 | 3/2013 | Mosesov |
| 8,391,990 B2 | 3/2013 | Smith et al. |
| 8,403,925 B2 | 3/2013 | Miller et al. |
| 8,406,866 B2 | 3/2013 | Deno et al. |
| 8,406,874 B2 | 3/2013 | Liu et al. |
| 8,406,879 B2 | 3/2013 | Shuros et al. |
| 8,406,886 B2 | 3/2013 | Gaunt et al. |
| 8,412,317 B2 | 4/2013 | Mazar |
| 8,412,352 B2 | 4/2013 | Griswold et al. |
| 8,417,340 B2 | 4/2013 | Goossen |
| 8,417,341 B2 | 4/2013 | Freeberg |
| 8,417,355 B2 | 4/2013 | Zhang et al. |
| 8,423,149 B2 | 4/2013 | Hennig |
| 8,428,722 B2 | 4/2013 | Verhoef et al. |
| 8,433,402 B2 | 4/2013 | Ruben et al. |
| 8,433,409 B2 | 4/2013 | Johnson et al. |
| 8,433,420 B2 | 4/2013 | Bange et al. |
| 8,435,232 B2 | 5/2013 | Aeby et al. |
| 8,437,832 B2 | 5/2013 | Govari et al. |
| 8,444,549 B2 | 5/2013 | Viola et al. |
| 8,447,412 B2 | 5/2013 | Molin et al. |
| 8,449,535 B2 | 5/2013 | Deno et al. |
| 8,452,413 B2 | 5/2013 | Young et al. |
| 8,454,589 B2 | 6/2013 | Deno et al. |
| 8,457,740 B2 | 6/2013 | Osche |
| 8,457,742 B2 | 6/2013 | Jacobson |
| 8,457,744 B2 | 6/2013 | Janzig et al. |
| 8,457,761 B2 | 6/2013 | Wariar |
| 8,460,285 B2 | 6/2013 | Wang et al. |
| 8,478,407 B2 | 7/2013 | Demmer et al. |
| 8,478,408 B2 | 7/2013 | Hastings et al. |
| 8,478,431 B2 | 7/2013 | Griswold et al. |
| 8,480,669 B2 | 7/2013 | Pappone et al. |
| 8,486,061 B2 | 7/2013 | Podhajsky |
| 8,489,184 B2 | 7/2013 | Wilfley et al. |
| 8,494,632 B2 | 7/2013 | Sun et al. |
| 8,500,731 B2 | 8/2013 | Byrd et al. |
| 8,504,132 B2 | 8/2013 | Friedman et al. |
| 8,504,156 B2 | 8/2013 | Bonner et al. |
| 8,509,910 B2 | 8/2013 | Sowder et al. |
| 8,515,559 B2 | 8/2013 | Roberts et al. |
| 8,521,262 B2 | 8/2013 | Webler |
| 8,521,462 B2 | 8/2013 | Govari et al. |
| 8,525,340 B2 | 9/2013 | Eckhardt et al. |
| 8,527,068 B2 | 9/2013 | Ostroff |
| 8,529,476 B2 | 9/2013 | Govari |
| 8,532,738 B2 | 9/2013 | Zino |
| 8,532,746 B2 | 9/2013 | Gelbart et al. |
| 8,532,790 B2 | 9/2013 | Griswold |
| 8,535,308 B2 | 9/2013 | Govari et al. |
| 8,535,340 B2 | 9/2013 | Allen |
| 8,538,526 B2 | 9/2013 | Stahmann et al. |
| 8,541,131 B2 | 9/2013 | Lund et al. |
| 8,543,205 B2 | 9/2013 | Ostroff |
| 8,545,408 B2 | 10/2013 | Sliwa et al. |
| 8,547,248 B2 | 10/2013 | Zdeblick et al. |
| 8,548,605 B2 | 10/2013 | Ollivier |
| 8,554,333 B2 | 10/2013 | Wu et al. |
| 8,565,882 B2 | 10/2013 | Matos |
| 8,565,897 B2 | 10/2013 | Regnier et al. |
| 8,567,265 B2 | 10/2013 | Aeby et al. |
| 8,568,404 B2 | 10/2013 | Brannan |
| 8,571,647 B2 | 10/2013 | Harlev et al. |
| 8,571,678 B2 | 10/2013 | Wang |
| 8,577,327 B2 | 11/2013 | Makdissi et al. |
| 8,577,447 B2 | 11/2013 | Tegg et al. |
| 8,588,926 B2 | 11/2013 | Moore et al. |
| 8,602,642 B2 | 12/2013 | Klewer |
| 8,603,084 B2 | 12/2013 | Fish et al. |
| 8,603,085 B2 | 12/2013 | Jimenez |
| 8,612,002 B2 | 12/2013 | Faltys et al. |
| 8,615,310 B2 | 12/2013 | Khairkhahan et al. |
| 8,617,152 B2 | 12/2013 | Werneth et al. |
| 8,622,935 B1 | 1/2014 | Leo |
| 8,626,280 B2 | 1/2014 | Allavatam et al. |
| 8,626,294 B2 | 1/2014 | Sheldon et al. |
| 8,628,473 B2 | 1/2014 | Sliwa et al. |
| 8,631,713 B2 | 1/2014 | Fujimoto et al. |
| 8,634,908 B2 | 1/2014 | Cowan |
| 8,634,912 B2 | 1/2014 | Bornzin et al. |
| 8,634,919 B1 | 1/2014 | Hou et al. |
| 8,639,335 B2 | 1/2014 | Peichel et al. |
| 8,641,705 B2 | 2/2014 | Leo et al. |
| 8,644,934 B2 | 2/2014 | Hastings et al. |
| 8,644,950 B2 | 2/2014 | Hauck |
| 8,649,859 B2 | 2/2014 | Smith et al. |
| 8,663,214 B2 | 3/2014 | Weinberg et al. |
| 8,668,686 B2 | 3/2014 | Govari et al. |
| 8,670,842 B1 | 3/2014 | Bornzin et al. |
| 8,672,936 B2 | 3/2014 | Thao et al. |
| 8,676,319 B2 | 3/2014 | Knoll |
| 8,676,335 B2 | 3/2014 | Katoozi et al. |
| 8,679,109 B2 | 3/2014 | Paul et al. |
| 8,696,656 B2 | 4/2014 | Abboud et al. |
| 8,700,173 B2 | 4/2014 | Edlund |
| 8,700,181 B2 | 4/2014 | Bornzin et al. |
| 8,702,688 B2 | 4/2014 | Melsky |
| 8,702,690 B2 | 4/2014 | Paul et al. |
| 8,705,599 B2 | 4/2014 | Molin et al. |
| 8,718,766 B2 | 5/2014 | Wahlberg |
| 8,718,773 B2 | 5/2014 | Willis et al. |
| 8,725,233 B2 | 5/2014 | Nagano et al. |
| 8,725,260 B2 | 5/2014 | Shuros et al. |
| 8,728,077 B2 | 5/2014 | Paul et al. |
| 8,738,133 B2 | 5/2014 | Shuros et al. |
| 8,738,147 B2 | 5/2014 | Hastings et al. |
| 8,744,555 B2 | 6/2014 | Allavatam et al. |
| 8,744,572 B1 | 6/2014 | Greenhut et al. |
| 8,747,314 B2 | 6/2014 | Stahmann et al. |
| 8,755,860 B2 | 6/2014 | Paul et al. |
| 8,755,884 B2 | 6/2014 | Demmer et al. |
| 8,758,365 B2 | 6/2014 | Bonner et al. |

(56) References Cited

U.S. PATENT DOCUMENTS

| | | |
|---|---|---|
| 8,768,483 B2 | 7/2014 | Schmitt et al. |
| 8,774,572 B2 | 7/2014 | Hamamoto |
| 8,781,605 B2 | 7/2014 | Bornzin et al. |
| 8,788,035 B2 | 7/2014 | Jacobson |
| 8,788,053 B2 | 7/2014 | Jacobson |
| 8,798,740 B2 | 8/2014 | Samade et al. |
| 8,798,745 B2 | 8/2014 | Jacobson |
| 8,798,762 B2 | 8/2014 | Fain et al. |
| 8,798,770 B2 | 8/2014 | Reddy |
| 8,805,505 B1 | 8/2014 | Roberts |
| 8,805,528 B2 | 8/2014 | Corndorf |
| 8,812,109 B2 | 8/2014 | Blomqvist et al. |
| 8,818,504 B2 | 8/2014 | Bodner et al. |
| 8,827,913 B2 | 9/2014 | Havel et al. |
| 8,831,747 B1 | 9/2014 | Min et al. |
| 8,855,789 B2 | 10/2014 | Jacobson |
| 8,868,186 B2 | 10/2014 | Kroll |
| 8,886,339 B2 | 11/2014 | Faltys et al. |
| 8,903,473 B2 | 12/2014 | Rogers et al. |
| 8,903,500 B2 | 12/2014 | Smith et al. |
| 8,903,513 B2 | 12/2014 | Ollivier |
| 8,909,336 B2 | 12/2014 | Navarro-Paredes et al. |
| 8,914,131 B2 | 12/2014 | Bornzin et al. |
| 8,923,795 B2 | 12/2014 | Makdissi et al. |
| 8,923,963 B2 | 12/2014 | Bonner et al. |
| 8,938,300 B2 | 1/2015 | Rosero |
| 8,942,806 B2 | 1/2015 | Sheldon et al. |
| 8,958,892 B2 | 2/2015 | Khairkhahan et al. |
| 8,977,358 B2 | 3/2015 | Ewert et al. |
| 8,989,873 B2 | 3/2015 | Locsin |
| 8,996,109 B2 | 3/2015 | Karst et al. |
| 9,002,467 B2 | 4/2015 | Smith et al. |
| 9,008,776 B2 | 4/2015 | Cowan et al. |
| 9,008,777 B2 | 4/2015 | Dianaty et al. |
| 9,014,818 B2 | 4/2015 | Deterre et al. |
| 9,017,341 B2 | 4/2015 | Bornzin et al. |
| 9,020,611 B2 | 4/2015 | Khairkhahan et al. |
| 9,037,262 B2 | 5/2015 | Regnier et al. |
| 9,042,984 B2 | 5/2015 | Demmer et al. |
| 9,072,911 B2 | 7/2015 | Hastings et al. |
| 9,072,913 B2 | 7/2015 | Jacobson |
| 9,155,882 B2 | 10/2015 | Grubac et al. |
| 9,168,372 B2 | 10/2015 | Fain |
| 9,168,380 B1 | 10/2015 | Greenhut et al. |
| 9,168,383 B2 | 10/2015 | Jacobson et al. |
| 9,180,285 B2 | 11/2015 | Moore et al. |
| 9,192,774 B2 | 11/2015 | Jacobson |
| 9,205,225 B2 | 12/2015 | Khairkhahan et al. |
| 9,216,285 B1 | 12/2015 | Boling et al. |
| 9,216,293 B2 | 12/2015 | Berthiaume et al. |
| 9,216,298 B2 | 12/2015 | Jacobson |
| 9,227,077 B2 | 1/2016 | Jacobson |
| 9,238,145 B2 | 1/2016 | Wenzel et al. |
| 9,242,102 B2 | 1/2016 | Khairkhahan et al. |
| 9,242,113 B2 | 1/2016 | Smith et al. |
| 9,248,300 B2 | 2/2016 | Rys et al. |
| 9,265,436 B2 | 2/2016 | Min et al. |
| 9,265,962 B2 | 2/2016 | Dianaty et al. |
| 9,272,155 B2 | 3/2016 | Ostroff |
| 9,278,218 B2 | 3/2016 | Karst et al. |
| 9,278,229 B1 | 3/2016 | Reinke et al. |
| 9,283,381 B2 | 3/2016 | Grubac et al. |
| 9,283,382 B2 | 3/2016 | Berthiaume et al. |
| 9,289,612 B1 | 3/2016 | Sambelashvili et al. |
| 9,302,115 B2 | 4/2016 | Molin et al. |
| 9,333,364 B2 | 5/2016 | Echt et al. |
| 9,358,387 B2 | 6/2016 | Suwito et al. |
| 9,358,400 B2 | 6/2016 | Jacobson |
| 9,364,675 B2 | 6/2016 | Deterre et al. |
| 9,370,663 B2 | 6/2016 | Moulder |
| 9,375,580 B2 | 6/2016 | Bonner et al. |
| 9,375,581 B2 | 6/2016 | Baru et al. |
| 9,381,365 B2 | 7/2016 | Kibler et al. |
| 9,393,424 B2 | 7/2016 | Demmer et al. |
| 9,393,436 B2 | 7/2016 | Doerr |
| 9,399,139 B2 | 7/2016 | Demmer et al. |
| 9,399,140 B2 | 7/2016 | Cho et al. |
| 9,409,033 B2 | 8/2016 | Jacobson |
| 9,427,594 B1 | 8/2016 | Bornzin et al. |
| 9,433,368 B2 | 9/2016 | Stahmann et al. |
| 9,433,780 B2 | 9/2016 | Régnier et al. |
| 9,457,193 B2 | 10/2016 | Klimovitch et al. |
| 9,492,668 B2 | 11/2016 | Sheldon et al. |
| 9,492,669 B2 | 11/2016 | Demmer et al. |
| 9,492,674 B2 | 11/2016 | Schmidt et al. |
| 9,492,677 B2 | 11/2016 | Greenhut et al. |
| 9,511,233 B2 | 12/2016 | Sambelashvili |
| 9,511,236 B2 | 12/2016 | Varady et al. |
| 9,511,237 B2 | 12/2016 | Deterre et al. |
| 9,522,276 B2 | 12/2016 | Shen et al. |
| 9,522,280 B2 | 12/2016 | Fishier et al. |
| 9,526,522 B2 | 12/2016 | Wood et al. |
| 9,526,891 B2 | 12/2016 | Eggen et al. |
| 9,526,909 B2 | 12/2016 | Stahmann et al. |
| 9,533,163 B2 | 1/2017 | Klimovitch et al. |
| 9,561,382 B2 | 2/2017 | Persson et al. |
| 9,566,012 B2 | 2/2017 | Greenhut et al. |
| 9,636,511 B2 | 5/2017 | Carney et al. |
| 9,669,223 B2 | 6/2017 | Auricchio et al. |
| 9,687,654 B2 | 6/2017 | Sheldon et al. |
| 9,687,655 B2 | 6/2017 | Pertijs et al. |
| 9,687,659 B2 | 6/2017 | Von Arx et al. |
| 9,694,186 B2 | 7/2017 | Carney et al. |
| 9,782,594 B2 | 10/2017 | Stahmann et al. |
| 9,782,601 B2 | 10/2017 | Ludwig |
| 9,789,317 B2 | 10/2017 | Greenhut et al. |
| 9,789,319 B2 | 10/2017 | Sambelashvili |
| 9,808,617 B2 | 11/2017 | Ostroff et al. |
| 9,808,628 B2 | 11/2017 | Sheldon et al. |
| 9,808,631 B2 | 11/2017 | Maile et al. |
| 9,808,632 B2 | 11/2017 | Reinke et al. |
| 9,808,633 B2 | 11/2017 | Bonner et al. |
| 9,808,637 B2 | 11/2017 | Sharma et al. |
| 9,855,414 B2 | 1/2018 | Marshall et al. |
| 9,855,430 B2 | 1/2018 | Ghosh et al. |
| 9,855,435 B2 | 1/2018 | Sahabi et al. |
| 9,861,815 B2 | 1/2018 | Tran et al. |
| 2001/0034501 A1 | 10/2001 | Tom |
| 2002/0032470 A1 | 3/2002 | Linberg |
| 2002/0035376 A1 | 3/2002 | Bardy et al. |
| 2002/0035377 A1 | 3/2002 | Bardy et al. |
| 2002/0035378 A1 | 3/2002 | Bardy et al. |
| 2002/0035380 A1 | 3/2002 | Rissmann et al. |
| 2002/0035381 A1 | 3/2002 | Bardy et al. |
| 2002/0042629 A1 | 4/2002 | Bardy et al. |
| 2002/0042630 A1 | 4/2002 | Bardy et al. |
| 2002/0042634 A1 | 4/2002 | Bardy et al. |
| 2002/0049475 A1 | 4/2002 | Bardy et al. |
| 2002/0052636 A1 | 5/2002 | Bardy et al. |
| 2002/0068958 A1 | 6/2002 | Bardy et al. |
| 2002/0072773 A1 | 6/2002 | Bardy et al. |
| 2002/0082665 A1 | 6/2002 | Haller et al. |
| 2002/0091414 A1 | 7/2002 | Bardy et al. |
| 2002/0095196 A1 | 7/2002 | Linberg |
| 2002/0099423 A1 | 7/2002 | Berg et al. |
| 2002/0103510 A1 | 8/2002 | Bardy et al. |
| 2002/0107545 A1 | 8/2002 | Rissmann et al. |
| 2002/0107546 A1 | 8/2002 | Ostroff et al. |
| 2002/0107547 A1 | 8/2002 | Erlinger et al. |
| 2002/0107548 A1 | 8/2002 | Bardy et al. |
| 2002/0107549 A1 | 8/2002 | Bardy et al. |
| 2002/0107559 A1 | 8/2002 | Sanders et al. |
| 2002/0120299 A1 | 8/2002 | Ostroff et al. |
| 2002/0173830 A1 | 11/2002 | Starkweather et al. |
| 2002/0193846 A1 | 12/2002 | Pool et al. |
| 2003/0009203 A1 | 1/2003 | Lebel et al. |
| 2003/0028082 A1 | 2/2003 | Thompson |
| 2003/0040779 A1 | 2/2003 | Engmark et al. |
| 2003/0041866 A1 | 3/2003 | Linberg et al. |
| 2003/0045805 A1 | 3/2003 | Sheldon et al. |
| 2003/0088278 A1 | 5/2003 | Bardy et al. |
| 2003/0097153 A1 | 5/2003 | Bardy et al. |
| 2003/0105497 A1 | 6/2003 | Zhu et al. |
| 2003/0114908 A1 | 6/2003 | Flach |

(56) References Cited

U.S. PATENT DOCUMENTS

| | | |
|---|---|---|
| 2003/0144701 A1 | 7/2003 | Mehra et al. |
| 2003/0187460 A1 | 10/2003 | Chin et al. |
| 2003/0187461 A1 | 10/2003 | Chin |
| 2004/0024435 A1 | 2/2004 | Leckrone et al. |
| 2004/0068302 A1 | 4/2004 | Rodgers et al. |
| 2004/0087938 A1 | 5/2004 | Leckrone et al. |
| 2004/0088035 A1 | 5/2004 | Guenst et al. |
| 2004/0102830 A1 | 5/2004 | Williams |
| 2004/0127959 A1 | 7/2004 | Amundson et al. |
| 2004/0133242 A1 | 7/2004 | Chapman et al. |
| 2004/0147969 A1 | 7/2004 | Mann et al. |
| 2004/0147973 A1 | 7/2004 | Hauser |
| 2004/0167558 A1 | 8/2004 | Igo et al. |
| 2004/0167587 A1 | 8/2004 | Thompson |
| 2004/0172071 A1 | 9/2004 | Bardy et al. |
| 2004/0172077 A1 | 9/2004 | Chinchoy |
| 2004/0172104 A1 | 9/2004 | Berg et al. |
| 2004/0176817 A1 | 9/2004 | Wahlstrand et al. |
| 2004/0176818 A1 | 9/2004 | Wahlstrand et al. |
| 2004/0176830 A1 | 9/2004 | Fang |
| 2004/0186529 A1 | 9/2004 | Bardy et al. |
| 2004/0204673 A1 | 10/2004 | Flaherty |
| 2004/0210292 A1 | 10/2004 | Bardy et al. |
| 2004/0210293 A1 | 10/2004 | Bardy et al. |
| 2004/0210294 A1 | 10/2004 | Bardy et al. |
| 2004/0215308 A1 | 10/2004 | Bardy et al. |
| 2004/0220624 A1 | 11/2004 | Ritscher et al. |
| 2004/0220626 A1 | 11/2004 | Wagner |
| 2004/0220639 A1 | 11/2004 | Mulligan et al. |
| 2004/0249431 A1 | 12/2004 | Ransbury et al. |
| 2004/0260348 A1 | 12/2004 | Bakken et al. |
| 2004/0267303 A1 | 12/2004 | Guenst |
| 2005/0061320 A1 | 3/2005 | Lee et al. |
| 2005/0070962 A1 | 3/2005 | Echt et al. |
| 2005/0102003 A1 | 5/2005 | Grabek et al. |
| 2005/0149138 A1 | 7/2005 | Min et al. |
| 2005/0165466 A1 | 7/2005 | Morris et al. |
| 2005/0182465 A1 | 8/2005 | Ness |
| 2005/0203410 A1 | 9/2005 | Jenkins |
| 2005/0283208 A1 | 12/2005 | Arx et al. |
| 2005/0288743 A1 | 12/2005 | Ahn et al. |
| 2006/0042830 A1 | 3/2006 | Maghribi et al. |
| 2006/0052829 A1 | 3/2006 | Sun et al. |
| 2006/0052830 A1 | 3/2006 | Spinelli et al. |
| 2006/0064135 A1 | 3/2006 | Brockway |
| 2006/0064149 A1 | 3/2006 | Belacazar et al. |
| 2006/0085039 A1 | 4/2006 | Hastings et al. |
| 2006/0085041 A1 | 4/2006 | Hastings et al. |
| 2006/0085042 A1 | 4/2006 | Hastings et al. |
| 2006/0095078 A1 | 5/2006 | Tronnes |
| 2006/0106442 A1 | 5/2006 | Richardson et al. |
| 2006/0116746 A1 | 6/2006 | Chin |
| 2006/0135999 A1 | 6/2006 | Bodner et al. |
| 2006/0136004 A1 | 6/2006 | Cowan et al. |
| 2006/0161061 A1 | 7/2006 | Echt et al. |
| 2006/0200002 A1 | 9/2006 | Guenst |
| 2006/0200049 A1 | 9/2006 | Leo et al. |
| 2006/0206151 A1 | 9/2006 | Lu |
| 2006/0212079 A1 | 9/2006 | Routh et al. |
| 2006/0241701 A1 | 10/2006 | Markowitz et al. |
| 2006/0241705 A1 | 10/2006 | Neumann et al. |
| 2006/0247672 A1 | 11/2006 | Vidlund et al. |
| 2006/0259088 A1 | 11/2006 | Pastore et al. |
| 2006/0265018 A1 | 11/2006 | Smith et al. |
| 2006/0278248 A1 | 12/2006 | Viswanathan |
| 2007/0004979 A1 | 1/2007 | Wojciechowicz et al. |
| 2007/0016098 A1 | 1/2007 | Kim et al. |
| 2007/0027508 A1 | 2/2007 | Cowan |
| 2007/0060847 A1 | 3/2007 | Leo et al. |
| 2007/0062546 A1 | 3/2007 | Viswanathan et al. |
| 2007/0078490 A1 | 4/2007 | Cowan et al. |
| 2007/0088394 A1 | 4/2007 | Jacobson |
| 2007/0088396 A1 | 4/2007 | Jacobson |
| 2007/0088397 A1 | 4/2007 | Jacobson |
| 2007/0088398 A1 | 4/2007 | Jacobson |
| 2007/0088405 A1 | 4/2007 | Jacobson |
| 2007/0135882 A1 | 6/2007 | Drasler et al. |
| 2007/0135883 A1 | 6/2007 | Drasler et al. |
| 2007/0150037 A1 | 6/2007 | Hastings et al. |
| 2007/0150038 A1 | 6/2007 | Hastings et al. |
| 2007/0156190 A1 | 7/2007 | Cinbis |
| 2007/0181139 A1 | 8/2007 | Hauck |
| 2007/0219525 A1 | 9/2007 | Gelfand et al. |
| 2007/0219590 A1 | 9/2007 | Hastings et al. |
| 2007/0225545 A1 | 9/2007 | Ferrari |
| 2007/0233206 A1 | 10/2007 | Frikart et al. |
| 2007/0239244 A1 | 10/2007 | Morgan et al. |
| 2007/0255376 A1 | 11/2007 | Michels et al. |
| 2007/0276444 A1 | 11/2007 | Gelbart et al. |
| 2007/0293900 A1 | 12/2007 | Sheldon et al. |
| 2007/0293904 A1 | 12/2007 | Gelbart et al. |
| 2008/0004663 A1 | 1/2008 | Jorgenson |
| 2008/0021505 A1 | 1/2008 | Hastings et al. |
| 2008/0021519 A1 | 1/2008 | De Geest et al. |
| 2008/0021532 A1 | 1/2008 | Kveen et al. |
| 2008/0065183 A1 | 3/2008 | Whitehurst et al. |
| 2008/0065185 A1 | 3/2008 | Worley |
| 2008/0071318 A1 | 3/2008 | Brooke et al. |
| 2008/0109054 A1 | 5/2008 | Hastings et al. |
| 2008/0114256 A1* | 5/2008 | Zhang ............... A61B 5/11 600/488 |
| 2008/0119911 A1 | 5/2008 | Rosero |
| 2008/0130670 A1 | 6/2008 | Kim et al. |
| 2008/0154139 A1 | 6/2008 | Shuros et al. |
| 2008/0154322 A1 | 6/2008 | Jackson et al. |
| 2008/0161786 A1 | 7/2008 | Belhe et al. |
| 2008/0161796 A1 | 7/2008 | Cao et al. |
| 2008/0228234 A1 | 9/2008 | Stancer |
| 2008/0234771 A1 | 9/2008 | Chinchoy et al. |
| 2008/0243217 A1 | 10/2008 | Wildon |
| 2008/0269814 A1 | 10/2008 | Rosero |
| 2008/0269825 A1 | 10/2008 | Chinchoy et al. |
| 2008/0275465 A1 | 11/2008 | Paul et al. |
| 2008/0275518 A1 | 11/2008 | Ghanem et al. |
| 2008/0275519 A1 | 11/2008 | Ghanem et al. |
| 2008/0288039 A1 | 11/2008 | Reddy |
| 2008/0294208 A1 | 11/2008 | Willis et al. |
| 2008/0294210 A1 | 11/2008 | Rosero |
| 2008/0300589 A1 | 12/2008 | Paul et al. |
| 2008/0306359 A1 | 12/2008 | Zdeblick et al. |
| 2008/0312521 A1 | 12/2008 | Solomon |
| 2009/0012368 A1 | 1/2009 | Banik |
| 2009/0018599 A1 | 1/2009 | Hastings et al. |
| 2009/0024180 A1 | 1/2009 | Kisker et al. |
| 2009/0030477 A1 | 1/2009 | Jarrard |
| 2009/0036941 A1 | 2/2009 | Corbucci |
| 2009/0048646 A1 | 2/2009 | Katoozi et al. |
| 2009/0062895 A1 | 3/2009 | Stahmann et al. |
| 2009/0082755 A1 | 3/2009 | Milijasevic et al. |
| 2009/0082827 A1 | 3/2009 | Kveen |
| 2009/0082828 A1 | 3/2009 | Ostroff |
| 2009/0088813 A1 | 4/2009 | Brockway et al. |
| 2009/0131907 A1 | 5/2009 | Chin et al. |
| 2009/0135886 A1 | 5/2009 | Robertson et al. |
| 2009/0143835 A1 | 6/2009 | Pastore et al. |
| 2009/0171343 A1 | 7/2009 | Paul et al. |
| 2009/0171345 A1 | 7/2009 | Miller et al. |
| 2009/0171408 A1 | 7/2009 | Solem |
| 2009/0171414 A1 | 7/2009 | Kelly et al. |
| 2009/0177111 A1 | 7/2009 | Miller et al. |
| 2009/0204163 A1 | 8/2009 | Shuros et al. |
| 2009/0204170 A1 | 8/2009 | Hastings et al. |
| 2009/0210024 A1 | 8/2009 | Brooke |
| 2009/0216292 A1 | 8/2009 | Pless et al. |
| 2009/0234367 A1 | 9/2009 | Verma |
| 2009/0234407 A1 | 9/2009 | Hastings et al. |
| 2009/0234411 A1 | 9/2009 | Sambelashvili et al. |
| 2009/0266573 A1 | 10/2009 | Engmark et al. |
| 2009/0275827 A1 | 11/2009 | Aiken et al. |
| 2009/0275998 A1 | 11/2009 | Burnes et al. |
| 2009/0275999 A1 | 11/2009 | Burnes et al. |
| 2009/0299447 A1 | 12/2009 | Jensen et al. |
| 2010/0013668 A1 | 1/2010 | Kantervik |
| 2010/0016911 A1 | 1/2010 | Willis et al. |

(56) References Cited

U.S. PATENT DOCUMENTS

| | | |
|---|---|---|
| 2010/0023085 A1 | 1/2010 | Wu et al. |
| 2010/0030061 A1 | 2/2010 | Canfield et al. |
| 2010/0030327 A1 | 2/2010 | Chatel |
| 2010/0042108 A1 | 2/2010 | Hibino |
| 2010/0056871 A1 | 3/2010 | Govari et al. |
| 2010/0063375 A1 | 3/2010 | Kassab et al. |
| 2010/0063478 A1 | 3/2010 | Selkee |
| 2010/0063562 A1 | 3/2010 | Cowan et al. |
| 2010/0069733 A1 | 3/2010 | Kastelein et al. |
| 2010/0094163 A1 | 4/2010 | Deladi et al. |
| 2010/0094367 A1 | 4/2010 | Sen |
| 2010/0114209 A1 | 5/2010 | Krause et al. |
| 2010/0114214 A1 | 5/2010 | Morelli et al. |
| 2010/0125281 A1 | 5/2010 | Jacobson et al. |
| 2010/0168549 A1 | 7/2010 | Pappone |
| 2010/0168557 A1 | 7/2010 | Deno et al. |
| 2010/0168561 A1 | 7/2010 | Anderson |
| 2010/0168620 A1 | 7/2010 | Klimovitch et al. |
| 2010/0168761 A1 | 7/2010 | Kassab et al. |
| 2010/0168819 A1 | 7/2010 | Freeberg |
| 2010/0198288 A1 | 8/2010 | Ostroff |
| 2010/0198304 A1 | 8/2010 | Wang |
| 2010/0217367 A1 | 8/2010 | Belson |
| 2010/0228247 A1 | 9/2010 | Paul et al. |
| 2010/0228308 A1 | 9/2010 | Cowan et al. |
| 2010/0234906 A1 | 9/2010 | Koh |
| 2010/0234924 A1 | 9/2010 | Willis |
| 2010/0241117 A1 | 9/2010 | Paul et al. |
| 2010/0241185 A1 | 9/2010 | Mahapatra et al. |
| 2010/0249729 A1 | 9/2010 | Morris et al. |
| 2010/0286690 A1 | 11/2010 | Paul et al. |
| 2010/0286744 A1 | 11/2010 | Echt et al. |
| 2010/0292566 A1 | 11/2010 | Nagano et al. |
| 2010/0298823 A1 | 11/2010 | Cao et al. |
| 2010/0298826 A1 | 11/2010 | Leo et al. |
| 2010/0305429 A1 | 12/2010 | Shachar et al. |
| 2010/0312309 A1 | 12/2010 | Harding |
| 2011/0022045 A1 | 1/2011 | Cao et al. |
| 2011/0022113 A1 | 1/2011 | Zdeblick et al. |
| 2011/0066147 A1 | 3/2011 | He et al. |
| 2011/0071586 A1 | 3/2011 | Jacobson |
| 2011/0077708 A1 | 3/2011 | Ostroff |
| 2011/0087112 A1 | 4/2011 | Leo et al. |
| 2011/0112600 A1 | 5/2011 | Cowan et al. |
| 2011/0118588 A1 | 5/2011 | Komblau et al. |
| 2011/0118810 A1 | 5/2011 | Cowan et al. |
| 2011/0137153 A1 | 6/2011 | Govari et al. |
| 2011/0137187 A1 | 6/2011 | Yang et al. |
| 2011/0144524 A1 | 6/2011 | Fish et al. |
| 2011/0144633 A1 | 6/2011 | Govari |
| 2011/0144640 A1 | 6/2011 | Heinrich et al. |
| 2011/0144657 A1 | 6/2011 | Fish et al. |
| 2011/0144720 A1 | 6/2011 | Cowan et al. |
| 2011/0152854 A1 | 6/2011 | Govari et al. |
| 2011/0152856 A1 | 6/2011 | Govari et al. |
| 2011/0152970 A1 | 6/2011 | Jollota et al. |
| 2011/0160558 A1 | 6/2011 | Rassatt et al. |
| 2011/0160565 A1 | 6/2011 | Stubbs et al. |
| 2011/0160801 A1 | 6/2011 | Markowitz et al. |
| 2011/0160806 A1 | 6/2011 | Lyden et al. |
| 2011/0166620 A1 | 7/2011 | Cowan et al. |
| 2011/0166621 A1 | 7/2011 | Cowan et al. |
| 2011/0184491 A1 | 7/2011 | Kivi |
| 2011/0190835 A1 | 8/2011 | Brockway et al. |
| 2011/0208260 A1 | 8/2011 | Jacobson |
| 2011/0218587 A1 | 9/2011 | Jacobson |
| 2011/0230734 A1 | 9/2011 | Fain et al. |
| 2011/0237967 A1 | 9/2011 | Moore et al. |
| 2011/0245890 A1 | 10/2011 | Brisben et al. |
| 2011/0251660 A1 | 10/2011 | Griswold |
| 2011/0251662 A1 | 10/2011 | Griswold et al. |
| 2011/0270046 A1 | 11/2011 | Paul et al. |
| 2011/0270099 A1 | 11/2011 | Ruben et al. |
| 2011/0270339 A1 | 11/2011 | Murray, III et al. |
| 2011/0270340 A1 | 11/2011 | Pellegrini et al. |
| 2011/0276102 A1 | 11/2011 | Cohen |
| 2011/0282423 A1 | 11/2011 | Jacobson |
| 2011/0307207 A1 | 12/2011 | Govari et al. |
| 2011/0313280 A1 | 12/2011 | Govari et al. |
| 2012/0004527 A1 | 1/2012 | Thompson et al. |
| 2012/0029323 A1 | 2/2012 | Zhao |
| 2012/0029504 A1 | 2/2012 | Afonso et al. |
| 2012/0041508 A1 | 2/2012 | Rousso et al. |
| 2012/0059433 A1 | 3/2012 | Cowan et al. |
| 2012/0059436 A1 | 3/2012 | Fontaine et al. |
| 2012/0065500 A1 | 3/2012 | Rogers et al. |
| 2012/0078138 A1 | 3/2012 | Leo et al. |
| 2012/0078322 A1 | 3/2012 | Molin et al. |
| 2012/0089198 A1 | 4/2012 | Ostroff |
| 2012/0089358 A1 | 4/2012 | Ludwin et al. |
| 2012/0093245 A1 | 4/2012 | Makdissi et al. |
| 2012/0095521 A1 | 4/2012 | Hintz |
| 2012/0095539 A1 | 4/2012 | Khairkhahan et al. |
| 2012/0101540 A1 | 4/2012 | O'Brien et al. |
| 2012/0101553 A1 | 4/2012 | Reddy |
| 2012/0108988 A1 | 5/2012 | Ludwin et al. |
| 2012/0109148 A1 | 5/2012 | Bonner et al. |
| 2012/0109149 A1 | 5/2012 | Bonner et al. |
| 2012/0109236 A1 | 5/2012 | Jacobson et al. |
| 2012/0109259 A1 | 5/2012 | Bond et al. |
| 2012/0116489 A1 | 5/2012 | Khairkhahan et al. |
| 2012/0123276 A1 | 5/2012 | Govari et al. |
| 2012/0123716 A1 | 5/2012 | Clark |
| 2012/0136346 A1 | 5/2012 | Condie et al. |
| 2012/0149966 A1 | 6/2012 | Ludwin et al. |
| 2012/0149967 A1 | 6/2012 | Ludwin et al. |
| 2012/0150075 A1 | 6/2012 | Ludwin et al. |
| 2012/0150251 A1 | 6/2012 | Giftakis et al. |
| 2012/0158111 A1 | 6/2012 | Khairkhahan et al. |
| 2012/0165827 A1 | 6/2012 | Khairkhahan et al. |
| 2012/0172690 A1 | 7/2012 | Anderson et al. |
| 2012/0172867 A1 | 7/2012 | Ryu et al. |
| 2012/0172891 A1* | 7/2012 | Lee .................. A61B 17/3468 606/129 |
| 2012/0172892 A1 | 7/2012 | Grubac et al. |
| 2012/0172942 A1 | 7/2012 | Berg |
| 2012/0179068 A1 | 7/2012 | Leo et al. |
| 2012/0197350 A1 | 8/2012 | Roberts et al. |
| 2012/0197373 A1 | 8/2012 | Khairkhahan et al. |
| 2012/0209260 A1 | 8/2012 | Lambert et al. |
| 2012/0215285 A1 | 8/2012 | Tahmasian et al. |
| 2012/0232565 A1 | 9/2012 | Kveen et al. |
| 2012/0265069 A1 | 10/2012 | Sliwa et al. |
| 2012/0265070 A1 | 10/2012 | Sliwa et al. |
| 2012/0265102 A1 | 10/2012 | Leo et al. |
| 2012/0272518 A1 | 11/2012 | Cui et al. |
| 2012/0277600 A1 | 11/2012 | Greenhut |
| 2012/0277606 A1 | 11/2012 | Ellingson et al. |
| 2012/0283795 A1 | 11/2012 | Stancer et al. |
| 2012/0283807 A1 | 11/2012 | Deterre et al. |
| 2012/0290025 A1* | 11/2012 | Keimel ................ A61N 1/3756 607/3 |
| 2012/0296381 A1 | 11/2012 | Matos |
| 2012/0302882 A1 | 11/2012 | Sliwa et al. |
| 2012/0303082 A1 | 11/2012 | Dong et al. |
| 2012/0316613 A1 | 12/2012 | Keefe et al. |
| 2012/0323237 A1 | 12/2012 | Paul et al. |
| 2013/0006137 A1 | 1/2013 | Hauck et al. |
| 2013/0012151 A1 | 1/2013 | Hankins |
| 2013/0023784 A1 | 1/2013 | Schneider et al. |
| 2013/0023975 A1 | 1/2013 | Locsin |
| 2013/0035748 A1 | 2/2013 | Bonner et al. |
| 2013/0041422 A1 | 2/2013 | Jacobson |
| 2013/0053730 A1 | 2/2013 | Kotlanka et al. |
| 2013/0053908 A1 | 2/2013 | Smith et al. |
| 2013/0053915 A1 | 2/2013 | Holmstrom et al. |
| 2013/0053921 A1 | 2/2013 | Bonner et al. |
| 2013/0060245 A1 | 3/2013 | Grunewald et al. |
| 2013/0060298 A1 | 3/2013 | Splett et al. |
| 2013/0066169 A1 | 3/2013 | Rys et al. |
| 2013/0072770 A1 | 3/2013 | Rao et al. |
| 2013/0079798 A1 | 3/2013 | Tran et al. |
| 2013/0079861 A1 | 3/2013 | Reinert et al. |
| 2013/0085350 A1 | 4/2013 | Schugt et al. |

(56) References Cited

U.S. PATENT DOCUMENTS

| | | |
|---|---|---|
| 2013/0085403 A1 | 4/2013 | Gunderson et al. |
| 2013/0085416 A1 | 4/2013 | Mest |
| 2013/0085550 A1 | 4/2013 | Polefko et al. |
| 2013/0096551 A1 | 4/2013 | Govari et al. |
| 2013/0096649 A1 | 4/2013 | Martin et al. |
| 2013/0103047 A1 | 4/2013 | Steingisser et al. |
| 2013/0103109 A1 | 4/2013 | Jacobson |
| 2013/0110008 A1 | 5/2013 | Bourget et al. |
| 2013/0110127 A1 | 5/2013 | Bornzin et al. |
| 2013/0110192 A1 | 5/2013 | Tran et al. |
| 2013/0110219 A1 | 5/2013 | Bornzin et al. |
| 2013/0116529 A1 | 5/2013 | Min et al. |
| 2013/0116738 A1 | 5/2013 | Samade et al. |
| 2013/0116740 A1 | 5/2013 | Bornzin et al. |
| 2013/0116741 A1 | 5/2013 | Bornzin et al. |
| 2013/0123775 A1 | 5/2013 | Grunewald et al. |
| 2013/0123872 A1 | 5/2013 | Bornzin et al. |
| 2013/0123875 A1 | 5/2013 | Varady et al. |
| 2013/0131591 A1 | 5/2013 | Berthiaume et al. |
| 2013/0131663 A1 | 5/2013 | Govari et al. |
| 2013/0131669 A1 | 5/2013 | Tegg et al. |
| 2013/0131693 A1 | 5/2013 | Berthiaume et al. |
| 2013/0138006 A1 | 5/2013 | Bornzin et al. |
| 2013/0138099 A1 | 5/2013 | Paul et al. |
| 2013/0150695 A1 | 6/2013 | Biela et al. |
| 2013/0150911 A1 | 6/2013 | Perschbacher et al. |
| 2013/0150912 A1 | 6/2013 | Perschbacher et al. |
| 2013/0158436 A1 | 6/2013 | Kocjancic et al. |
| 2013/0158477 A1 | 6/2013 | Goldenberg et al. |
| 2013/0158538 A1 | 6/2013 | Govari |
| 2013/0158548 A1 | 6/2013 | Govari et al. |
| 2013/0172784 A1 | 7/2013 | Kirschenman |
| 2013/0172868 A1 | 7/2013 | Bonfeld |
| 2013/0172869 A1 | 7/2013 | Bonfeld |
| 2013/0172875 A1 | 7/2013 | Govari et al. |
| 2013/0184776 A1 | 7/2013 | Shuros et al. |
| 2013/0190754 A1 | 7/2013 | Paul et al. |
| 2013/0196703 A1 | 8/2013 | Masoud et al. |
| 2013/0197609 A1 | 8/2013 | Moore et al. |
| 2013/0204142 A1 | 8/2013 | Bertholds et al. |
| 2013/0204157 A1 | 8/2013 | Clark et al. |
| 2013/0226169 A1 | 8/2013 | Miller et al. |
| 2013/0231710 A1 | 9/2013 | Jacobson |
| 2013/0238072 A1 | 9/2013 | Deterre et al. |
| 2013/0238073 A1 | 9/2013 | Makdissi et al. |
| 2013/0248024 A1 | 9/2013 | Dunn et al. |
| 2013/0253342 A1 | 9/2013 | Griswold et al. |
| 2013/0253343 A1 | 9/2013 | Waldhauser et al. |
| 2013/0253344 A1 | 9/2013 | Griswold et al. |
| 2013/0253345 A1 | 9/2013 | Griswold et al. |
| 2013/0253346 A1 | 9/2013 | Griswold et al. |
| 2013/0253347 A1 | 9/2013 | Griswold et al. |
| 2013/0253503 A1 | 9/2013 | Govari et al. |
| 2013/0261491 A1 | 10/2013 | Paul et al. |
| 2013/0261497 A1 | 10/2013 | Pertijs et al. |
| 2013/0265144 A1 | 10/2013 | Banna et al. |
| 2013/0268042 A1 | 10/2013 | Hastings et al. |
| 2013/0274828 A1 | 10/2013 | Willis |
| 2013/0274847 A1 | 10/2013 | Ostroff |
| 2013/0282038 A1 | 10/2013 | Dannaher et al. |
| 2013/0282070 A1 | 10/2013 | Cowan et al. |
| 2013/0282073 A1 | 10/2013 | Cowan et al. |
| 2013/0283934 A1 | 10/2013 | Bazargan et al. |
| 2013/0296727 A1 | 11/2013 | Sullivan et al. |
| 2013/0296840 A1 | 11/2013 | Condie et al. |
| 2013/0296850 A1 | 11/2013 | Olson |
| 2013/0303872 A1 | 11/2013 | Taff et al. |
| 2013/0324825 A1 | 12/2013 | Ostroff et al. |
| 2013/0325081 A1 | 12/2013 | Karst et al. |
| 2013/0345770 A1 | 12/2013 | Dianaty et al. |
| 2014/0012344 A1 | 1/2014 | Hastings et al. |
| 2014/0018876 A1 | 1/2014 | Ostroff |
| 2014/0018877 A1 | 1/2014 | Demmer et al. |
| 2014/0024970 A1 | 1/2014 | Govari |
| 2014/0031836 A1 | 1/2014 | Ollivier |
| 2014/0035735 A1 | 2/2014 | Zellers et al. |
| 2014/0039312 A1 | 2/2014 | Rockweiller et al. |
| 2014/0039570 A1 | 2/2014 | Carroll et al. |
| 2014/0039591 A1 | 2/2014 | Drasler et al. |
| 2014/0043146 A1 | 2/2014 | Makdissi et al. |
| 2014/0046395 A1 | 2/2014 | Regnier et al. |
| 2014/0046420 A1 | 2/2014 | Moore et al. |
| 2014/0051959 A1 | 2/2014 | Gliner et al. |
| 2014/0058240 A1 | 2/2014 | Mothilal et al. |
| 2014/0058494 A1 | 2/2014 | Ostroff et al. |
| 2014/0074114 A1 | 3/2014 | Khairkhahan et al. |
| 2014/0074186 A1 | 3/2014 | Faltys et al. |
| 2014/0081264 A1 | 3/2014 | Fandrey et al. |
| 2014/0088588 A1 | 3/2014 | Jarrard |
| 2014/0094688 A1 | 4/2014 | Tegg et al. |
| 2014/0094891 A1 | 4/2014 | Pare et al. |
| 2014/0100563 A1 | 4/2014 | Govari et al. |
| 2014/0100627 A1 | 4/2014 | Min |
| 2014/0107430 A1 | 4/2014 | Deno et al. |
| 2014/0107627 A1 | 4/2014 | Blumenkranz et al. |
| 2014/0107723 A1 | 4/2014 | Hou et al. |
| 2014/0121660 A1 | 5/2014 | Hauck |
| 2014/0121719 A1 | 5/2014 | Bonner et al. |
| 2014/0121720 A1 | 5/2014 | Bonner et al. |
| 2014/0121722 A1 | 5/2014 | Sheldon et al. |
| 2014/0128935 A1 | 5/2014 | Kumar et al. |
| 2014/0135865 A1 | 5/2014 | Hastings et al. |
| 2014/0142648 A1 | 5/2014 | Smith et al. |
| 2014/0148675 A1 | 5/2014 | Nordstrom et al. |
| 2014/0148815 A1 | 5/2014 | Wenzel et al. |
| 2014/0155950 A1 | 6/2014 | Hastings et al. |
| 2014/0169162 A1 | 6/2014 | Romano et al. |
| 2014/0172060 A1 | 6/2014 | Bornzin et al. |
| 2014/0180306 A1 | 6/2014 | Grubac et al. |
| 2014/0180366 A1 | 6/2014 | Edlund |
| 2014/0207149 A1 | 7/2014 | Hastings et al. |
| 2014/0207210 A1 | 7/2014 | Willis et al. |
| 2014/0214104 A1 | 7/2014 | Greenhut et al. |
| 2014/0222098 A1 | 8/2014 | Baru et al. |
| 2014/0222109 A1 | 8/2014 | Moulder |
| 2014/0228913 A1 | 8/2014 | Molin et al. |
| 2014/0236172 A1 | 8/2014 | Hastings et al. |
| 2014/0243848 A1 | 8/2014 | Auricchio et al. |
| 2014/0255298 A1 | 9/2014 | Cole et al. |
| 2014/0257324 A1 | 9/2014 | Fain |
| 2014/0257422 A1 | 9/2014 | Herken |
| 2014/0257444 A1 | 9/2014 | Cole et al. |
| 2014/0276929 A1 | 9/2014 | Foster et al. |
| 2014/0303704 A1 | 10/2014 | Suwito et al. |
| 2014/0309706 A1 | 10/2014 | Jacobson |
| 2014/0379041 A1 | 12/2014 | Foster |
| 2015/0025612 A1 | 1/2015 | Haasl et al. |
| 2015/0039041 A1 | 2/2015 | Smith et al. |
| 2015/0051609 A1 | 2/2015 | Schmidt et al. |
| 2015/0051610 A1 | 2/2015 | Schmidt et al. |
| 2015/0051611 A1 | 2/2015 | Schmidt et al. |
| 2015/0051612 A1 | 2/2015 | Schmidt et al. |
| 2015/0051613 A1 | 2/2015 | Schmidt et al. |
| 2015/0051614 A1 | 2/2015 | Schmidt et al. |
| 2015/0051615 A1 | 2/2015 | Schmidt et al. |
| 2015/0051616 A1 | 2/2015 | Haasl et al. |
| 2015/0051682 A1 | 2/2015 | Schmidt et al. |
| 2015/0057520 A1 | 2/2015 | Foster et al. |
| 2015/0057558 A1 | 2/2015 | Stahmann et al. |
| 2015/0057721 A1 | 2/2015 | Stahmann et al. |
| 2015/0088155 A1 | 3/2015 | Stahmann et al. |
| 2015/0105836 A1 | 4/2015 | Bonner et al. |
| 2015/0157861 A1 | 6/2015 | Aghassian |
| 2015/0173655 A1 | 6/2015 | Demmer et al. |
| 2015/0190638 A1 | 7/2015 | Smith et al. |
| 2015/0196756 A1 | 7/2015 | Stahmann et al. |
| 2015/0196757 A1 | 7/2015 | Stahmann et al. |
| 2015/0196758 A1 | 7/2015 | Stahmann et al. |
| 2015/0196769 A1 | 7/2015 | Stahmann et al. |
| 2015/0217119 A1 | 8/2015 | Nikolski et al. |
| 2015/0221898 A1 | 8/2015 | Chi et al. |
| 2015/0224315 A1 | 8/2015 | Stahmann |
| 2015/0224320 A1 | 8/2015 | Stahmann |
| 2015/0258345 A1 | 9/2015 | Smith et al. |

(56) References Cited

U.S. PATENT DOCUMENTS

| | | |
|---|---|---|
| 2015/0290468 A1 | 10/2015 | Zhang |
| 2015/0297905 A1 | 10/2015 | Greenhut et al. |
| 2015/0297907 A1 | 10/2015 | Zhang |
| 2015/0305637 A1 | 10/2015 | Greenhut et al. |
| 2015/0305638 A1 | 10/2015 | Zhang |
| 2015/0305639 A1 | 10/2015 | Greenhut et al. |
| 2015/0305640 A1 | 10/2015 | Reinke et al. |
| 2015/0305641 A1 | 10/2015 | Stadler et al. |
| 2015/0305642 A1 | 10/2015 | Reinke et al. |
| 2015/0306374 A1 | 10/2015 | Seifert et al. |
| 2015/0306375 A1 | 10/2015 | Marshall et al. |
| 2015/0306378 A1* | 10/2015 | Schmidt ............... A61N 1/059 600/424 |
| 2015/0306406 A1 | 10/2015 | Crutchfield et al. |
| 2015/0306407 A1 | 10/2015 | Crutchfield et al. |
| 2015/0306408 A1 | 10/2015 | Greenhut et al. |
| 2015/0321016 A1 | 11/2015 | O'Brien et al. |
| 2015/0328459 A1 | 11/2015 | Chin et al. |
| 2016/0015322 A1 | 1/2016 | Anderson et al. |
| 2016/0023000 A1 | 1/2016 | Cho et al. |
| 2016/0030757 A1 | 2/2016 | Jacobson |
| 2016/0033177 A1 | 2/2016 | Barot et al. |
| 2016/0121127 A1 | 5/2016 | Klimovitch et al. |
| 2016/0121128 A1 | 5/2016 | Fishler et al. |
| 2016/0121129 A1 | 5/2016 | Persson et al. |
| 2016/0213919 A1 | 7/2016 | Suwito et al. |
| 2016/0213937 A1 | 7/2016 | Reinke et al. |
| 2016/0213939 A1 | 7/2016 | Carney et al. |
| 2016/0228026 A1 | 8/2016 | Jackson |
| 2016/0317825 A1 | 11/2016 | Jacobson |
| 2016/0367823 A1 | 12/2016 | Cowan et al. |
| 2017/0014629 A1 | 1/2017 | Ghosh et al. |
| 2017/0035315 A1 | 2/2017 | Jackson |
| 2017/0043173 A1 | 2/2017 | Sharma et al. |
| 2017/0043174 A1 | 2/2017 | Greenhut et al. |
| 2017/0189681 A1 | 7/2017 | Anderson |
| 2017/0281261 A1 | 10/2017 | Shuros et al. |
| 2017/0281952 A1 | 10/2017 | Shuros et al. |
| 2017/0281953 A1 | 10/2017 | Min et al. |
| 2017/0281955 A1 | 10/2017 | Maile et al. |
| 2017/0312531 A1 | 11/2017 | Sawchuk |

FOREIGN PATENT DOCUMENTS

| | | |
|---|---|---|
| AU | 2014203793 A1 | 7/2014 |
| CA | 1003904 A1 | 1/1977 |
| CN | 202933393 U | 5/2013 |
| EP | 0362611 A1 | 9/1990 |
| EP | 503823 A2 | 9/1992 |
| EP | 1702648 A2 | 9/2006 |
| EP | 2187829 A4 | 9/2010 |
| EP | 1904166 B1 | 6/2011 |
| EP | 2425871 A3 | 4/2012 |
| EP | 2433675 B1 | 1/2013 |
| EP | 2441491 B1 | 1/2013 |
| EP | 2612612 A1 | 7/2013 |
| EP | 2452721 B1 | 11/2013 |
| EP | 1948296 B1 | 1/2014 |
| EP | 2662113 A3 | 1/2014 |
| EP | 2700373 A1 | 2/2014 |
| EP | 2719351 A1 | 4/2014 |
| EP | 2471452 B1 | 12/2014 |
| EP | 1962710 A2 | 8/2015 |
| EP | 2662015 A1 | 4/2016 |
| EP | 2760541 B1 | 5/2016 |
| EP | 2833966 B1 | 5/2016 |
| JP | 1997135906 A | 5/1997 |
| JP | 1997149940 A | 6/1997 |
| JP | 2000051373 A | 2/2000 |
| JP | 2002502640 A | 1/2002 |
| JP | 2004512105 A | 4/2004 |
| JP | 2005508208 A | 3/2005 |
| JP | 2005245215 A | 9/2005 |
| JP | 2006064465 A | 3/2006 |
| JP | 2008540040 A | 11/2008 |
| JP | 5199867 B2 | 2/2013 |
| WO | 9500202 A1 | 1/1995 |
| WO | 9636134 A1 | 11/1996 |
| WO | 9724981 A2 | 7/1997 |
| WO | 9826840 A1 | 6/1998 |
| WO | 9939767 A1 | 8/1999 |
| WO | 2000078239 A2 | 12/2000 |
| WO | 2002019906 A2 | 6/2002 |
| WO | 0234330 A2 | 1/2003 |
| WO | 2002024063 B1 | 2/2003 |
| WO | 02098282 A2 | 5/2003 |
| WO | 2005000206 A2 | 1/2005 |
| WO | 2005011511 A1 | 2/2005 |
| WO | 2005042089 A1 | 5/2005 |
| WO | 2006065394 A1 | 6/2006 |
| WO | 2006086435 A2 | 8/2006 |
| WO | 2006109109 A1 | 10/2006 |
| WO | 2006113659 A1 | 10/2006 |
| WO | 2006124833 A2 | 11/2006 |
| WO | 2007041540 A1 | 4/2007 |
| WO | 2007067628 A1 | 6/2007 |
| WO | 2007067939 A2 | 6/2007 |
| WO | 2007067939 A3 | 6/2007 |
| WO | 2007067940 A2 | 6/2007 |
| WO | 2007067940 A3 | 6/2007 |
| WO | 2007067941 A2 | 6/2007 |
| WO | 2007067941 A3 | 6/2007 |
| WO | 2007067943 A2 | 6/2007 |
| WO | 2007067943 A3 | 6/2007 |
| WO | 2007070361 A2 | 6/2007 |
| WO | 2007070361 A3 | 6/2007 |
| WO | 2007070919 A1 | 6/2007 |
| WO | 2007075974 A2 | 7/2007 |
| WO | 2007067938 A2 | 12/2007 |
| WO | 2007067938 A3 | 12/2007 |
| WO | 2007067937 A2 | 4/2008 |
| WO | 2007067937 A3 | 4/2008 |
| WO | 2008063195 A1 | 5/2008 |
| WO | 2008083311 A2 | 10/2008 |
| WO | 2008083311 A3 | 10/2008 |
| WO | 2009006531 A1 | 1/2009 |
| WO | 2009070837 A1 | 6/2009 |
| WO | 2009085457 A1 | 7/2009 |
| WO | 2010042461 A1 | 4/2010 |
| WO | 2010132472 A1 | 11/2010 |
| WO | 2011034925 A1 | 3/2011 |
| WO | 2011062653 A1 | 5/2011 |
| WO | 2011062681 A1 | 5/2011 |
| WO | 2011044387 A2 | 6/2011 |
| WO | 2011072221 A1 | 6/2011 |
| WO | 2012054102 A1 | 4/2012 |
| WO | 2012067682 A1 | 5/2012 |
| WO | 2012082249 A1 | 6/2012 |
| WO | 2012092275 A1 | 7/2012 |
| WO | 2012142588 A1 | 10/2012 |
| WO | 2012156914 A2 | 11/2012 |
| WO | 2013043804 A1 | 3/2013 |
| WO | 2013080038 A2 | 6/2013 |
| WO | 2013098644 A2 | 7/2013 |
| WO | 2013159940 A1 | 10/2013 |
| WO | 2013162884 A1 | 10/2013 |
| WO | 2013184787 A1 | 12/2013 |
| WO | 2014089545 A1 | 6/2014 |
| WO | 2014120769 A1 | 8/2014 |

OTHER PUBLICATIONS

US 8,886,318 B2, 11/2014, Jacobson et al. (withdrawn)
International Search Report and Written Opinion for Application No. PCT/US2017/016212, 32 pages, dated May 18, 2017.
"Instructions for Use System 1, Leadless Cardiac Pacemaker (LCP) and Delivery Catheter," Nanostim Leadless Pacemakers, pp. 1-28, 2013.
Cao et al. "FEM Analysis of Predicting Electrode-Myocardium Contact From RF Cardiac Catheter Ablation System Impedance", IEEE Transactions on Biomedical Engineering, vol. 49(6): 520-526 2002.

(56) References Cited

OTHER PUBLICATIONS

Cao et al., "Using electrical impedance to predict catheter-endocardial contact during RF cardiac ablation," IEEE Trans Biomed Eng., vol. 49(3): 247-53, 2002.
Dello et al., "Simultaneous assessment of contact pressure and local electrical coupling index using robotic navigation," J Intery Card Electrophysiol., 2014.
Deno et al., "Measurement of electrical coupling between cardiac ablation catheters and tissue," IEEE Trans Biomed Eng., vol. 61(3): 765-74, 2014.
Di Biase et al., "Visual, tactile, and contact force feedback: which one is more important for catheter ablation? Results from an in vitro experimental study,"Heart Rhythm, vol. 11(3):506-13, 2014.
Eick et al., "The LETR-Principle: a novel method to assess electrode-tissue contact in radiofrequency ablation," J Cardiovasc Electrophysiol., vol. 9(11): 1180-5, 1998.
Eick, "Factors Influencing Lesion Formation During Radiofrequency Catheter Ablation, " Indian Pacing and Electrophysiology Journal, vol. 3(3): 117-128, 2003.
Everett et al., "Phase Angle Shift is a Better Determinant for Catheter Electrode Contact With Tissue Compared to a Catheter Sensed Electrogram," Conf Proc IEEE Eng Med Biol Soc., 1733-6, 2008.
Fenelon et al., "Epicardial radiofrequency ablation of ventricular myocardium: factors affecting lesion formation and damage to adjacent structures," J Interv Card Electrophysiol., vol. 15(1): 57-63, 2006.
Gerstenfeld, "Contact force-sensing catheters: evolution or revolution in catheter ablation technology," Circ Arrhythm Electrophysiol. vol. 7(1): 5-6, 2014.
Hachisuka et al., "Development and Performance Analysis of an Intra-Body Communication Device," The 12th International Conference on Solid State Sensors, Actuators and Microsystems, vol. 4A1.3, pp. 1722-1725, 2003.
Haines, "Determinants of Lesion Size During Radiofrequency Catheter Ablation: The Role of Electrode-Tissue Contact Pressure and Duration of Energy Delivery," Journal of Cardiovascular Electrophysiology, vol. 2(6): 509-515, 1991.
Keane, "New catheter ablation techniques for the treatment of cardiac arrhythmias," Card Electrophysiol Rev., vol. 6 (4): 341-8, 2002.
Ko et al., "New method for predicting efficiency of heating by measuring bioimpedance during radiofrequency catheter ablation in humans," J Cardiovasc Electrophysiol. vol. 12(7):819-23, 2001.
Kuck et al., "A novel radiofrequency ablation catheter using contact force sensing: Toccata study," Heart Rhythm. vol. 9(1):18-23, 2012.
Kumar et al. "Predictive value of impedance changes for real-time contact force measurements during catheter ablation of atrial arrhythmias in humans," Heart Rhythm. vol. 10(7):962-9, 2013.
Makimoto et al., "n vivo contact force analysis and correlation with tissue impedance during left atrial mapping and catheter ablation of atrial fibrillation," Circ Arrhythm Electrophysiol. vol. 7(1): 46-54, 2014.
Marijon et al., "Real-Time Contact Force Sensing for Pulmonary Vein Isolation in the Setting of Paroxysmal Atrial Fibrillation: Procedural and 1-Year Results,"J Cardiovasc Electrophysiol. 2013.
Martinek et al., "Clinical impact of an open-irrigated radiofrequency catheter with direct force measurement on atrial fibrillation ablation," Pacing Clin Electrophysiol, vol. 35(11):1312-8, 2012.
Nakagawa et al., "Locations of high contact force during left atrial mapping in atrial fibrillation patients: electrogram amplitude and impedance are poor predictors of electrode-tissue contact force for ablation of atrial fibrillation," Circ Arrhythm Electrophysiol, vol. 6(4): 746-53, 2013.
Nath et al., "Basic aspects of radiofrequency catheter ablation," J Cardiovasc Electrophysiol., vol. 5(10): 863-76, 1994.
Notification of Transmittal of the International Search Report and the Written Opinion of the International Searching Authority, or the Declaration, dated Jan. 29, 2016, 15 pages.
Petersen et al., "Can lesion size during radiofrequency ablation be predicted by the temperature rise to a low power test pulse in vitro," Pacing Clin Electrophysiol., vol. 26(8): 1653-9, 2003.
Petersen et al., "Temperature-controlled radiofrequency ablation of cardiac tissue: an in vitro study of the impact of electrode orientation, electrode tissue contact pressure and external convective cooling," J Interv Card Electrophysiol., vol. 3(3): 257-62, 1999.
Reichlin et al., "Initial Impedance Decrease as an Indicator of Good Catheter Contact: Insights From Radiofrequency Ablation With Force Sensing Catheters," Heart Rhythm, vol. 11(2): 194-201, 2014.
Seyedi et al., "A Survey on Intrabody Communications for Body Area Network Application," IEEE Transactions on Biomedical Engineenng,vol. 60(8): 2067-2079, 2013.
Spickler et al., "Totally Self-Contained Intracardiac Pacemaker," Journal of Electrocardiology, vol. 3(3&4): 324-331, 1970.
Squara et al., "Contact force and force-time integral in atrialradiofrequency ablation predict transmurality of lesions," Europace, vol. 16: 660-667, 2014.
Stabile et al., "Catheter-tissue contact force for pulmonary veins isolation: a pilot multicentre study on effect on procedure and fluoroscopy time," vol. 16(3): 335-40, 2014.
Stagegaard et al., "Indication of the radiofrequency induced lesion size bypre-ablation measurements," Europace. vol. 7(6):525-34, 2005.
Thiagalingam et al., "Importance of catheter contact force during irrigated radiofrequency ablation: evaluation in a porcine ex vivo model using a force-sensing catheter," J Cardiovasc Electrophysiol., vol. 21(7): 806-11, 2010.
Tsai et al., "Dependence of Apparent Resistance of Four-Electrode Probes on Insertion Depth," IEEE Transactions on Biomedical Engineering, vol. 47(1): 41-48, 2000.
Tsai et al., "Error Analysis of Tissue Resistivity Measurement," IEEE Transactions on Biomedical Engineering, vol. 49 (5): 484-494, 2002.
Valk et al.,"Catheter ablation of right ventricular outflow tract tachycardia using contact force guidance,"Neth Heart J. 2014.
Wakili et al., "Impact of Real-Time Contact Force and Impedance Measurement in Pulmonary Vein Isolation Procedures for Treatment of Atrial Fibrillation," Clin Res Cardiol, vol. 103(2): 97-106, 2014.
Wegmüller, "Intra-Body Communication for Biomedical Sensor Networks," Diss. ETH, No. 17323, 1-173, 2007.
Weiss et al., "Radiofrequency catheter ablation using cooled electrodes: impact of irrigation flow rate and catheter contact pressure on lesion dimensions,"Pacing Clin Electrophysiol., vol. 25(4 Pt 1): 463-9, 2002.
Yokoyama et al., "Novel contact force sensor incorporated in irrigated radiofrequency ablation catheter predicts lesion size and incidence of steam pop and thrombus,"Circ Arrhythm Electrophysiol., vol. 1(5):354-62, 2008.
Zheng et al., "Electrode Impedance: An Indicator of Electrode-Tissue Contact and Lesion Dimensions During Linear Ablation," Journal of Interventional Cardiac Electrophysiology, vol. 4(4): 645-654, 2000.

* cited by examiner

DELIVERY SYSTEM WITH FORCE SENSOR FOR LEADLESS CARDIAC DEVICE

CROSS REFERENCE TO RELATED APPLICATIONS

This application claims the benefit of U.S. Provisional Patent Application Ser. No. 62/291,330 filed on Feb. 4, 2016, the disclosure of which is incorporated herein by reference.

TECHNICAL FIELD

The present disclosure pertains to medical devices, and methods for manufacturing and/or using medical devices. More particularly, the present disclosure pertains to leadless devices and methods, such as leadless pacing devices and methods, and delivery devices and methods for such leadless devices.

BACKGROUND

A wide variety of medical devices have been developed for medical use, for example, cardiac use. Some of these devices include catheters, leads, pacemakers, and the like, and delivery devices and/or systems used for delivering such devices. These devices are manufactured by any one of a variety of different manufacturing methods and may be used according to any one of a variety of methods. Of the known medical devices, delivery systems, and methods, each has certain advantages and disadvantages. There is an ongoing need to provide alternative medical devices and delivery devices as well as alternative methods for manufacturing and using medical devices and delivery devices.

SUMMARY

This disclosure provides design, material, manufacturing method, and use alternatives for medical devices, including delivery devices.

An example delivery and deployment device may include a handle assembly and a shaft extending distally from the handle assembly. A distal containment housing may be coupled to a distal region of the shaft and extend distally therefrom. The distal containment housing may be configured to accommodate an Implantable Medical Device (IMD) therein. The IMD may be a leadless pacemaker, a lead, a neurostimulation device, a sensor or any other suitable IMD. At least one of the shaft and distal containment housing may include a compressible region that is configured to compress by an amount that is related to an applied force. The example delivery and deployment device may include a first position indicator and a second position indicator, wherein at least part of the compressible region is situated between the first position indicator and the second position indicator. An applied force causes the compressible region to compress by an amount that is related to the applied force, which causes a change in distance between the first position indicator and the second position indicator, which provides an indication of the applied force.

In some cases, the distal containment housing may include the compressible region.

In some cases, the compressible region may be configured to shorten in length in response to the applied force. In some cases, there are more than one compressible region.

In some cases, the first position indicator comprises a first radiopaque marker band and the second position indicator comprises a second radiopaque marker band, and the change in distance between the first position indicator and the second position indicator is visible via fluoroscopy.

In some cases, the first position indicator comprises a first electrode and the second position indicator comprises a second electrode, and the change in distance between the first electrode and the second electrode is indicated via a change in impedance between the first electrode and the second electrode. In some cases, the first electrode may include a ring electrode. Alternatively or additionally, the first electrode may include one or more of a plurality of electrodes that are disposed radially about a distal end of the distal containment housing and alignable with each of a plurality of talons of the IMD. In some cases, the second electrode may comprises a ring electrode or any other suitable electrode.

In some cases, the delivery and deployment device may further include a force sensor arranged and configured to provide an indication of a force applied to the IMD during implantation. In some cases, the delivery and deployment device may include a force sensor arranged and configured to provide an indication of an applied force to an IMD during a tug test after deployment of the IMD.

A second example IMD implantation device may include a handle assembly and a shaft extending distally from the handle assembly. A distal containment housing that is configured to accommodate the IMD therein may be coupled to a distal region of the shaft and extend distally therefrom. A deployment member may extend through the shaft and may be configured to apply a distal deployment force to the IMD in order to move the IMD from the distal containment housing to deploy the IMD in the patient's heart. The second example IMD implantation device may further include a first force detector for detecting a measure related to a force applied by the device containment housing against the patient's heart during deployment of the IMD and a second force detector for detecting a measure related to a applied by the deployment member to the IMD during deployment of the IMD.

In some cases, the deployment member may be a push tube, and the IMD implantation device may include a tether extending distally through the push tube and coupled to the IMD. The tether may be configured to be used to retrieve the IMD back into the distal containment housing if an alternate deployment location is desired.

In some cases, the IMD implantation device may further include a plurality of electrodes that are disposed radially about a distal end of the distal containment housing and alignable with each of a plurality of talons of the IMD.

In some cases, the first force detector may include a compressible region that is configured to compresses by an amount that is related to the force applied by the device containment housing against the patient's heart during deployment of the IMD.

In some cases, the first force detector may include a first electrode and a second electrode, wherein at least part of the compressible region is between the first electrode and the second electrode.

In some cases, the first force detector may include a strain sensor and/or the second force detector may include a strain sensor.

Another example IMD implantation device may include a shaft including a distal region and a distal containment housing that is configured to accommodate the IMD therein. The distal containment housing may be coupled to the distal region of the shaft and extend distally therefrom. A deployment member may extend through the shaft and may be configured to apply a distal deployment force to the IMD in order to move the IMD from the distal containment housing to deploy the IMD in the patient's heart. A plurality of electrodes may be disposed radially about a distal end of the distal containment housing and may be alignable with each of a plurality of talons of the IMD. One or more force detectors may detect a measure related to a force applied by the distal containment housing against the patient's heart during deployment of the IMD.

In some cases, the force detector may include a compressible region that is configured to compresses by an amount that is related to the force applied by the distal containment housing against the patient's heart during deployment of the IMD. In some cases, the force detector may include a first electrode and a second electrode, wherein at least part of the compressible region is between the first electrode and the second electrode.

The above summary of some illustrative embodiments is not intended to describe each disclosed embodiment or every implementation of the present disclosure. The Figures, and Detailed Description, which follow, more particularly exemplify some of these embodiments.

BRIEF DESCRIPTION OF THE DRAWINGS

The disclosure may be more completely understood in consideration of the following detailed description in connection with the accompanying drawings, in which.

Figure 1:
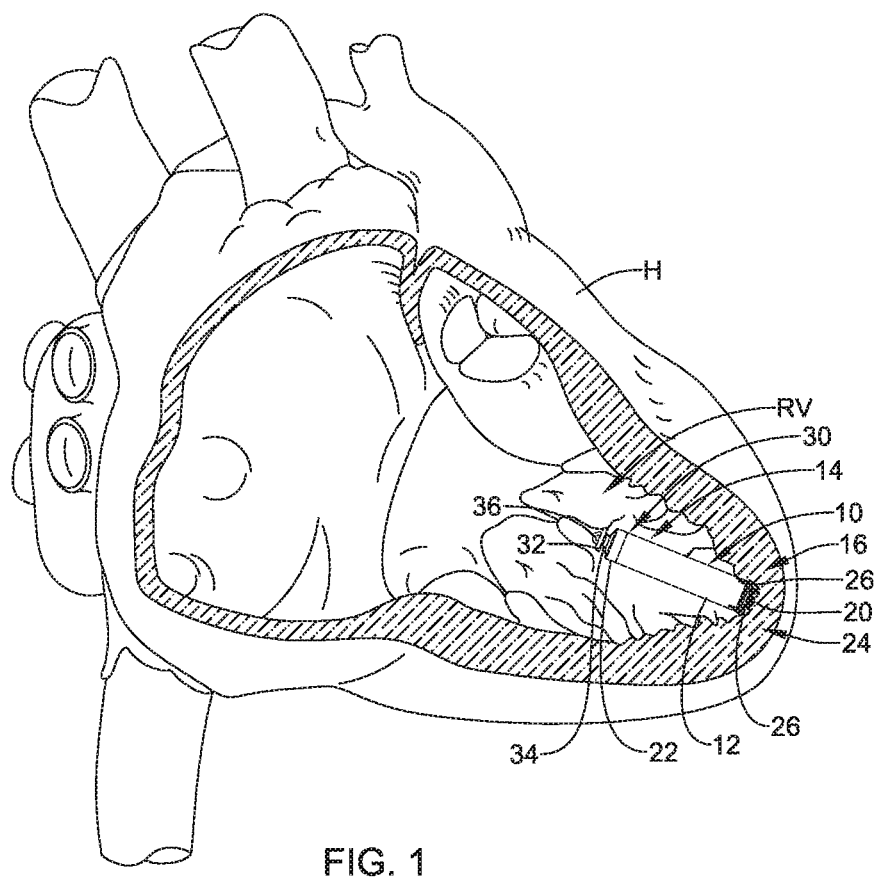
FIG. 1 is a plan view of an example leadless pacing device implanted within a heart.

While the disclosure is amenable to various modifications and alternative forms, specifics thereof have been shown by way of example in the drawings and will be described in detail. It should be understood, however, that the intention is not to limit the disclosure to the particular embodiments described. On the contrary, the intention is to cover all modifications, equivalents, and alternatives falling within the spirit and scope of the disclosure.

DETAILED DESCRIPTION

For the following defined terms, these definitions shall be applied, unless a different definition is given in the claims or elsewhere in this specification.

All numeric values are herein assumed to be modified by the term "about," whether or not explicitly indicated. The term "about" generally refers to a range of numbers that one of skill in the art would consider equivalent to the recited value (i.e., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

It is noted that references in the specification to "an embodiment", "some embodiments", "other embodiments", etc., indicate that the embodiment described may include one or more particular features, structures, and/or characteristics. However, such recitations do not necessarily mean that all embodiments include the particular features, structures, and/or characteristics. Additionally, when particular features, structures, and/or characteristics are described in connection with one embodiment, it should be understood that such features, structures, and/or characteristics may also be used connection with other embodiments whether or not explicitly described unless clearly stated to the contrary.

The following detailed description should be read with reference to the drawings in which similar structures in different drawings are numbered the same. The drawings, which are not necessarily to scale, depict illustrative embodiments and are not intended to limit the scope of the disclosure.

Cardiac pacemakers provide electrical stimulation to heart tissue to cause the heart to contract and thus pump blood through the vascular system. Conventional pacemakers may include an electrical lead that extends from a pulse generator implanted subcutaneously or sub-muscularly to an electrode positioned adjacent the inside or outside wall of the cardiac chamber. As an alternative to conventional pacemakers, self-contained or leadless cardiac pacemakers have been proposed. Leadless cardiac pacemakers are small capsules that may, for example, be fixed to an intracardiac implant site in a cardiac chamber. In some cases, the small capsule may include bipolar pacing/sensing electrodes, a power source (e.g. a battery), and associated electrical circuitry for controlling the pacing/sensing electrodes, and thus may provide electrical stimulation to heart tissue and/or sense a physiological condition. The capsule may be delivered to the heart using a delivery device which may be advanced through a femoral vein, into the inferior vena cava, into the right atrium, through the tricuspid valve, and into the right ventricle. Accordingly, it may be desirable to provide delivery devices which facilitate advancement through the vasculature.

Figure 2:
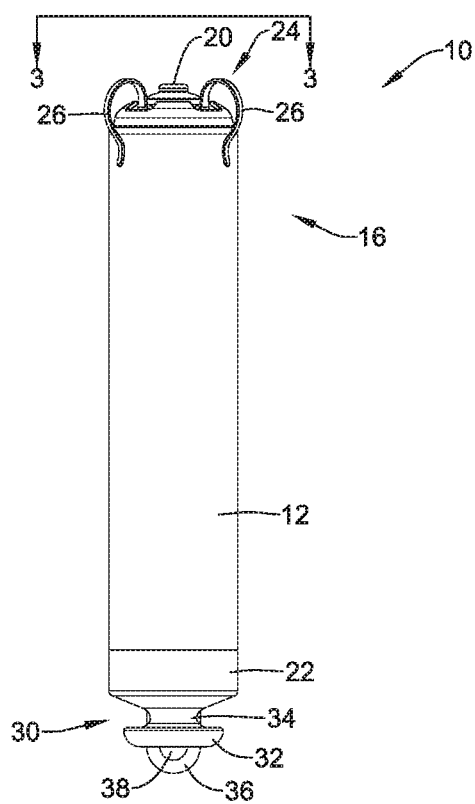
FIG. 2 is a side view of an example implantable leadless cardiac pacing device.
Figure 3:
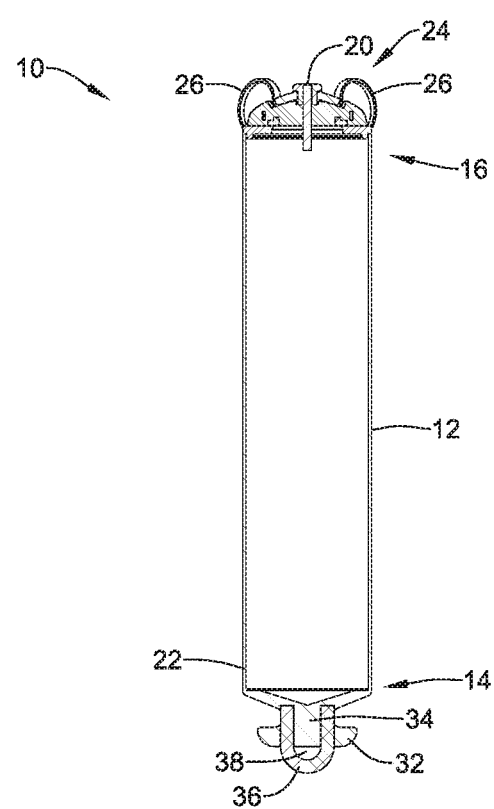
FIG. 3 is a cross-sectional view of the implantable leadless cardiac pacing device of FIG. 2.

FIG. 1 illustrates an example implantable leadless cardiac pacing device 10 (e.g., a leadless pacemaker) implanted in a chamber of a heart H, such as the right ventricle RV. A side view of the illustrative implantable medical device (IMD) 10 is shown in FIG. 2 and a cross-sectional view of the illustrative IMD 10, taken at line 3-3 in FIG. 2, is illustrated in FIG. 3. The implantable device 10 may include a shell or housing 12 having a proximal end 14 and a distal end 16. In some instances, the IMD 10 may include a first electrode 20 positioned adjacent to the distal end 16 of the housing 12 and a second electrode 22 positioned adjacent to the proximal end 14 of the housing 12. In some cases, the housing 12 may include a conductive material and may be insulated at least a portion of its length. A section along the proximal end 14 may be free of insulation so as to define the second electrode 22. The electrodes 20, 22 may be sensing and/or pacing electrodes to provide electro-therapy and/or sensing capabilities. The first electrode 20 may be configured to be positioned against the cardiac tissue of the heart H or may otherwise contact the cardiac tissue of the heart H while the second electrode 22 may be spaced away from the first electrode 20, and thus spaced away from the cardiac tissue.

The IMD 10 may include a pulse generator (e.g., electrical circuitry) and a power source (e.g., a battery) within the housing 12 to provide electrical signals to the electrodes 20, 22 and thus control the pacing/sensing electrodes 20, 22. In some cases, electrical communication between the pulse generator and the electrodes 20, 22 may provide electrical stimulation to heart tissue and/or sense a physiological condition.

The IMD 10 may include a fixation mechanism 24 proximate the distal end 16 of the housing 12 configured to attach the IMD 10 to a tissue wall of the heart H, or otherwise anchor the IMD 10 to the anatomy of the patient. As shown in FIG. 1, in some instances, the fixation mechanism 24 may include one or more, or a plurality of hooks or tines 26 anchored into the cardiac tissue of the heart H to attach the IMD 10 to a tissue wall. In other cases, the fixation mechanism 24 may include one or more, or a plurality of passive tines, configured to entangle with trabeculae within the chamber of the heart H and/or a helical fixation anchor configured to be screwed into a tissue wall to anchor the IMD 10 to the heart H.

The IMD 10 may include a docking member 30 proximate the proximal end 14 of the housing 12 configured to facilitate delivery and/or retrieval of the IMD 10. For example, the docking member 30 may extend from the proximal end 14 of the housing 12 along a longitudinal axis of the housing 12. The docking member 30 may include a head portion 32 and a neck portion 34 extending between the housing 12 and the head portion 32. The head portion 32 may be an enlarged portion relative to the neck portion 34. For example, the head portion 32 may have a radial dimension from the longitudinal axis of the IMD 10 which is greater than a radial dimension of the neck portion 34 from the longitudinal axis of the IMD 10. The docking member 30 may further include a tether retention structure 36 extending from the head portion 32. The tether retention structure 36 may define an opening 38 configured to receive a tether or other anchoring mechanism therethrough. While the retention structure 36 is shown as having a generally "U-shaped" configuration, the retention structure 36 may take any shape which provides an enclosed perimeter surrounding the opening 38 such that a tether may be securably and releasably passed (e.g. looped) through the opening 38. The retention structure 36 may extend though the head portion 32, along the neck portion 34, and to or into the proximal end 14 of the housing 12, as is shown more clearly in FIG. 3. The docking member 30 may be configured to facilitate delivery of the IMD 10 to the intracardiac site and/or retrieval of the IMD 10 from the intracardiac site. Other docking members 30 are contemplated.

In some cases, the IMD 10 may be delivered to the heart H using a delivery device which may be advanced through a femoral vein, into the inferior vena cava, into the right atrium, through the tricuspid valve, and into the right ventricle. Accordingly, it will be appreciated that the delivery device may need to be navigated through relatively tortuous anatomy to deliver the IMD 10 to a suitable location. The target region for the delivery of the IMD 10 may be a portion of the right ventricle, for example, a portion of the right ventricle near the apex of the heart. The target region may also include other regions of the heart (e.g., right atrium, left atrium, or left ventricle), blood vessels, or other suitable targets. It may be desirable to provide the delivery system with certain features that may allow for easier or better control for navigation or delivery purposes.

Figure 4:
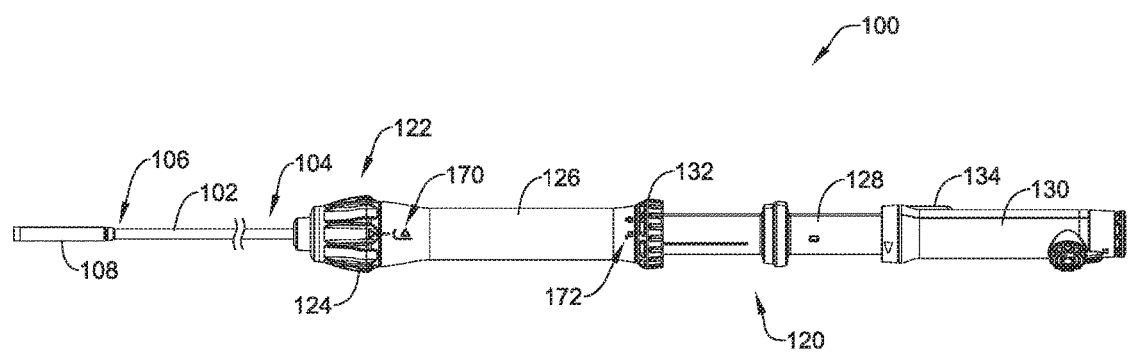
FIG. 4 is a plan view of an example delivery device for an implantable leadless cardiac pacing device.
Figure 5:
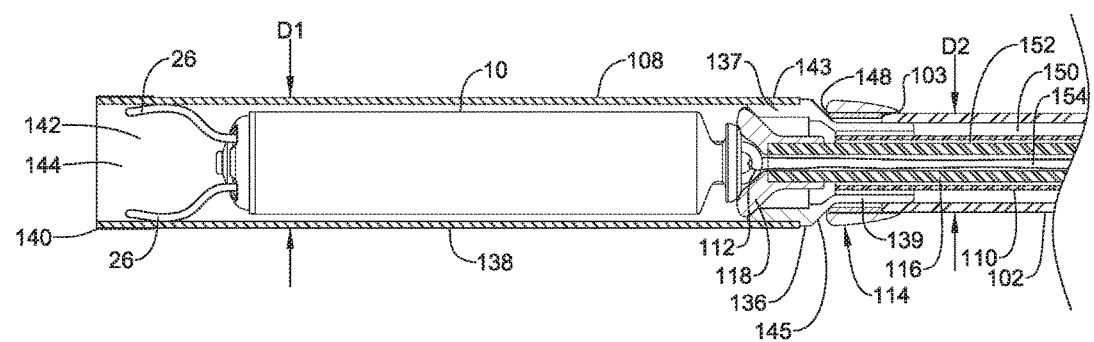
FIG. 5 is a partial cross-sectional side view of the distal portion of the delivery device of FIG. 4.

FIG. 4 is a plan view of an illustrative delivery device 100, such as a catheter, that may be used to deliver the IMD 10. The delivery device 100 may include an outer tubular member 102 having a proximal section 104 and a distal section 106. An intermediate tubular member 110 may be longitudinally slidably disposed within a lumen 150 of the outer tubular member 102 (see e.g. FIG. 5). An inner tubular member 116 may be longitudinally slidably disposed within a lumen 152 of the intermediate tubular member 110 (see e.g. FIG. 5). A distal holding section, or device containment housing 108 may be attached to a distal end portion 114 of the intermediate tubular member 110, as illustrated in FIG. 5. The delivery device 100 may also include a handle assembly 120 positioned adjacent to the proximal section 104 of the outer tubular member 102. In some instances, the outer tubular member 102 may include at least a section thereof that has an outer diameter D2 that is less than the outer diameter D1 of at least a portion of the device containment housing 108 (see e.g. FIG. 5).

The handle assembly 120 may include a first or distal hub portion 126 attached to, such as fixedly attached to, the proximal end section 104 of the outer tubular member 102, a second or intermediate hub portion 128 attached to, such as fixedly attached to, a proximal end section of the intermediate tubular member 110, and a third or proximal hub portion 130 attached to, such as fixedly attached to, a proximal end section of the inner tubular member 116 (see e.g. FIG. 5). The first hub portion 126, second hub portion 128, and third hub portion 130 may be positioned in a generally telescoping arrangement and longitudinally slidable relative to each other. As will be discussed in more detail below, each of the first hub portion 126, the second hub portion 128, and the third hub portion 130 may be longitudinally slidable and rotatable relative to each other such that the outer tubular member 102, intermediate tubular member 110, and inner tubular member 116 may be individually actuated. In some instances, it may be desirable to move the outer tubular member 102, intermediate tubular member 110 and inner tubular member 116 simultaneously.

The handle assembly 120 may include a multi-stage deployment mechanism or a first locking mechanism 134 to releasably couple the second hub portion 128 to the third hub portion 130 to prevent relative longitudinal movement therebetween, and thus prevent relative longitudinal movement between the intermediate tubular member 110 and the inner tubular member 116, as will be discussed in more detail below. The handle assembly 120 may also include a second locking mechanism 132 to releasably couple the first hub portion 126 to the second hub portion 128 to prevent relative longitudinal movement therebetween, and thus prevent relative longitudinal movement between the outer tubular member 102 and the intermediate tubular member 110, as will be discussed in more detail below.

The device containment housing 108 may be configured to receive the IMD 10 therein. For example, referring to FIG. 5, which illustrates a cross-sectional view of a distal portion of the delivery device 100, the device containment housing 108 may define a cavity 142 for slidably receiving the IMD 10, and may include a distal opening 144 for slidable insertion and/or extraction of the IMD 10 into and/or out of the cavity 142. The device containment housing 108 may include a body portion 138 and a distal tip portion 140 that may be, for example, configured to be atraumatic to anatomy, such as a bumper tip. For example, as the catheter is navigated through the anatomy, the distal tip may come into contact with anatomy. Additionally, when the catheter is used to deliver the implantable device 10, the tip 140 of the delivery device 100 will likely come into contact with tissue adjacent the target site (e.g. cardiac tissue of the heart). In some cases, as will be discussed with respect to subsequent Figures, the device containment housing 108 or the outer tubular member 102 proximate the device containment housing 108 may be configured to provide, for example, an indication of the force being applied to the distal tip portion 140 by virtue of the distal tip portion 140 being urged into contact with tissue such as a wall of the heart H.

In some cases, a hard distal tip formed of the material of the outer tubular member 102 and/or intermediate tubular member 110 may injure a vessel wall or cardiac tissue. As such, it may be desirable to provide the delivery device 100 with a softer distal tip 140 that can be introduced into the anatomy and come into contact with anatomy adjacent the target cite without causing unnecessary trauma. In some cases, the distal tip 140 may be made of a material that is softer than the body portion 138 of the device containment housing 108. In some cases, the distal tip 140 may include a material that has a durometer that is less than the durometer of the material of the body portion 138. In some particular embodiments, the durometer of the material used in the distal tip 140 may be in the range of about 5 D to about 70 D, or for example, in the range of about 25 D to about 65 D. Additionally, the distal tip 140 may include a shape or structure that may make it less traumatic to tissue. For example, the distal tip 140 may have a distal surface, such as a tissue contacting surface, that is that is rounded or includes a curvature configured to be more atraumatic to tissue.

In some instances, all or a portion of the device containment housing 108 may include an inner surface that may be configured to resist getting caught on the fixation mechanism 24, such as the one or more, or a plurality of hooks or tines 26 on the implantable device 10. For example, the device containment housing 108 may include an inner layer or coating of harder or more lubricious material that resists force applied by the fixation mechanism 24 onto the inner surface of the device containment housing 108. For example, the device containment housing 108 may include a multi-layered structure, and an inner layer may be made of a material that is harder than an outer layer.

The inner tubular member 116 may be disposed (e.g., slidably disposed) within a lumen 152 of the intermediate tubular member 110. The inner tubular member 116 may be engaged by a user near or at the third hub portion 130, and extend through a lumen 152 of the intermediate tubular member 110 and into the device containment housing 108. A distal portion 118 of the inner tubular member 116 may be capable of engaging the IMD 10, and the inner tubular member 116 may be used to "push" the IMD 10 out from device containment housing 108 so as to deploy and anchor the IMD 10 within a target region (e.g., a region of the heart such as the right ventricle). The inner tubular member 116 may have a lumen 154 extending from the proximal end 117 to a distal portion 118 thereof. A tether 112 or other retaining feature may be used to releasably secure the IMD 10 to the delivery device 100. In some instances, the tether 112 may be a single or unitary length of material that may extend from a proximal end 117 of the lumen 154, out through the distal portion 118, through the opening 38 of the IMD 10 and return to the proximal end 117 of the inner tubular member 116 through the lumen 154 such that both ends of the tether 112 are positioned adjacent to the third hub portion 130. In some instances, as will be discussed in more detail below, the ends of the tether 112 may be secured within a locking feature in the third hub portion 130.

In order to more specifically place or steer the delivery device 100 to a position adjacent to the intended target, the delivery device 100 may be configured to be deflectable or articulable or steerable. Referring to FIG. 4, for example, the outer tubular member 102 and/or intermediate tubular member 110 may include one or more articulation or deflection mechanism(s) that may allow for the delivery device 100, or portions thereof, to be deflected, articulated, steered and/or controlled in a desired manner. For example, the outer tubular member 102 may include at least a portion thereof that can be selectively bent and/or deflected in a desired or predetermined direction. This may, for example, allow a user to orient the delivery device 100 such that the device containment housing 108 is in a desirable position or orientation for navigation or delivery of the IMD 10 to a target location. The outer tubular member 102 may be deflected, for example, along a deflection region.

A wide variety of deflection mechanisms may be used. In some example embodiments, deflection may be effected by one or more actuation members, such as pull wire(s) extending between a distal portion of the outer tubular member 102 and an actuation mechanism 122 near the proximal end of the outer tubular member 102. As such, the one or more pull wires may extend both proximally and distally of the desired deflection or bending region or point. This allows a user to actuate (e.g., "pull") one or more of the pull wires to apply a compression and/or deflection force to at least a portion of the outer tubular member 102 and thereby deflect or bend the outer tubular member 102 in a desired manner. In addition, in some cases the one or more wires may be stiff enough so that they can also be used to provide a pushing and/or tensioning force on the outer tubular member 102, for example, to "push" or "straighten" the shaft into a desired position or orientation.

In some embodiments, the actuation member takes the form of a continuous wire that is looped through or otherwise coupled to a distal end region of the outer tubular member 102 so as to define a pair of wire sections. Other embodiments are contemplated, however, including embodiments where the actuation member includes one or a plurality of individual wires that are attached, for example, to a metal or metal alloy ring adjacent the distal end region of the outer tubular member 102.

The actuation mechanism 122 may include a desired mechanism that may allow for applying tension (i.e. pulling force), or compression (i.e. pushing force), or both, on the actuation member(s). In some embodiments, the actuation mechanism 122 may include an external rotatable member 124 connected to and rotatable about the longitudinal axis of the handle assembly 120. The rotatable member 124 may threadingly engage an internal member that is attached to the proximal end of the actuation member(s) or pull wires. When the external rotatable member 124 is rotated in a first rotational direction, the internal member translates in a first longitudinal direction, thereby applying tension to the pull wire(s), which applies compression force to the shaft, so as to deflect the outer tubular member 102 from an initial position to a deflected position. When the external rotatable member 124 is rotated in a second rotational direction, the internal member translates in a second longitudinal direction, thereby reducing and/or releasing the tension on the pull wire(s), and allowing the outer tubular member 102 to relax back toward the initial position. Additionally, in some cases, as mentioned above, where the one or more wires may be stiff enough, rotation of the rotatable member 124 in the second rotational direction such that the internal member translates in a second longitudinal direction may apply compression to the wire(s), such that the wire(s) may apply tension to the outer tubular member 102 and "push" the outer tubular member 102 back toward an initial position, and possibly into additional positions beyond the initial position.

The one or more articulation and/or deflection mechanism(s) may also entail the outer tubular member 102 including structure and/or material that may provide for the desired degree and/or location of the deflection when the compressive or tensile forces are applied. For example, the outer tubular member 102 may include one or more sections that include structure and/or material configured to allow the shaft to bend and/or deflect in a certain way when a certain predetermined compressive and/or tensile force is applied. For example, the shaft may include one or more sections that are more flexible than other sections, thereby defining a bending or articulating region or location. Some such regions may include a number of varying or changing flexibility characteristics that may define certain bending shapes when predetermined forces are applied. Such characteristics may be achieved through the selection of materials or structure for different sections of the outer tubular member 102.

In other embodiments, other articulation and/or deflection mechanism(s) are contemplated. For example, all or a portion of the delivery device 100, such as the outer tubular member 102, may be made of a shape memory material, such as a shape memory polymer and/or a shape memory metal. Such materials, when stimulated by an actuation mechanism, such as a change in temperature or the application of an electrical current, may change or move from a first shape to a second shape. As such, these material and mechanism may be used to deflect or bend the outer tubular member 102 in a desired manner. Other suitable deflection mechanism(s) that are able to deflect the delivery device 100 may also be used. Such alternative mechanisms may be applied to all other embodiments shown and/or discussed herein, and others, as appropriate.

Furthermore, the outer tubular member 102 may include one or more predefined or fixed curved portion(s) along the length thereof. In some cases, such curved sections may be configured to fit with particular anatomies or be configured for better navigation or delivery of the IMD 10. Additionally, or alternatively, some such curved sections may be configured to allow the outer tubular member 102 to be predisposed to be bent and/or deflected in a certain direction or configuration when compression and/or tension forces are applied thereto. In some cases, the outer tubular member 102 may be a laser cut metallic tubing, a braid reinforced polymeric tubing, or other flexible tubular structure as desired.

Returning again to FIG. 5, the device containment housing 108 may be affixed to a distal end portion 114 of the intermediate tubular member 110. The device containment housing 108 may include a hub portion 136 and a tubular body portion 138. In some instances, the hub portion 136 may be formed from a metal or metal alloy while the body portion 138 may be formed from a polymeric material, although this is not required. In some instances, a proximal region 143 of the body portion 138 may be heat bonded to a distal end portion 137 of the hub portion 136, or otherwise affixed. The hub portion 136 may include a tapered intermediate region 145 disposed between a proximal end portion 139 and the distal end portion 137.

In some cases, the outer tubular member 102 may include a metal ring or tip adjacent the distal end 103 thereof for attaching one or more pull wires thereto. In some cases, the outer tubular member 102 may further include a lubricious liner, such as, but not limited to a polytetrafluoroethylene (PTFE) liner. The proximal end portion 139 of the hub portion 136 may extend proximally into the lumen 150 of the outer tubular member 102. In some instances, an outer surface of the proximal end portion 139 may form an interference fit with an inner surface of the outer tubular member 102. In some cases, the outer surface of the proximal end portion 139 and the inner surface of the outer tubular member 102 may be coupled in a tapered engagement. For example, the distal end 103 of the outer tubular member 102 may flare radially outwards in the distal direction and/or the proximal end portion 139 may taper radially inward in the proximal direction. The two angled surfaces may engage as the proximal end portion 139 is proximally retracted within the outer tubular member 102. Other coupling arrangements may be used as desired.

In some cases, as the outer tubular member 102 is bent to navigate the IMD 10 to the desired location, the proximal end portion 139 may advance distally and disengage from the inner surface of the outer tubular member 102 creating a kink point or weakened region adjacent to the bonding region 146. Proximally retracting the intermediate tubular member 110 to bring the intermediate region 145 into contact with the outer tubular member 102 at contact point 148 and/or bringing the proximal end portion 139 into the outer tubular member 102 and fixing the intermediate tubular member 110 in this configuration may help prevent migration of the device containment housing 108 during navigation of the delivery device 100 to the desired location. Such a configuration may also place the intermediate tubular member 110 in tension while the device containment housing 108 applies a compression force on the outer tubular member 102, as will be discussed in more detail below. As discussed above, a locking mechanism 132 in the handle assembly 120 may be utilized to releasably maintain the outer tubular member 102 and the intermediate tubular member 110 in a desired orientation.

Figure 6:
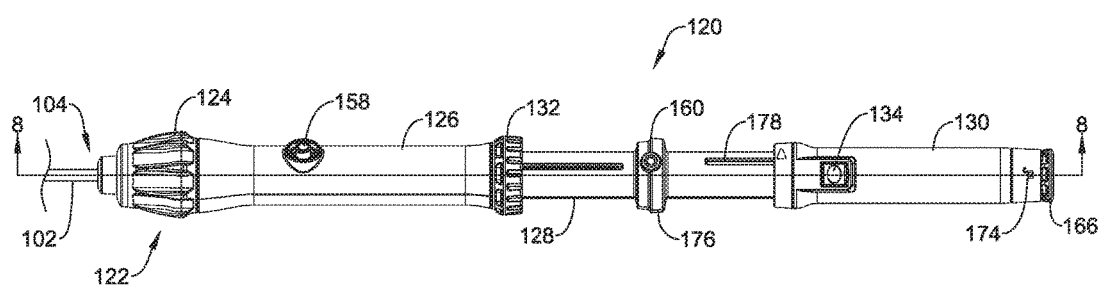
FIG. 6 is a top view of the handle of the illustrative delivery device of FIG. 4.
Figure 7:
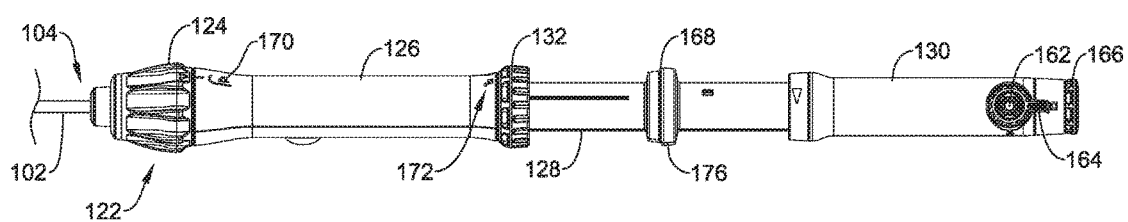
FIG. 7 is a bottom view of the handle of the illustrative delivery device of FIG. 4.

FIG. 6 illustrates a top view of the handle assembly 120 of the delivery device 100. FIG. 7 illustrates a bottom view of the handle assembly, approximately 180° from the view shown in FIG. 6. The handle assembly 120 may include one or more ports 158, 160, 162 for delivering fluids, such as, but not limited to, a contrast and/or flushing fluid to the cavity 142 of the device containment housing 108. The flush ports 158, 160, 162 may be in fluid communication with the lumens 150, 152, 154 of the outer, intermediate or inner tubular members 102, 110, 116, as desired. For example, the flush port 158 may be in fluid communication with the lumen 150 of the outer tubular member 102, the flush port 160 may be in fluid communication with the lumen 152 of the intermediate tubular member 110, and the flush port 162 may be in fluid communication with the lumen 154 of the inner tubular member 116.

The handle assembly 120 may further include a tether lock 164. The tether lock 164 may be actuatable between a locked and an unlocked configuration to maintain the tether 112 in a desired orientation. The ends of the tether 112 may affixed to, secured to, or otherwise engage a tether cap 166 positioned at a proximal end of the third hub portion 130. The tether cap 166 may be removably secured to the third hub portion 130 to allow a clinician access to the ends of the tether 112. When the tether lock 164 is in the locked configuration, the tether cap 166 may not be removed from the third hub portion 130. When the tether lock 164 is in the unlocked configuration, the tether cap 166 may be removed and the ends of the tether 112 may be actuated. For example, once the IMD 10 has been implanted and its location verified, the tether 112 may be removed from the tether retention feature 36 of the IMD 10 by pulling on one of the ends until the opposite end has passed through the opening 38 such that the IMD 10 is free from the tether 112.

In some instances, the handle assembly 120 may also include visual markings, such as, but not limited to the markings illustrated at 170, 172, 174. These markings 170, 172, 174 may provide visual instructions or indications to the clinician. For example, the marking shown at 170 may be positioned proximate the rotatable member 124 of the actuation mechanism 122 to indicate that the rotatable member 124 controls deflection of the outer tubular member 102 and/or to indicate which direction the distal section 106 will deflect when the rotatable member 124 of the actuation mechanism 122 is rotated in a given direction. The markings shown at 172 may provide an indication of whether the second locking mechanism 132 is in the unlocked and/or locked configuration. Similarly, the markings shown at 174 may provide an indication of whether the tether lock 164 is in the unlocked and/or locked configuration.

Figure 8:
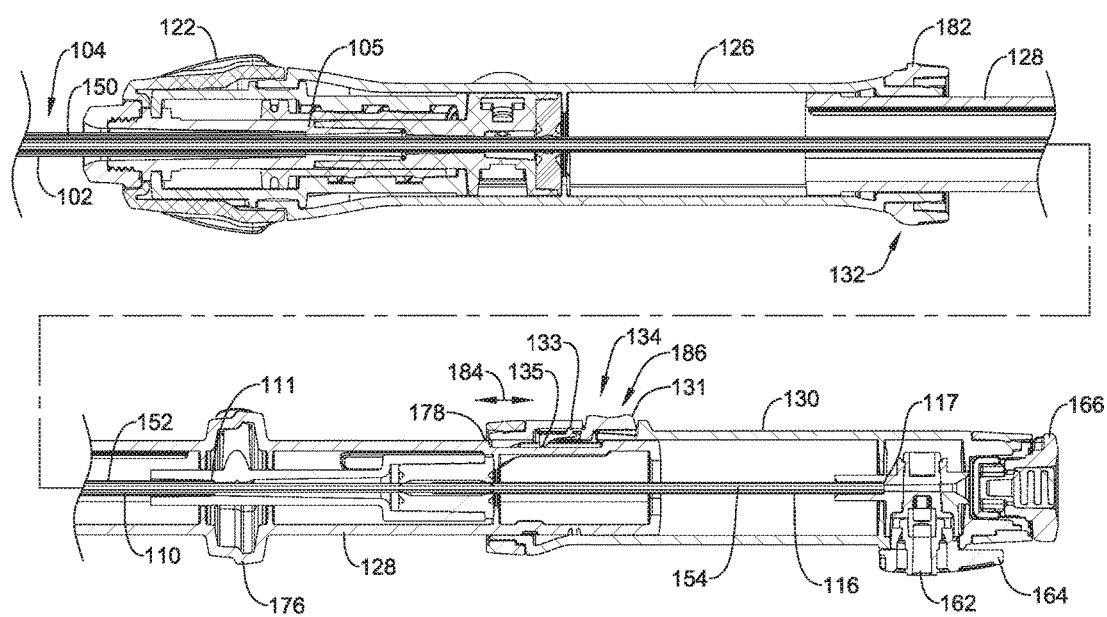
FIG. 8 is a cross-section view of the handle of the illustrative delivery device of FIG. 4 taken at line 8-8 in FIG. 6.

FIG. 8 illustrates a cross-sectional view of the handle assembly 120 of the delivery device. As discussed above, the handle assembly 120 may include a first hub portion 126 attached to the proximal end section 104 of the outer tubular member 102, a second hub portion 128 attached to a proximal end section of the intermediate tubular member 110, and a third hub portion 130 attached to a proximal end section of the inner tubular member 116. Each of the first hub portion 126, the second hub portion 128, and the third hub portion 130 may be slidable and rotatable relative to each other such that the outer tubular member 102, intermediate tubular member 110, and inner tubular member 116 may be individually longitudinally actuated.

The inner tubular member 116 may extend distally from a proximal end 117. The proximal end 117 of the inner tubular member 116 may be positioned within or adjacent to the tether lock 164. The tether lock 164 may include a port 162 which may be in fluid communication with a lumen 154 of the inner tubular member 116. The lumen 154 may extend from the proximal end 117 to the distal portion 118 for delivering fluids, such as, but not limited to, a contrast and/or flushing fluid to the cavity 142 of the device containment housing 108. In some instances, the inner tubular member 116 may be coupled or affixed to the third hub portion 130 adjacent the proximal end 117 of the inner tubular member 116, although this is not required. In some cases, the inner tubular member 116 may be affixed to the third hub portion 130 at any longitudinal location desired. In some instances, a tether, such as tether 112, for securing the IMD 10 to the distal portion 118 of the inner tubular member 116 may be disposed within the lumen 154 and may exit the delivery device 100 through or adjacent to tether cap 166, although this is not required.

The intermediate tubular member 110 may extend distally from a proximal end 111. The proximal end 111 of the intermediate tubular member 110 may be positioned within the second hub portion 128. The intermediate tubular member 110 may include a lumen 152 extending from the proximal end 111 to a distal end of the intermediate tubular member 110. The inner tubular member 116 may be slidably disposed within the lumen 152 of the intermediate tubular member 110. In some instances, the intermediate tubular member 110 may be coupled or affixed to the second hub portion 128 adjacent the proximal end 111 of the intermediate tubular member 110, although this is not required. In some cases, the intermediate tubular member 110 may be affixed to the second hub portion 128 at any longitudinal location desired.

The outer tubular member 102 may extend distally from a proximal end 105. The proximal end 105 of the outer tubular member 102 may be positioned within the first hub portion 126. The outer tubular member 102 may include a lumen 150 extending from the proximal end 105 to a distal end 103 of the outer tubular member 102. The intermediate tubular member 110 may be longitudinally slidably disposed within the lumen 150 of the outer tubular member 102. In some instances, the outer tubular member 102 may be coupled or affixed to the first hub portion 126 adjacent the proximal end 105 of the outer tubular member 102, although this is not required. In some cases, the outer tubular member 102 may be affixed to the first hub portion 126 at any longitudinal location desired.

In some instances, the first hub portion 126 may include a retaining ring 182 positioned adjacent to a proximal end of the first hub portion 126. In some instances, the retaining ring 182 may be rotatable about a longitudinal axis of the handle assembly 120. In some cases, the retaining ring 182 may include locking features configured to engage with other locking features of the locking mechanism 132. When the retaining ring 182 engages other features of the locking mechanism 132, longitudinal movement of the first hub portion 126 and the second hub portion 128 relative to one another may be prevented. Rotating the retaining ring 182 may disengage the retaining ring 182 from the other features of the locking mechanism 132. This may allow for longitudinal movement of the first hub portion 126 and the second hub portion 128 relative to one another, as will be described in more detail below. While the second locking mechanism 132 is described as a rotating retaining ring 182, other locking mechanisms capable of releasably securing first hub portion 126 and the second hub portion 128, and thus the outer tubular member 102 and the intermediate tubular member 110, may be used.

In some instances, the first locking mechanism 134 may include a depressible button 131. The depressible button 131 may include a first outwardly protruding portion 133 configured to engage a region of the third hub portion 130 and a second inwardly protruding portion 135 configured to engage a region of the second hub portion 128. For example, the second protruding portion 135 may be disposed in and engage a groove or recess 178 formed in the second hub portion 128. The engagement of the first locking mechanism 134 may prevent or reduce relative movement of the second hub portion 128 and the third hub portion 130 when the first locking mechanism 134 is not actively actuated (e.g. depressed) by a clinician. A downward force 186 may be applied to the button 131. The force 186 may cause the first protruding portion 133 to lower and/or disengage from a surface of the third hub portion 130 and the second protruding portion 135 to raise and/or disengage from a surface of the second hub portion 128. This may allow the third hub portion 130 to be moved longitudinally (e.g., proximally and/or distally), as shown at 184, along a longitudinal axis of the handle assembly 120 relative to the second hub portion 128, as will be discussed in more detail below. Longitudinal actuation of the third hub portion 130 relative to the second hub portion 128 may result in a corresponding longitudinal actuation of the inner tubular member (and hence the IMD 10) relative to the intermediate tubular member 110 and the device containment housing 108. Such actuation may be used to incrementally deploy the IMD 10. FIG. 8 illustrates the second protruding portion 135 disposed in the middle of the recess 178. However, in some cases, during advancement of the delivery device 100 to the desired treatment location, the second protruding portion 135 may be positioned at the proximal end of the recess 178 to ensure the IMD 10 is fully disposed in the device containment housing 108. This is just an example. While the first locking mechanism 134 is described as a depressible button 131, in some cases other locking mechanisms capable of releasably securing the second hub portion 128 and the third hub portion 130, and thus the intermediate tubular member 110 and the inner tubular member 116, may be used.

Figure 9:
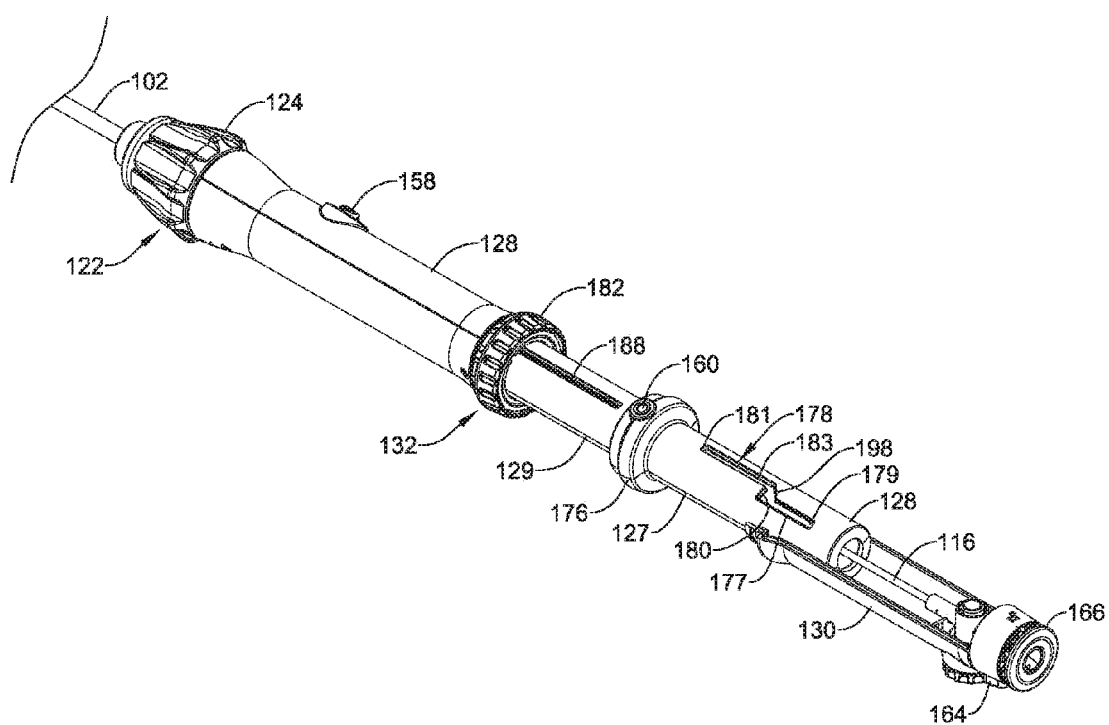
FIG. 9 is a perspective view of the handle of the illustrative delivery device of FIG. 4 with portions removed.

FIG. 9 illustrates a partial perspective view of the handle assembly 120 with portions of the third hub portion 130 removed to more clearly illustrate features of the second hub portion 128. A proximal portion 127 of the second hub portion 128 may include a groove or recess 178 formed therein. The groove 178 may extend from a proximal end 179 to a distal end 181. In some embodiments, groove 178 may include a proximal portion 177 and a distal portion 183 which may be circumferentially offset from one another. A hard stop 180 may be provided at a region between the proximal end 179 and the distal end 181. The hard stop 180 may be a wall or other protrusion configured to engage the second protruding portion 135 of the first locking mechanism 134 such that in order to advance the second protruding portion 135 distally past the hard stop 180 from the proximal portion 177, the user rotates the third hub portion 130 to align the second protruding portion 135 with the distal portion 183 of the groove 178. This may allow the implantable device 10 to be incrementally deployed. During advancement of the delivery device 100 through the vasculature, the second protruding portion 135 may be disposed within the proximal portion 177 adjacent to the proximal end 179. As discussed above, the second protruding portion 135 may engage a surface of the second hub portion 128 to prevent and/or minimize relative movement of the second and third hub portions 128, 130 relative to one another.

The groove 178 may also include an angled region 198 between the proximal portion 177 and the distal portion 183 positioned generally opposite the hard stop 180. When the third hub portion 130 is proximally retracted from the distal end 181 to the proximal end 179, the angled region 198 may guide the second protruding portion 135 from the distal portion 183 of the groove 178 to the proximal portion 177 of the groove in a single fluid movement. For example, the third hub portion 130 may be proximally retracted from the distal end 181 to the proximal end 179 relative to the second hub portion 128 in a single proximal movement, if so desired, without prohibiting travel of the second protruding portion 135 from the distal portion 183 to the proximal portion 177.

A distal portion 129 of the second hub portion 128 may include a groove or recess 188 configured to receive a mating feature disposed on the first hub portion 126. This may allow the first hub portion 126 to be proximally retracted over the second hub portion 128, as will be discussed in more detail below. The proximal and distal portions 127, 129 of the second hub portion 128 may be separated by a gripping region 176 configured to provide a region for the clinician to hold.

Figure 10A:
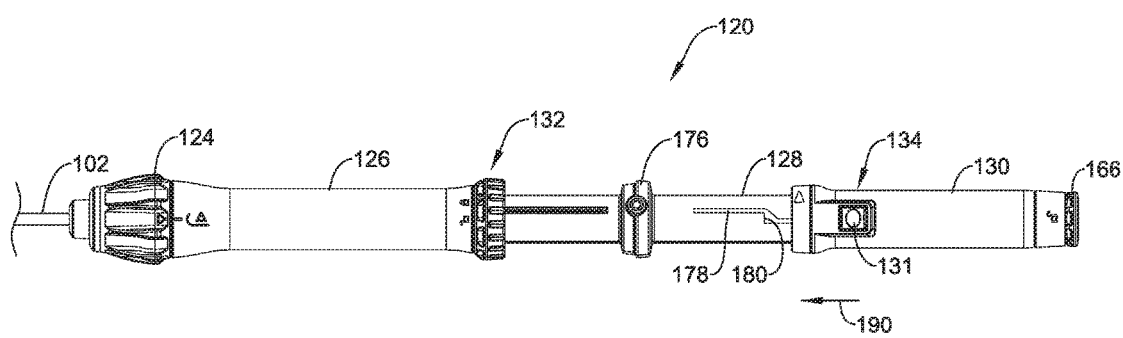
FIGS. 10A-10E are schematic views illustrating the use of the illustrative delivery device to deploy an implantable leadless cardiac pacing device.
Figure 10B:
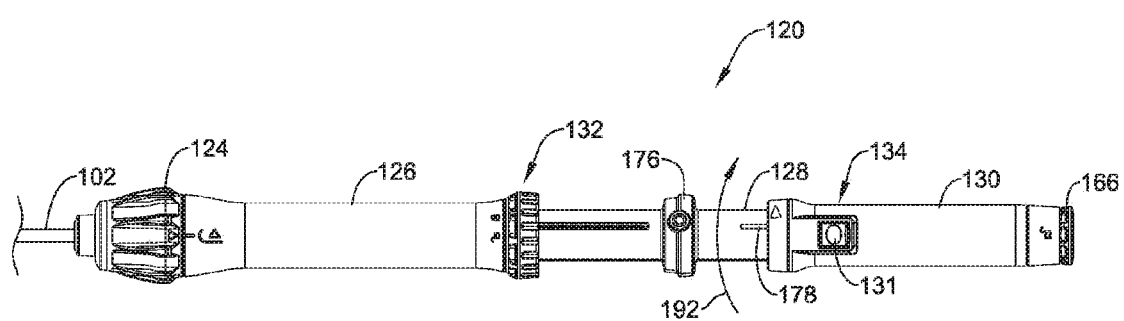

Referring now to FIGS. 10A-10E, a method for deploying an IMD 10 using the illustrative delivery device 100 will now be described. The delivery device 100 may be introduced into the vasculature through the femoral vein through a previously introduced guide catheter. This is just an example. The delivery device 100 may be introduced through any desired location and with or without the use of a guide catheter as desired. The delivery device 100 may be advanced through the vasculature to the desired treatment location, which, in the case of a leadless cardiac pacing device, may be a chamber of the heart. The clinician may use the actuation mechanism 122 may to deflect the distal section 106 of the outer tubular member 102 in a desired manner to facilitate advancement of the delivery device 100. During advancement of the delivery device 100, the handle assembly 120 may be in a fully extended configuration, as shown in FIG. 10A. In such a configuration, the third hub portion 130 may be at its proximal-most location relative to the second hub portion 128 and the first hub portion 126 may be at its distal-most location relative to the second hub portion 128. When the handle assembly 120 is in its fully extending configuration, the inner tubular member 116, intermediate tubular member 110, and the outer tubular member 102 may be oriented in the manner illustrated in FIG. 5. The delivery device 100 can be imaged using known techniques to ensure accurate placement of the IMD 10.

Figure 10C:
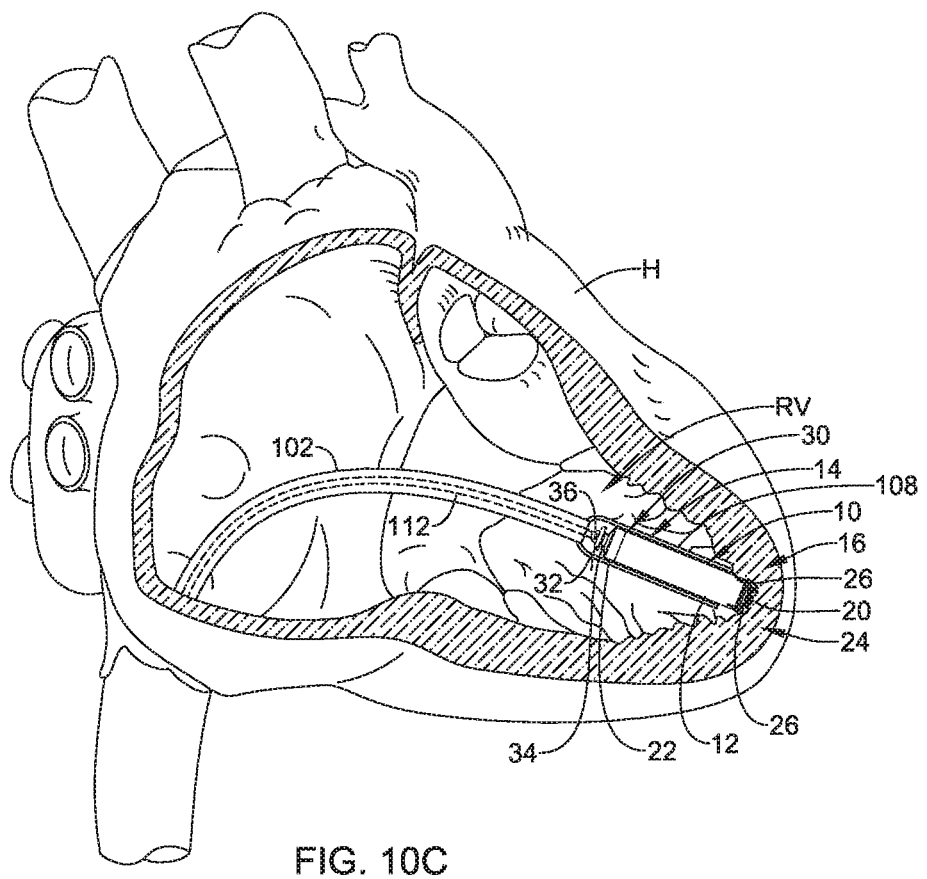
Figure 10D:
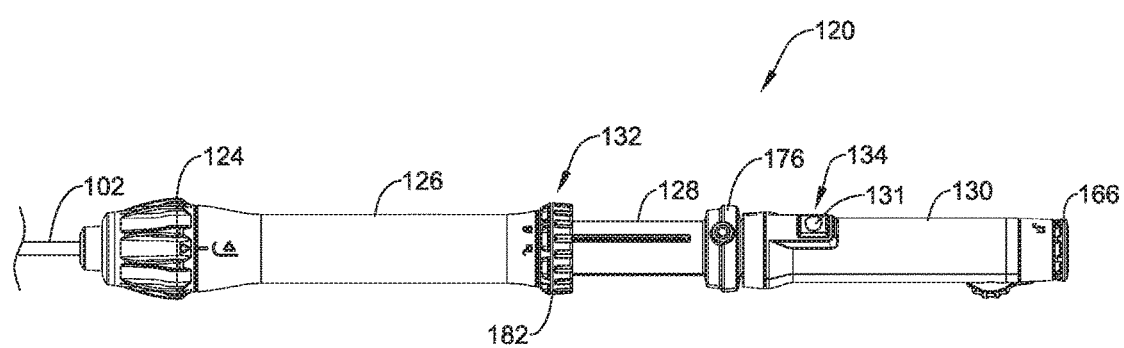

Once the distal tip portion 140 of the device containment housing 108 has been positioned adjacent to the cardiac tissue where the IMD 10 is desired, deployment of the IMD 10 can begin. The first stage of deploying the IMD 10 may enable activation of the fixation mechanism 24. To initiate the first stage of deployment, the clinician may stabilize the first hub portion 126 relative to the patient and depress the button 131 of the first locking mechanism 134. The clinician may then slide the third hub portion 130 distally, as shown at 190, until the first locking mechanism 134 engages the hard stop 180 provided in the second hub portion 128 resulting in the handle assembly 120 configuration shown in FIG. 10B. Distal actuation of the third hub portion 130 may also move the inner tubular member 116 distally by the same distance. As the inner tubular member 116 advances distally, the distal portion 118 may "push" against the proximal end 14 of the implantable device 10. As the IMD 10 is pushed distally, the hooks 26 engage the heart tissue as shown in FIG. 10C. The IMD 10 may be distally advanced out of the device containment housing 108 to deploy the hooks or tines 26 from the device containment housing 108 to engage the hooks or tines 26 in the heart tissue while the proximal portion of the IMD 10 remains within the device containment housing 108. In some instances, the IMD 10 may be advanced distally in the range of 1 to 5 millimeters, although this is merely illustrative. This may allow the IMD 10 to be deployed while minimizing the amount of pressure applied to the heart wall. Further, the first locking mechanism 134 may prevent accidental or unintentional deployment of the IMD 10 as the button 131 must be actuated while advancing the third hub portion 130.

Figure 11A:
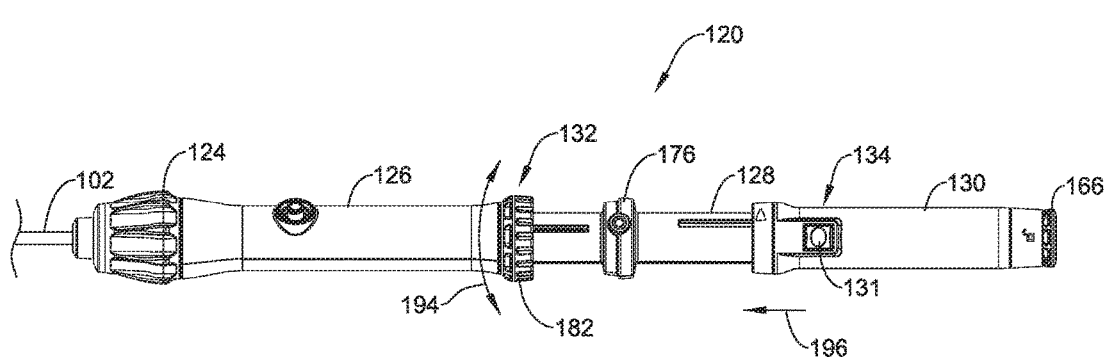
FIGS. 11A-11B are schematic views illustrating a telescoping feature of the illustrative delivery device.
Figure 11B:
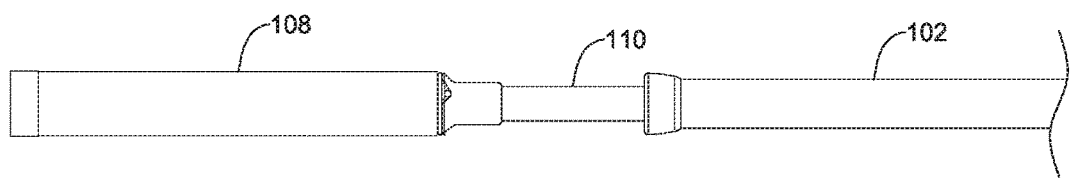

Referring briefly to FIGS. 11A and 11B, in some instances, it may be desirable to advance the device containment housing 108 and the intermediate tubular member 110 without advancing the outer tubular member 102 (i.e., telescoping the intermediate tubular member 110). For example, this may facilitate advancement of the delivery device 100 within the heart or maintain the position of the device containment housing 108 once it is placed again the heart wall. To distally advance or telescope the intermediate tubular member 110 relative to the outer tubular member 102, the second locking mechanism 132 may be actuated to "unlock" the first hub portion 126 and the second hub portion 128. As described above, a rotating retaining ring 182 may be rotated, as shown at 194, to move the second locking mechanism 132 from a locked to an unlocked configuration. Once the first locking mechanism has been unlocked, the clinician may distally advance 196 the second and third hub portions 128, 130 together to distally advance the device containment housing 108 as far as desired and/or needed. The actuation of the second and third hub portions 128, 130 may simultaneously move the intermediate tubular member 110 and the inner tubular member 116 as well. This may be done during advancement of the delivery device 100 through the vasculature, before initiating the first stage of deploying the IMD 10, and/or after the first stage of deploying the IMD 10 has been completed, as desired or needed.

After the first stage of deployment of the IMD 10, in which the tines or hooks 26 have been deployed from the device containment housing 108 into engagement with the heart wall, the tether 112 may be used to perform a tug test to determine if the IMD 10 is sufficiently engaged with the heart wall. In other words, the fixation of the IMD 10 (e.g. how well the hooks 26 are secured to the heart tissue) may be tested by gently tugging on the ends of the tether 112. If it is determined that the IMD 10 is sufficiently engaged with the heart wall, then the user may proceed to the second stage of deployment of the IMD 10 in which the remainder of the IMD 10 is expelled from the device containment housing 108. Otherwise, if the tug test fails and it is determined that the IMD 10 is not sufficiently engaged with the heart wall, the user may use the tether to pull (retract) the IMD 10, including the tines or hooks 26, back into the device containment housing 108 to release the implantable device 10 from the heart wall. The IMD 10 may then be repositioned and the first stage of deployment repeated.

Returning to FIG. 10B, the second stage of deploying the IMD 10 may proximally retract the device containment housing 108, and thus the intermediate tubular member 110, relative to the inner tubular member 116 to fully deploy the IMD 10. Once the clinician has determined that the position of the IMD 10 is satisfactory and the fixation mechanism 24 is securely engaged with the heart tissue, the intermediate tubular member 110, including the device containment housing 108, of the delivery device 100 can be proximally retracted. To initiate the second stage of the deployment, the clinician may first rotate the third hub portion 130, as shown at 192, such that the button 131 is aligned with the distal portion 183 of the groove 178. The clinician may then stabilize the third hub portion 130 relative to the patient and proximally retract the first and second hub portions 126, 128. It should be noted that while it is possible to distally actuate the third hub portion 130 at this point, this may cause additional and unnecessary forces to be applied to the heart wall. Further, such distal movement of the third hub portion 130 may move the inner tubular member 116 (and hence the implantable device 10) distally rather than proximally retracting the intermediate tubular member 110 and/or the outer tubular member 102. The first and second hub portions 126, 128 may be proximally retracted until the first locking mechanism 134 engages the distal end 181 of the groove 178, resulting in the handle assembly 120 configuration shown in FIG. 10D. Such actuation of the first and second hub portions 126, 128 may fully deploy the implantable device 10 such that the IMD 10 is exterior of the device containment housing 108 and engaged with the heart wall, as shown in FIG. 10E.

Figure 10E:
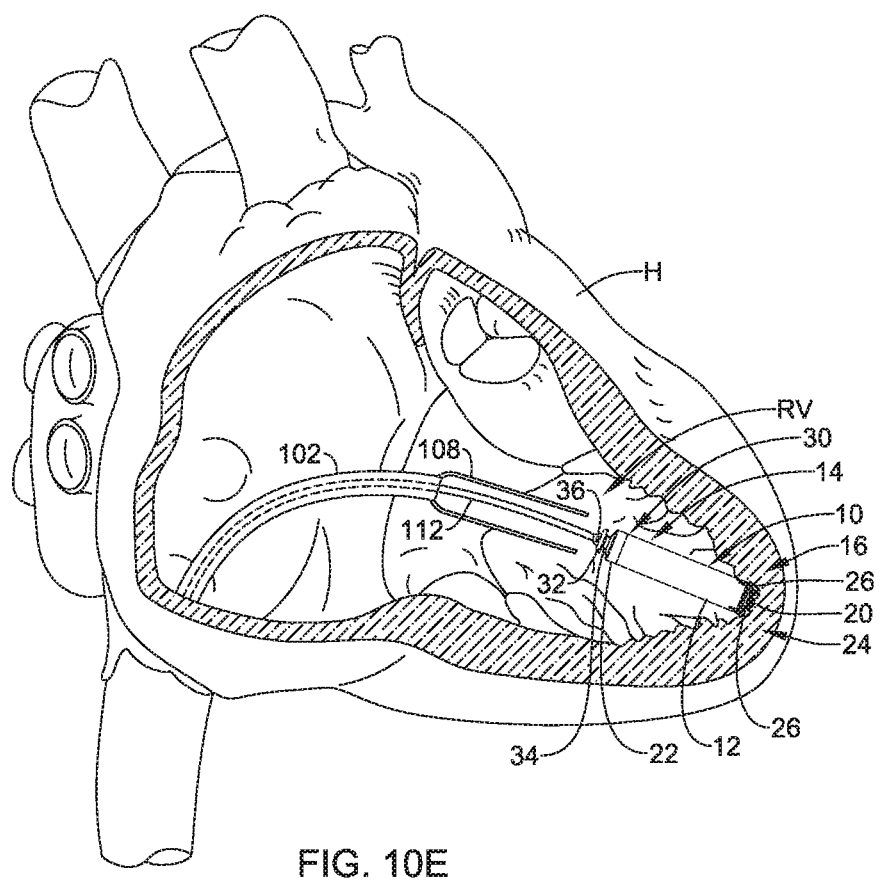

As can be seen in FIG. 10E, the IMD 10 may still be affixed to the delivery device 100 through the tether 112. Once the clinician has verified the position of the IMD 10, the fixation of the IMD 10 and/or the electrical performance of the IMD 10, the tether 112 may be removed. In some instances, fixation of the IMD 10 (e.g. how well the hooks 26 are secured to the heart tissue) may be tested by gently tugging on the ends of the tether 112. The tether 112 may be removed by unlocking the tether lock 164, removing the tether cap 166, cutting the tether 112 at some location along its length, and pulling on one of the ends until the opposite end has passed through the opening 38 of the IMD 10 such that the IMD 10 is free from the tether 112. In some instances, the tether 112 may be affixed to a portion of the tether cap 166 (e.g. creating a loop) such that the tether 112 must be cut to allow the IMD 10 to be freed from the tether 112.

Figure 12:
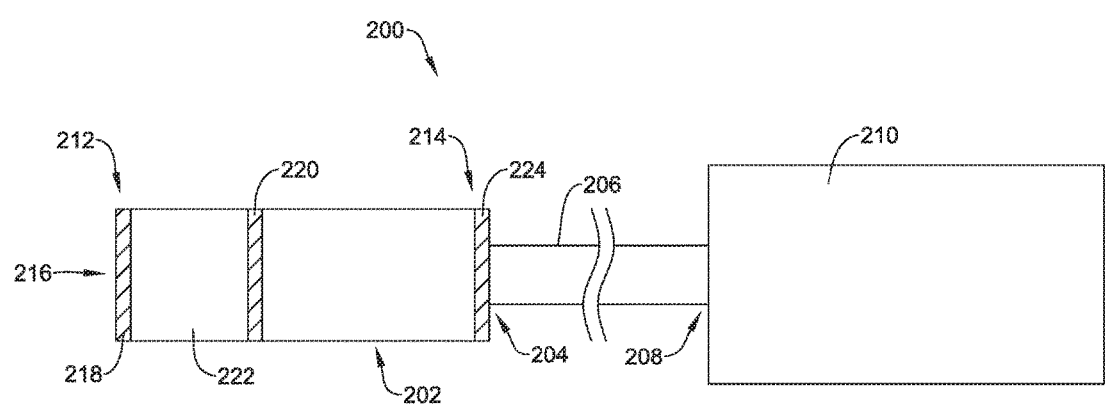
FIG. 12 is a schematic view of an illustrative delivery device.

In using the delivery device 100 to deliver the IMD 10, it may be beneficial to be able to verify that the distal end of the delivery device 100 is in adequate contact with the tissue prior to deploying the IMD 10. It will be appreciated that if there is not sufficient tissue contact, fixation of the IMD 10 may be negatively impacted. Further, in some cases application of excessive force may cause the distal end of the delivery device 100 to damage or even perforate the tissue against which the delivery device 100 is engaged. FIG. 12 provides a schematic illustration of a delivery and deployment device 200 which may, as will be appreciated, be considered as an example of the delivery device 100.

In broadest terms, as illustrated in FIG. 12, the delivery and deployment device 200 includes a device containment housing 202 that is located at a distal end 204 of a shaft 206. A handle assembly 208 may be located at a proximal end 210 of the shaft 206. In some cases, the device containment housing 202 may be considered as representing the device containment housing 108 discussed with respect to the previous Figures. In some cases, the shaft 206 may be considered as representing the outer tubular member 102 discussed above and may include one or more inner tubular members (not visible in this schematic view). In some instances, the handle assembly 208 may be considered as representing and/or including one or more of the distal hub portion 126, the intermediate hub portion 128 and the proximal hub portion 130. The device containment housing 202 has a distal end 212 and a proximal end 214. In some cases, the distal end 212 of the device containment housing 202 may be open, and the device containment housing 202 may define a void 216 therein that may be configured to accommodate an implantable medical device (such as but not limited to the IMD 10).

In some cases, the device containment housing 202 includes a first position indicator 218 that is located at or near the distal end 212 of the device containment housing 202. In some cases, the device containment housing 202 includes a second position indicator 220 that is located proximally of the first position indicator 218. In some embodiments, a compressible region 222 may be located at least partially between the first position indicator 218 and the second position indicator 220. In some instances, the compressible region 222 may be entirely located between the first position indicator 218 and the second position indicator 220. In some cases, the compressible region 222 may not be entirely located between the first position indicator 218 and the second position indicator 220 and may, for example, extend proximally beyond the second position indicator 220. When a force having an axial component is applied to the distal end 212 of the device containment housing 202, such as when the device containment housing 202 contacts cardiac or other tissue, the compressible region 222 may compress by an amount that is proportional or otherwise related to the applied force. As a result of the compression, a distance between the first position indicator 218 and the second position indicator 220 may change. The amount that the distance between the first position indicator 218 and the second position indicator 220 changes may be proportional or otherwise related to the applied force.

In some cases, the first position indicator 218 and the second position indicator 220 may be configured to be visible via an imaging process such as fluoroscopy, particularly as in some cases implantable devices such as the IMD 10 may be guided to the intended destination under fluoroscopy. For example, in some cases, the first position indicator 218 may be a first radiopaque marker band and the second position indicator 220 may be a second radiopaque marker band. By watching a distance between the first position indicator 218 and the second position indicator 220 change during deployment, the person advancing the delivery and deployment device 200 may be able to determine if they are applying sufficient force while not applying excessive force.

In some instances, the first position indicator 218 may be a first electrode and the second position indicator 220 may be a second electrode. In some cases, the first position indicator 218 and/or the second position indicator 220 may each independently be ring electrodes. It will be appreciated that as the distance between the first position indicator 218 and the second position indicator 220 changes, an impedance value between the first position indicator 218 and the second position indicator may change. Accordingly, the changing impedance value may be used to ascertain how much force has been applied to the distal end 212 of the device containment housing 202. In some cases, the device containment housing 202 may include a third electrode 224. While the third electrode 224 is schematically illustrated as being located at the proximal end 214 of the device containment housing 202, it will be appreciated that in some cases the third electrode 224 may be located elsewhere on the device containment housing 202, be located on the shaft 206, or be absent. In some cases, when the a sufficient amount of force is applied, a first audible and/or tactile feedback may be provided to the user, and if too much force is applied, a second audible and/or tactile feedback may be provided to the user.

Figure 13:
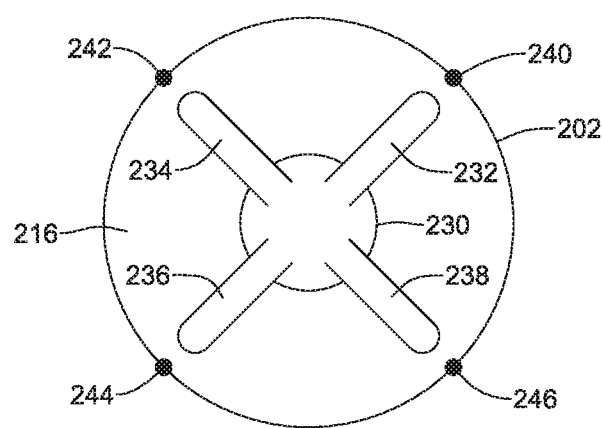
FIG. 13 is an end-view of the delivery device of FIG. 12, illustrating an implantable device in the device containment housing.

In some cases, the first position indicator 218 may not be a single electrode such as a ring electrode, but may instead be a plurality of electrodes. FIG. 13 is a schematic end view looking from the distal end and into the device containment housing 202. FIG. 13 shows an implantable medical device (IMD) 230 disposed within the void 216 defined by the device containment housing 202. The IMD 230 may, for example, be considered as being representative of the IMD 10. As illustrated, the example IMD 230 includes a total of four anchoring talons 232, 234, 236 and 238, although in some cases the IMD 230 may have more than four anchoring talons or in some instances may have fewer than four anchoring talons, or may have a different fixation mechanism altogether.

In some cases, the device containment housing 202 may include a first electrode 240 that may be at least substantially aligned with the anchoring talon 232, a second electrode 242 that may be at least substantially aligned with the anchoring talon 234, a third electrode 244 that may be at least substantially aligned with the anchoring talon 236, and/or a fourth electrode 246 that may be at least substantially aligned with the anchoring talon 238. It will be appreciated that one or more of the electrodes 240, 242, 244, 246 may be used as the first position indicator 218, in combination with another electrode functioning as the second position indicator 220, to provide an indication of the force being applied to the distal end 212 of the device containment housing 202 as a result of the distal end 212 of the device containment housing 202 contacting tissue such as cardiac tissue.

It will be appreciated that in many cases, tissue such as cardiac tissue does not present a simple, planar surface. It may be useful to be able to determine which portion or portions of the distal end 212 of the device containment housing 202 may be in good tissue contact as this may provide an indication of how well one or more individual talons 232, 234, 236 and 238 may fixate within the tissue. As the talons 232, 234, 236 and 238 exit the device containment housing during deployment, it can be desirable to have the distal end 212 of the device containment housing 202 at each of the talons in contact with the cardiac tissue so that each of the talons 232, 234, 236 and 238 advance into the cardiac tissue (see FIG. 5) before curling back to fix the IMD to the heart (see FIG. 10C).

In some cases, the electrodes 240, 242, 244, 246 may individually be utilized, sometimes in combination with another electrode such as the electrode forming the second position indicator 220 or perhaps the third electrode 224, to determine if the aforementioned electrode 240, 242, 244, 246 is in contact with tissue, which may give an indication of whether the corresponding talon 232, 234, 236, 238 might be well-positioned to engage tissue when the IMD 230 is subsequently deployed. If not, a different location may be investigated, or the device containment housing 202 may be rotated before checking again. It is best to have all four talons 232, 234, 236, 238 properly engage tissue.

Figure 14A:
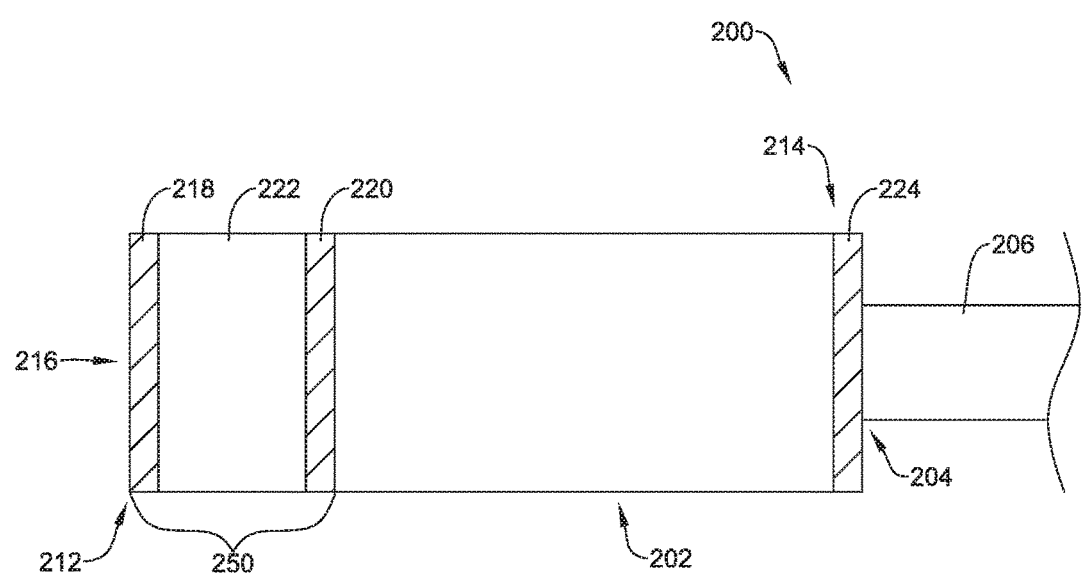
FIGS. 14A-14C are schematic views of the distal portion of the delivery device of FIG. 12.
Figure 14B:
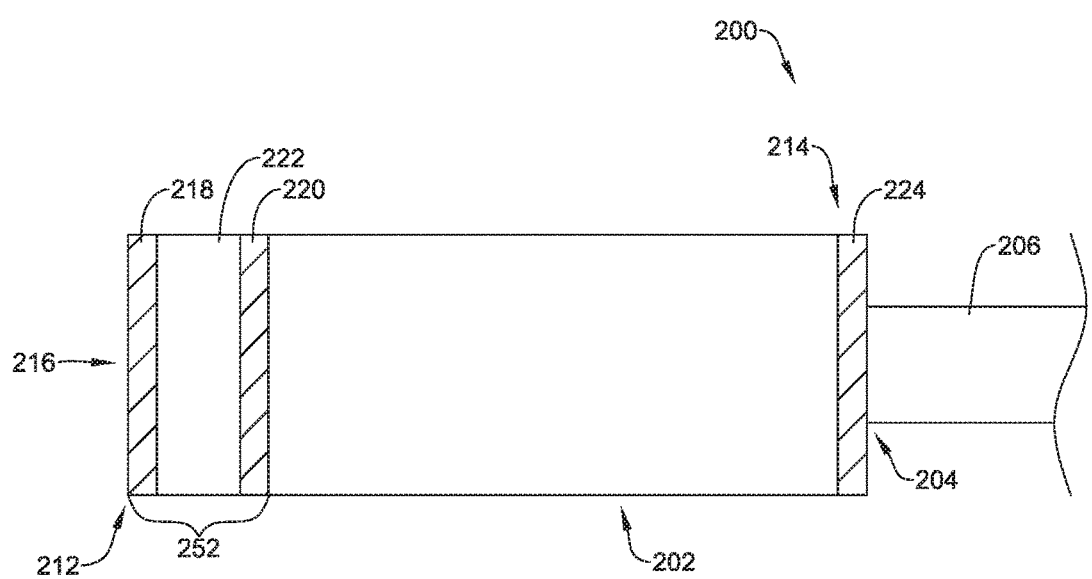
Figure 14C:
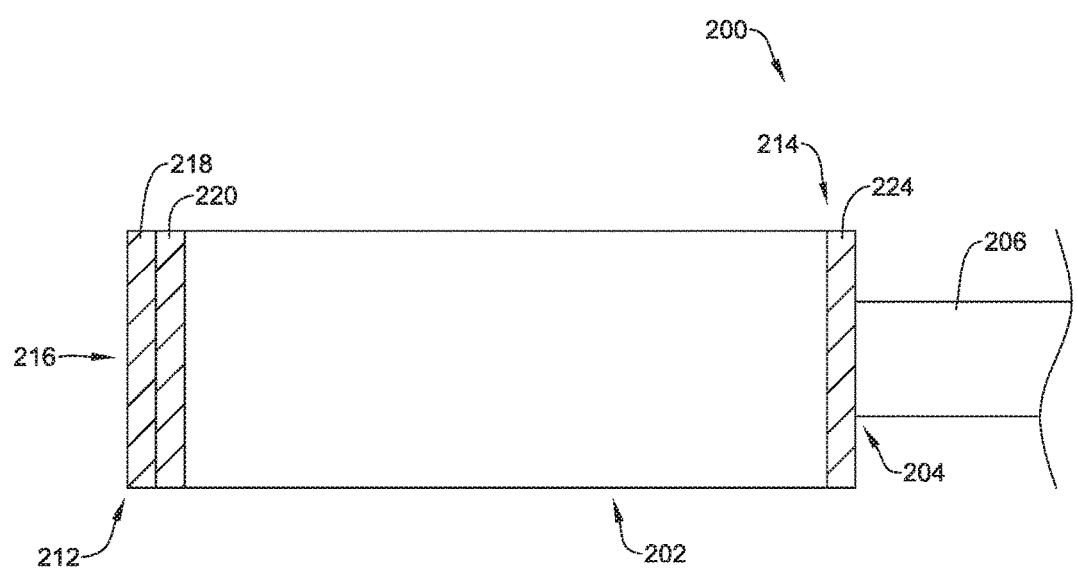

FIGS. 14A-14C provide a closer view of the illustrative device containment housing 202. FIG. 14A represents a starting point with respect to the first position indicator 218 and the second position indicator 220, such as may occur prior to the distal end 212 of the device containment housing 202 contacting tissue such as cardiac tissue. In FIG. 14A, there is a distance 250 between the first position indicator 218 and the second position indicator 220. Moving to FIG.

14B, there is a distance 252 between the first position indicator 218 and the second position indicator 220. In some cases, there may, for example, be a linear relationship between a forced applied to the distal end 212 of the device containment housing 108, which may provide an easily recognized relationship between the applied force and the corresponding change in distance between the distance 250 and the distance 252. In some cases, there may be a non-linear relationship between applied force and a change in distance between the first position indicator 218 and the second position indicator 220. In such cases, there may be a calibration step during manufacturing, for example, to determine the non-linear relationship.

It will be appreciated that the distance 252 is less than the distance 250 and the distance 252 is greater than zero. In some cases, the distance 252 may, for example, correspond to a desired compression of the compressible region 222, thereby indicating an appropriate amount of force being applied by virtue of the distal end 212 of the device containment housing 202 contacting tissue such as cardiac tissue. FIG. 14C illustrates what may happen if too much force has been applied. In FIG. 14C, the second position indicator 220 has moved much closer to the first position indicator 218 and may actually be in contact with the first position indicator 218 and/or the compressible region 222 has reached its fully compressed state. In the example of FIG. 14C, there is no visible distance between the first position indicator 218 and the second position indicator 220. It is contemplated that the compressible region 222 may be designed such that when the second position indicator 220 is in the intermediate state shown in FIG. 14B, an adequate yet safe force is being applied by the device containment housing to the contacting tissue.

Figure 15A:
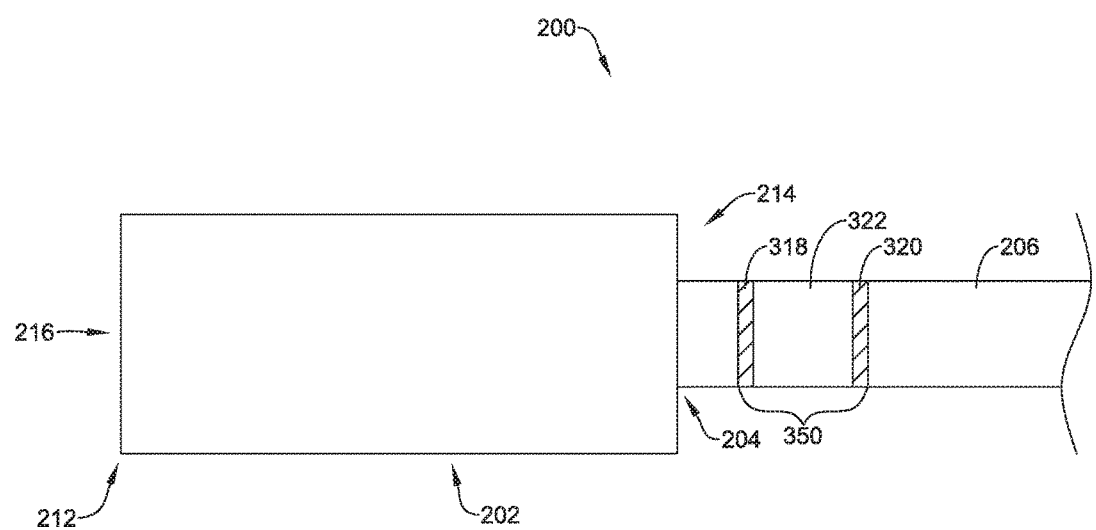
FIGS. 15A-C are schematic views of the distal portion of the delivery device of FIG. 12.
Figure 15B:
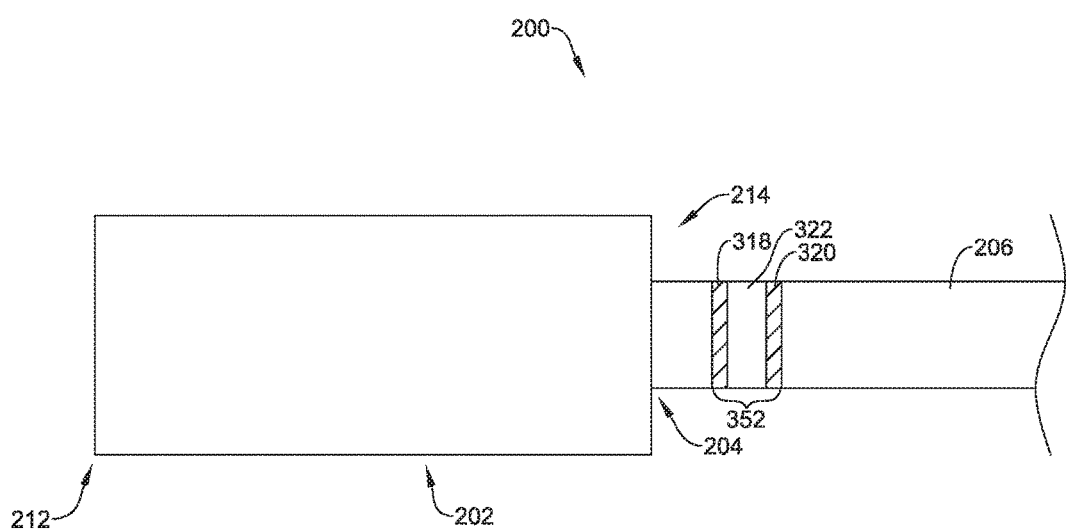
Figure 15C:
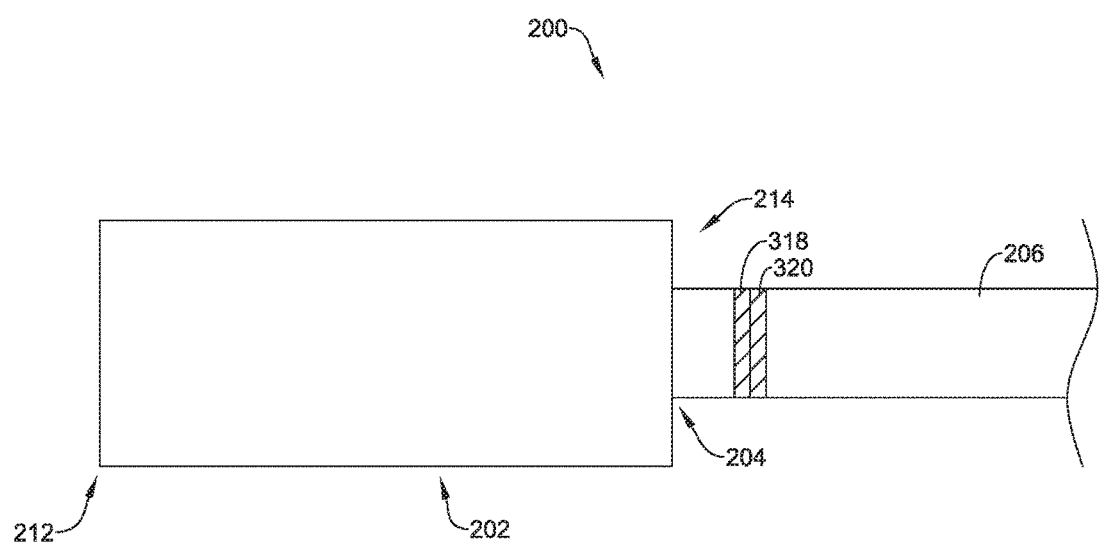

In some embodiments, the first position indicator 218 and the second position indicator 220 may not be disposed on the device containment housing 202, as shown in FIGS. 14A-C, but may instead be located on the shaft 206, at or near the distal end 204 of the shaft 206. FIGS. 15A-15C illustrate a changing distance between a first position indicator 318 and the second position indicator 320 when both are disposed on the shaft 206. FIG. 15A represents a starting point with respect to the first position indicator 518 and the second position indicator 520, such as may occur prior to the distal end 212 of the device containment housing 202 contacting tissue such as cardiac tissue. In FIG. 15A, there is a distance 350 between the first position indicator 318 and the second position indicator 320. Moving to FIG. 15B, there is a distance 352 between the first position indicator 318 and the second position indicator 320. It will be appreciated that the distance 352 is less than the distance 350 and the distance 352 is greater than zero. In some cases, the distance 352 may, for example, correspond to a desired compression of the compressible region 322, thereby indicating an appropriate amount of force being applied by virtue of the distal end 212 of the device containment housing 202 contacting tissue such as cardiac tissue. FIG. 15C illustrates what may happen if too much force has been applied. In FIG. 15C, the second position indicator 320 has moved much closer to the first position indicator 318 and may actually be in contact with the first position indicator 318 and/or the compressible region 322 has reached its fully compressed state. In FIG. 15C, there is no visible distance between the first position indicator 318 and the second position indicator 320. It is contemplated that the compressible region 322 may be designed such that when the second position indicator 320 is in the intermediate state shown in FIG. 15B, an adequate yet safe force is being applied by the device containment housing to the contacting tissue.

Figure 16A:
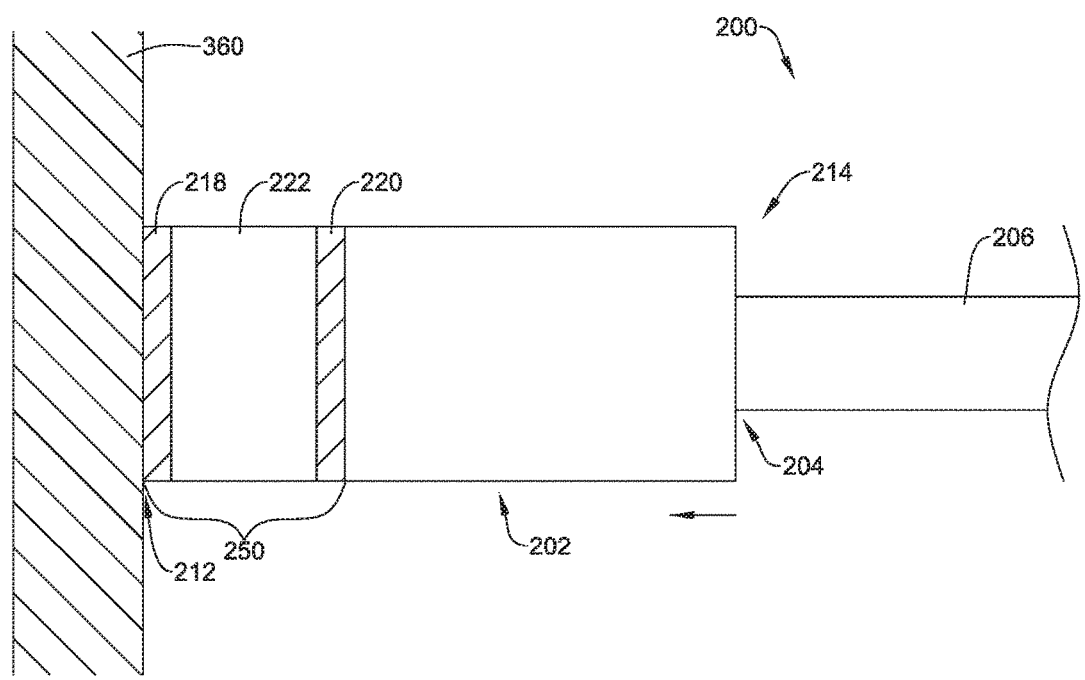
FIGS. 16A-C are schematic views showing the distal portion of the delivery device of FIG. 12 contacting tissue.
Figure 16B:
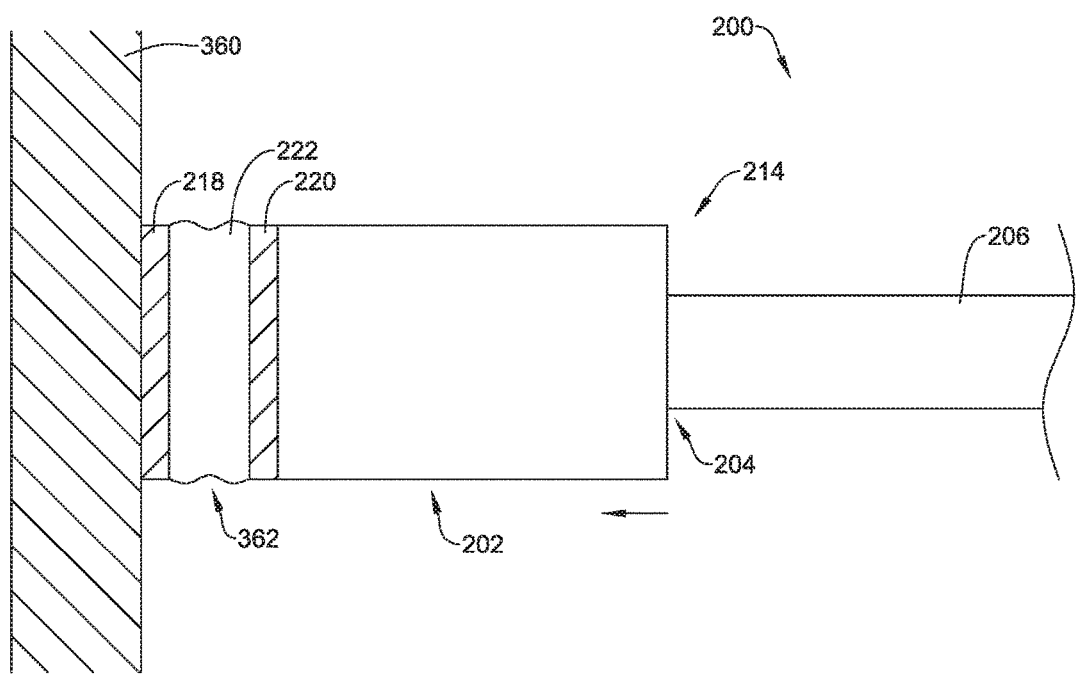
Figure 16C:
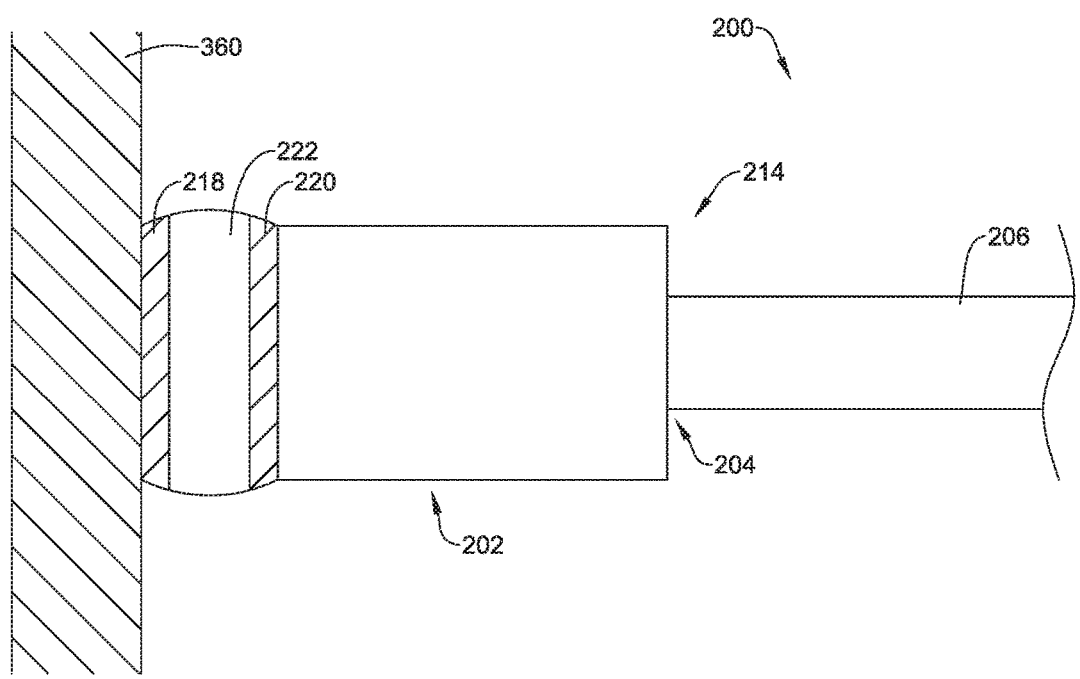

It will be appreciated that there are multiple ways as to how the compressible region 222, 322 may compress in response to an applied force. FIG. 16A illustrates the device containment housing 202 in position against tissue 360. In some cases, the tissue 360 may be cardiac tissue such as a ventricular wall, but this is not required. This represents a starting point, much like that shown in FIG. 14A, in which essentially no force has been applied to the device containment housing 202, as indicated by the distance 250 between the first position indicator 218 and the second position indicator 220. FIGS. 16B and 16C provide enlarged views of the device containment housing 202, showing several illustrative but non-limiting examples of how the compressible region 222 may compress during use. In FIG. 16B, the compressible region 222 forms an accordion region 362 in which the side wall of the device containment housing 202 forms an undulating wave form. In FIG. 16C, the compressible region 222 forms a bulged or billowed region 364 in which the side wall of the device containment housing 202 distends outwardly as a result of an applied force. In either case, the relative change in distance between the first position indicator 218 and the second position indicator 220 may provide an indication of how much force is being applied. In some cases, the compressible region 222 may include a spring sometimes incorporated into a weave, may include a compressible material, and/or may otherwise be constructed to provide a predictable and appropriate compression force versus compression distance profile. The compressible region 222 may be considered a force sensor.

In some cases, the delivery and deployment device 200 (or the delivery device 100) may include one or more force sensors that may, for example, provide an indication of a force being applied to the IMD 10 during deployment of the IMD 10. In some cases, for example, one or more force sensors that provide an indication of forces (compressive or tensile) applied to the IMD 10 during or after deployment of the IMD 10 may be used in addition to the previously described first and second position indicators that indicate forces applied to the device containment housing 108. In some cases, one or more force sensors that provide an indication of forces (compressive or tensile) applied to the IMD 10 during or after deployment of the IMD 10 may be used instead of measuring or otherwise indicating forces applied to the device containment housing 108. For example, in some instances, it is contemplated that the IMD 10 may be implanted using an implantation structure lacking the device containment housing 108.

Figure 17:
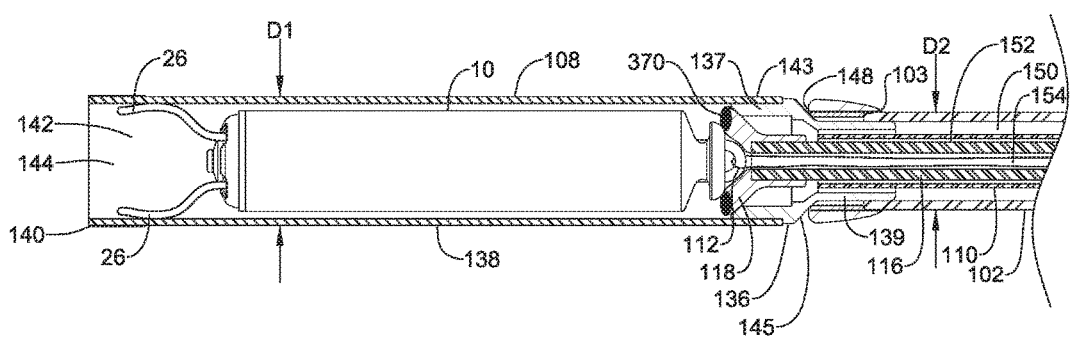
FIG. 17 is a schematic view of the distal portion of the delivery device of FIG. 12.
Figure 18:
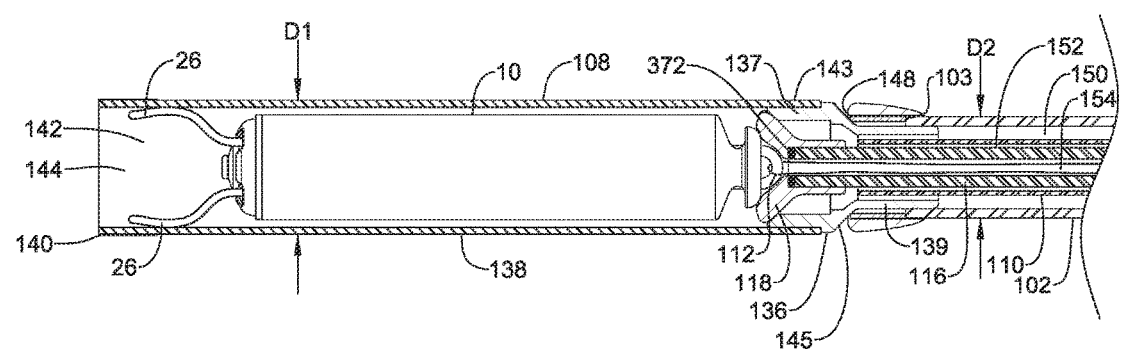
FIG. 18 is a schematic view of the distal portion of the delivery device of FIG. 12.
Figure 19:
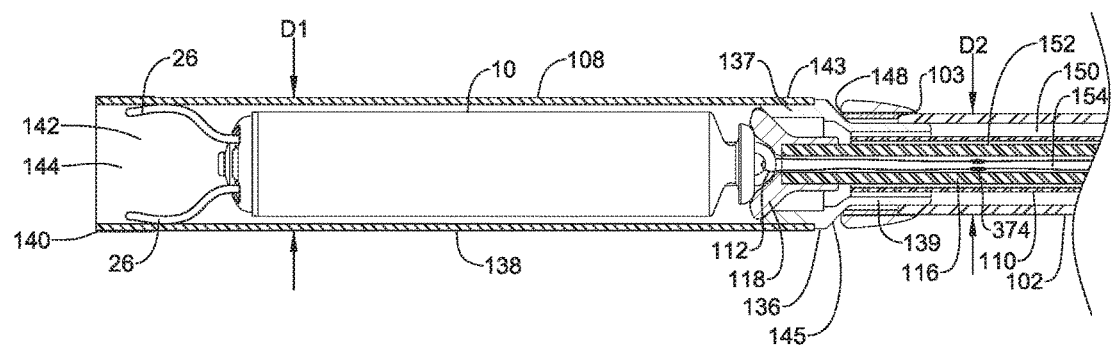
FIG. 19 is a schematic view of the distal portion of the delivery device of FIG. 12.

In some cases, the delivery and deployment device 200 (or the delivery device 100) may include one or more force sensors that may, for example, provide an indication of a tensile force being applied to the IMD 10 during a post-deployment tug test. FIGS. 17-19 are similar to FIG. 5 but provide illustrative but non-limiting examples of where such force sensors may be disposed within or near the device containment housing 108.

In FIG. 17, a force sensor 370 may be seen attached or otherwise disposed on the distal portion 118 of the inner tubular member 116 which, as discussed, may be used to engage and push the IMD 10 out of the device containment housing 108 during deployment of the IMD 10. FIG. 18 is similar, but illustrates a force sensor 372 that is attached to or otherwise disposed on the inner tubular member 116. The force sensors 370 and 372 may be any desired type of force sensor that may provide a signal representative of the force being applied to the IMD 10. FIG. 19 provides an illustrative but non-limiting example of a force sensor 374 that may be attached to, or form a portion of, the tether 112. The force sensor 374 may, for example, be a strain gauge and thus may provide an indication of the force applied to the IMD 10 via the tether 112 during a tug test after deployment, such as that illustrated in FIG. 10E. In some cases, the strain gauge may be a fiber optic or piezo type strain sensor.

Figure 20:
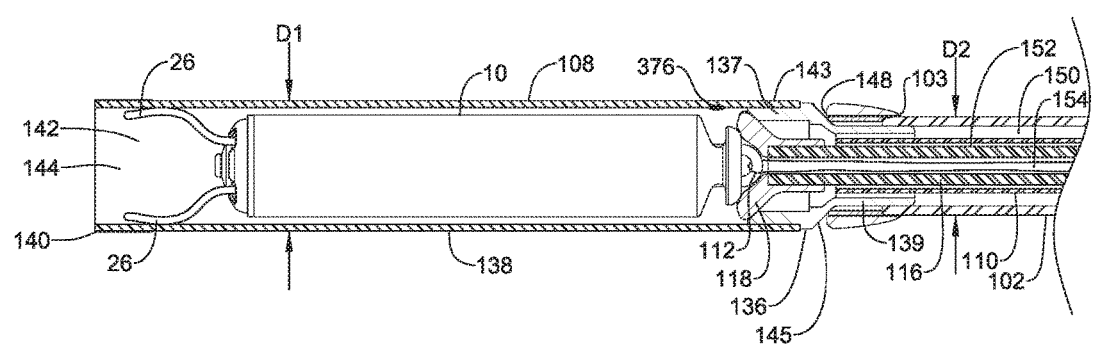
FIG. 20 is a schematic view of the distal portion of the delivery device of FIG. 12.

FIG. 20 provides an example of a force sensor 376 that may be disposed within the device containment housing 108. In some cases, the force sensor 376 may be a pressure sensor, and may provide an indication of whether fluid that may be pumped into the device containment housing 108 remains in the device containment housing, indicating a good contact between the tip 140 of the device containment housing 108 and the adjoining tissue, or if the fluid has leaked out, indicating poor contact. In some cases, the force sensor 376 may be positioned elsewhere along a fluid path to the device containment housing 108 and could even be disposed within the handle assembly 120.

In other instances, force sensor 376 may be a strain sensor or the like attached to or incorporated into the device containment housing wall. Such strain sensor may sense the axial, compressive and/or bending strain in the wall of the device containment housing, which will be related to the force applied to the cardiac tissue via the device containment housing. In some cases, the strain sensor may be a fiber optic or piezo type sensor. It will be appreciated that while not illustrated, the force sensors 370, 372, 374, 376 may include additional structure for communicating force values to an outside display, for example.

While the force sensors 370, 372, 374, 376 are illustrated in separate Figures, it will be appreciated that in some cases a delivery device may utilize two or more of the force sensors 370, 372, 374, 376 in combination. For example, a delivery device may include the force sensor 370 or the force sensor 372 in combination with the force sensor 374. A delivery device may, for example, include the force sensor 370 or the force sensor 374 in combination with the force sensor 376. A delivery device may include the force sensor 374 and the force sensor 376.

The materials that can be used for the various components of the delivery devices, such as delivery device 100 (and/or other delivery structures disclosed herein) and the various members disclosed herein may include those commonly associated with medical devices. For simplicity purposes, the following discussion makes reference to the delivery device 100 and the delivery and deployment device 200 and components thereof. However, this is not intended to limit the devices and methods described herein, as the discussion may be applied to other similar delivery systems and/or components of delivery systems or devices disclosed herein.

The delivery device 100 and/or the deployment and delivery device 200, or components thereof, may be made from a metal, metal alloy, polymer (some examples of which are disclosed below), a metal-polymer composite, ceramics, combinations thereof, and the like, or other suitable material. Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers thereof, polymer/metal composites, and the like. In some embodiments the polymer can be blended with a liquid crystal polymer (LCP). For example, the mixture can contain up to about 6 percent LCP.

Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; combinations thereof; and the like; or any other suitable material.

In at least some embodiments, portions or all of the delivery device 100 and/or the deployment and delivery device 200, or components thereof, may be doped with, made of, or otherwise include a radiopaque material. Radiopaque materials are understood to be materials capable of producing a relatively bright image on a fluoroscopy screen or another imaging technique during a medical procedure. This relatively bright image aids the user of the delivery device 100 in determining its location. Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of the delivery device 100 and/or the deployment and delivery device 200, or components thereof, to achieve the same result.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The disclosure's scope is, of course, defined in the language in which the appended claims are expressed.

What is claimed is:

1. A delivery and deployment device configured to deliver an implantable medical device (IMD) to a chamber of a patient's heart and deploy the IMD therein, the delivery and deployment device comprising:
a handle assembly;
a shaft extending distally from the handle assembly, the shaft including a distal region;
a device containment housing coupled to the distal region of the shaft and extending distally therefrom, the device containment housing configured to accommodate the IMD therein;
at least one of the shaft and the device containment housing including a compressible region, wherein:
when the shaft includes the compressible region, the compressible region comprises a portion of a wall of the shaft that compresses by an amount that is related to an applied force; and
when the device containment housing includes the compressible region, the compressible region comprises a portion of a wall of the device containment housing that compresses by an amount that is related to an applied force;
a first position indicator and a second position indicator, wherein at least part of the compressible region is situated between the first position indicator and the second position indicator; and
wherein a force applied to the device containment housing causes the compressible region to compress by an amount that is related to the applied force, which causes a change in distance between the first position indicator and the second position indicator, which provides an indication of the applied force.

2. The delivery and deployment device of claim 1, wherein the compressible region comprises a portion of the device containment housing.

3. The delivery and deployment device of claim 1, wherein the compressible region is configured to shorten in length in response to the applied force.

4. The delivery and deployment device of claim 1, wherein the first position indicator comprises a first radiopaque marker band and the second position indicator comprises a second radiopaque marker band, and the change in distance between the first position indicator and the second position indicator is visible via fluoroscopy.

5. The delivery and deployment device of claim 1, wherein the first position indicator comprises a first electrode and the second position indicator comprises a second electrode, and the change in distance between the first electrode and the second electrode is indicated via a change in impedance between the first electrode and the second electrode.

6. The delivery and deployment device of claim 5, wherein the first electrode comprises a ring electrode.

7. The delivery and deployment device of claim 5, wherein the first electrode comprises one of a plurality of electrodes that are disposed radially about a distal end of the device containment housing and alignable with each of a plurality of talons of the IMD.

8. The delivery and deployment device of claim 5, wherein the second electrode comprises a ring electrode.

9. The delivery and deployment device of claim 1, further comprising a force sensor arranged and configured to provide an indication of a force applied to the IMD during implantation.

10. The delivery and deployment device of claim 1, further comprising a force sensor arranged and configured to provide an indication of a force applied to an IMD during a tug test after deployment of the IMD.

* * * * *